United States Patent [19]
Tao et al.

[11] Patent Number: 5,801,013
[45] Date of Patent: Sep. 1, 1998

[54] HELICOBACTER AMINOACYL-TRNA SYNTHETASE PROTEINS, NUCLEIC ACIDS AND STRAINS COMPRISING SAME

[75] Inventors: Jianshi Tao, Needham; Yan Qiu, Brookline; Fariba Houman, Belmont; Xiaoyu Shen, S. Boston; Paul R. Schimmel, Cambridge, all of Mass.

[73] Assignee: Cubist Pharmaceuticals, Inc., Cambridge, Mass.

[21] Appl. No.: 451,715

[22] Filed: May 26, 1995

[51] Int. Cl.$^6$ .................. C12N 15/00; C12N 15/63; C07K 14/195; C07H 21/04
[52] U.S. Cl. .................. 435/69.1; 435/69.7; 435/252.3; 435/254.2; 435/320.1; 530/350; 530/23.2; 530/23.4; 530/24.32
[58] Field of Search .................. 435/6, 69.1, 69.7, 435/71.1, 71.2, 172.1, 172.3, 183, 243, 252.3, 252.33, 254.11, 254.2, 254.21, 320.1; 514/44; 536/23.1, 23.2, 23.4, 29.1, 24.32, 24.5

[56] References Cited

U.S. PATENT DOCUMENTS

| | | | |
|---|---|---|---|
| 4,713,337 | 12/1987 | Jasin et al. | 435/172.3 |
| 4,788,148 | 11/1988 | Nilsson et al. | 435/252.33 |
| 4,952,501 | 8/1990 | Jasin et al. | 435/69.2 |
| 4,963,487 | 10/1990 | Schimmel et al. | 435/172.3 |
| 5,370,995 | 12/1994 | Henneck et al. | 435/69.1 |
| 5,561,054 | 10/1996 | Kron et al. | 453/69.1 |
| 5,688,655 | 11/1997 | Housey | 435/7.21 |

FOREIGN PATENT DOCUMENTS

WO 95/09927   4/1995   WIPO.

OTHER PUBLICATIONS

Langenberg et al. "Identification of Campylobacter pyloridis isolates by restriction endonuclease DNA analysis" J. Clinical Microbiol. 24(3):414–417, Sep. 1986.
Taylor et al. "Construction of a Helicobacter pylori genome map and demonstration of diversity at the genome level." J. Bacteriol. 174(21):6800–6806, Nov. 1992.
Webster's II New Riveside Dictionary The Riverside Publishing Co., p. 1232, 1994.
Meinnel, T., et al., "Aminoacyl–tRNA Synthetases: Occurence, Structure, and Function." In tRNA: *Structure, Biosynthesis, and Function*, Söll, D. and RajBhandary, U., eds. (Washington, DC: American Society for Microbiology), pp. 251–300 (1995).
von der Haar, F. et al, "Target Directed Drug Synthesis: The Aminoacyl–tRNA Synthetase as Possible Targets," *Angew. Chem. Int. Ed. Engl.*, 20(3):217–223 (1981).
Walter, R. D. and Kuhlow, F., "Parasite–Specific Interaction of N–[4–(4' Nitroanilino)–Phenyl]–S–(β–Carboxyethyl)–Dithiocarbamic Acid–Ester with Arginyl–tRNA–Synthetase from *Dirofilaria immitis,*" *Trop. Med. Parasit.*, 36:230–232 (1985).

Hughes, J., et al., "Inhibition of Isoleucyl–Transfer Ribonucleic Acid Synthetase in *Escherichia coli* by Pseudomonic Acid," *Biochem. J.*, 176:305–318 (1978).
Hughes, J. and Mellows, G., "Interaction of Pseudomonic Acid A with *Escherichia coli* B Isoleucyl–tRNA Synthetase," *Biochem J.*, 191:209–219 (1980).
Racher, K.I., et al., "Expression and Characterization of a Recombinant Yeast Isoleucyl–tRNA Synthetase," *J. Biol. Chem.*, 266(26):17158–17164 (1991).
Chalker, A.F., et al., "Analysis and Toxic Overexpression in *Escherichia coli* of a Staphylococcal Gene Encoding Isoleucyl–tRNA Synthetase," *Gene*, 141:103–108 (1994).
Jasin, M. and Schimmel, P., "Deletion of an Essential Gene in *Eschericia coli* by Site–Specific Recombinant with Linear DNA Fragments," *J. Bacteriol.*, 159(2):783–786 (1984).
Shiba, K. and Shimmel, P., "Functional Assembly of a Randomly Cleaved Protein," *Proc. Natl. Acad. Sci. USA*, 89:1880–1884 (1992).
Shepard, A., et al., "RNA Binding Determinant in Some Class I tRNA Synthetases Identified by Alignment–Guided Mutagenesis," *Proc. Natl. Acad. Sci. USA*, 89:9964–9968 (1992).
Kim, S., et al., "Diversified Sequences of Peptide Epitope for Same–RNA Recognition," *Proc. Natl. Acad. Sci. USA*, 90:10046–10050 (1993).
Edwards, H., et al., "An *E. coli* Aminoacyl–tRNA Synthetase Can Substitute for Yeast Mitochondrial Enzyme Function In Vivo," *Cell*, 51:643–649 (1987).
Edwards, H. and Schimmel, P., "A Bacterial Amber Suppressor in *Saccharomyces cerevisiae* Is Selectively Recognized by a Bacterial Aminoacyl–tRNA Synthetase," *Mol. Cell. Biol.*, 10(4):1633–1641 (1990).

(List continued on next page.)

*Primary Examiner*—Nancy Degen
*Assistant Examiner*—Thomas G. Larson
*Attorney, Agent, or Firm*—Hamilton, Brook, Smith & Reynolds, P.C.

[57] ABSTRACT

Recombinant nucleic acids which encode aminoacyl-tRNA sythetases of helicobacter origin have been isolated. These nucleic acids can be used to make expression constructs and transformed host cells for the production of helicobacter aminoacyl-tRNA synthetases. They can also be used in the further isolation of nucleic acids related by DNA sequence similarities, which also encode helicobacter aminoacyl-tRNA synthetases, or portions thereof. A further embodiment of the invention is antisense nucleic acid which can hybridize to the nucleic acid which encodes the aminoacyl-tRNA synthetase of helicobacter. The invention also relates to isolated and/or recombinant helicobacter aminoacyl-tRNA synthetases. Antibodies which bind to these enzymes can be made and can be used in the purification and study of the enzymes. Also described are tester strains, which are cells engineered to rely on the function of the tRNA synthetase encoded by an introduced cloned gene, and which can be used to test the effectiveness of drug candidates in the inhibition of an essential aminoacyl-tRNA synthetase encoded by an introduced cloned helicobacter gene.

63 Claims, 5 Drawing Sheets

OTHER PUBLICATIONS

Weygand–Duraševič, I., et al., "Yeast Seryl–tRNA Synthetase Expressed in *Escherichia coli* Recognizes Bacterial Serine–Specific tRNAs in vivo," *Eur. J. Biochem.*, 214:869–877 (1993).

Jones, M. D., et al., "Natural Variation of Tyrosyl–tRNA Sythetase and Comparison with Engineered Mutants," *Biochemistry*, 25:1887–1891 (1986).

Henkin, T. M., et al., "Analysis of the *Bacillus subtilis* tyrS Gene: Conservation of a Regulatory Sequence in Multiple tRNA Synthetase Genes," *J. Bacteriol.*, 174(4):1299–1306 (1992).

Salazar, O., et al., "*Thiobacillus ferrooxidans* Tyrosyl–tRNA Synthetase Functions In Vivo in *Escherichia coli*," *J. Bacteriol.*, 176(14):4409–4415 (1994).

Iaccarino, M. and Berg, P., "Isoleucine Auxotrophy as a Consequence of a Mutationally Altered Isoleucyl–Transfer Ribonucleic Acid Synthetase," *J. Bacteriol.*, 105:527–537 (1970).

Archibold, E.R., and Williams, L.S., "Regulation fo Methionyl–Transfer Ribonucleic Acid Synthetase Formation in *Eschericia coli* and *Salmonella typhimurium*," *J. Bacteriol.*, 114(3):1007–1013 (1973).

Dardel, F., et al., "Molecular Cloning and Primary Structure of the *Eschericia coli* Methionyl–tRNA Synthetase Gene," *J. Bacteriol.*, 160(3):1115–1122 (1984)

Low, B., et al., "Isolation and Partial Characterization of Temperature–Sensitive *Eschericia coli* Mutants with Altered Leucyl– and Seryl–Transfer Ribonucleic Acid Synthetases," *J. Bacteriol.*, 108(2):742–750 (1971).

Clarke, S. J., et al., "Isolation and Characterization of a Regulatory Mutant of an Aminoacyl–Transfer Ribonucleic Acid Synthetase in *Escherichia coli* K–12," *J. Bacteriol.*, 113(3):1096–1103 (1973).

Schlesinger, S., and Nester, E. W., "Mutants of *Escherichia coli* with an Altered Tryosyl–Transfer Ribonucleic Acid Synthetase," *J. Bacteriol.*, 100(1):167–175 (1969).

Gatti, D.L., and Tzagoloff, A., "Structure and Evolution of a Group of Related Aminoacyl–tRNA Synthetases," *J. Mol. Biol.*, 218:557–568 (1991).

Tzagoloff, A., et al., "Characterization of MSM1, the Structural Gene for Yeast Mitochondiral Methionyl–tRNA Synthetase," *Eur. J. Biochem.*, 179:365–371 (1989).

Webster, T., et al., "Specific Sequence Homology and Three–Dimensional Structural of an Aminoacyl Transfer RNA Synthetase," *Science*, 226:1315–1317 (1984).

Jenal, U., et al., "Isoleucyl–tRNA Synthetase of MEthanobacterium thermautotrophicum Marburg," *J. Biol. Chem.*, 266(16):10570–10577 (1991).

Shiba, K., et al., "Human cytoplasmic isoleucyl–tRNA synthetase: Selective divergence of the anticondon–binding domain and acquisition of a new structural unit," *Proc. Natl. Acad. Sci. USA*, 91:7435–7439 (1994).

Shiba, K., et al., "Isolation of Higher Eukaryote Aminoacyl–tRNA Synthetase Genes by an Alignment–Guided Cross–Species PCR: Application to Human Isoleucine tRNA Synthetase," [From *Programme and Abstracts*, p. F.46], 15th International tRNA Workshop, SociétéFrancaise de Biochimie et Biologie Moléculaire, Cap d'Agde, France, May 30–Jun. 4 (1993), Abstract No. 364.

Printout of a computer record of parts of a poster presented at Cap d'Agde, France, May 30–Jun. 4, 1993, 15th International tRNA Workshop, Société Francaise de Biochimie et Biologie Moléculare.

Hong, Y., et al., Data Submission, Isoleucyl–tRNA Synthetase, *Campylobacter jejuni*, GenBank Accession No. U15295 (1994).

Nureki, O., et al., "Methionyl–tRNA Synthetase from an Extreme Thermophile, *Thermus thermopilus* HB8," *J. Biol. Chem.*, 266 (5):3268–3277 (1991).

Mechulam, Y., et al., "Methionyl–tRNA Synthetase from *Bacillus stearothermophilus*: Structural and Functional Indentities with the *Escherichia coli* Enzyme," *Nucleic Acids Research*, 19(13):3673–3681 (1991).

Härtlein, M. and Madern, D., "Molecular Cloning and Nucleotide Sequence of the Gene for *Escherichia coli* Leucyl–tRNA Synthetase," *Nucleic Acids Research*, 15(24): 10199–10210 (1987).

Vander Horn, P. B., and Zahler, S. A., "Cloning and Nucleotide Sequence of the Leucyl–tRNA Sythetase Gene fo *Bacillus subtilis*," *J. Bacteriol.*, 174(12):3928–3935 (1992).

Borgford, T.J., et al., "The Valyl–tRNA Synthetase from *Bacilus stearothermophilus* Has Considerable Sequence Homology with the Isoleucyl–tRNA Synthetase from *Escherichia coli*", *Biochemistry*, 26: 2480–2486 (1987).

Härtlein, M., et al., "Nucleotide sequence of *Escherichia coli* valyl–tRNA synthetase gene valS", *Nucleic Acids Research*, 15(21): 9081–9082 (1987).

Heck, J.D., and Hatfield, G.W., "Valyl–tRNA Synthetase Gene of *Escherichia coli* K 12", *J. Biol. Chem.*, 263(2): 686–877 (1988).

Chan, V.L. and Bingham, H.L., "Lysl–tRNA Synthetase Gene of *Campylobacter jejuni*", *J. Bacteriol.*, 174(3): 695–701 (1992).

Lévêque, F., et al., "Homology of lysS and lysU, the two *Escherichia coli* genes encoding distinct lysyl–tRNA synthetase species", *Nucleic Acids Research*, 18(2): 305–312 (1990).

Clark, R.L. and Neidhart, F.C., "Roles of the Two Lysyl–tRNA Synthetases of *Escherichia coli*: Analysis of Nucleotide Sequences and Mutant Behavior", *J. Bacteriol.*, 172(6): 3237–3243 (1990).

Kawakami, K., et al., "Chromosomal location and structure of the operon encoding peptide–chain–release factor 2 of *Escherichia coli*", *Proc. Natl. Acad. Sci. USA*, 85: 5620–5624 (1988).

Härtlein, M., et al., "Cloning and characterization of the gene for *Escherichia coli* seryl–tRNA synthetase", *Nucleic Acids Research*, 15(3): 1005–1017 (1987).

Data Submission, seryl–tRNA Synthetase, *coxiella burnetti*, EMBL Accession No. X75627, (1994).

Bukanov, N.O. and Berg, D.E., "Ordered cosmid library and high–resolution physical–genetic map of *Helicobacter pylori* strain NCTC11638", *Molecular Microbiology*, 11(3): 509–523 (1994).

Phadnis, S.H., et al., "Pathological Significance and Molecular Characterization of the Vacuolating Toxin Gene of *Helicobacter pylori*", *Infection and Immunity*, 62(5): 1557–1565 (1994).

Nowak, R., "Getting the Bugs Worked Out", *Science*, 267: 172–174 (1995).

Craig, C., "Genome Therapeutics Sequences Complete *H. pylori* Genome", *BioWorld Today*, 5(239): 1–2 (1994).

SEQUENCE LISTING ( 1 ) GENERAL INFORMATION:

( i i i ) NUMBER OF SEQUENCES: 67

( 2 ) INFORMATION FOR SEQ ID NO:1:

( i ) SEQUENCE CHARACTERISTICS:
        ( A ) LENGTH: 2998 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 149..2908

( x i ) SEQUENCE DESCRIPTION: SEQ ID NO:1:

```
CGATGCGATT  AGCTTGCATT  ATTTAAAAGG  GATAGAAGAA  TACACGATTT  TACAAATCCC      60

CACTTTAAAA  AATGTGCCGC  GAAAAGACAC  GCACCTTTAT  ATCGCTCCTA  AAACAAAAGA     120

ATAAAGATAA  AAGATTAAGG  AACAATCA GTG AAA GAA TAC AAA GAC ACC CTA           172
                                 Met Lys Glu Tyr Lys Asp Thr Leu
                                  1               5

AAC TTA AAC ACA ACC ACC TTT TCT ATG AAA GGG AAT TTG AGC GTT AAT            220
Asn Leu Asn Thr Thr Thr Phe Ser Met Lys Gly Asn Leu Ser Val Asn
     10              15                  20

GAG CCT AAA ACT TAC GCA AAA TGG CAA GAG CAA CAA GCG TTC AAA CGC            268
Glu Pro Lys Thr Tyr Ala Lys Trp Gln Glu Gln Gln Ala Phe Lys Arg
 25              30                  35                  40

ATG CAA GCT AGG AAA GAT AAC CAT GGG GAT TTC ACC TTG CAT GAC GGG            316
Met Gln Ala Arg Lys Asp Asn His Gly Asp Phe Thr Leu His Asp Gly
                 45                  50                  55

CCG CCT TAT GCG AAC GGG CAT TTG CAT TTA GGG CAT GCC TTA AAT AAA            364
Pro Pro Tyr Ala Asn Gly His Leu His Leu Gly His Ala Leu Asn Lys
             60                  65                  70

ATT TTA AAA GAC ATT GTT ATT AAA AGG GAA TAT TTT AAA GGG AAG AAA            412
Ile Leu Lys Asp Ile Val Ile Lys Arg Glu Tyr Phe Lys Gly Lys Lys
```

-continued

```
                  75                          80                          85
ATC  TAT  TAC  ACG  CCC  GGT  TGG  GAT  TGC  CAT  GGC  TTG  CCC  ATT  GAG  CAG              460
Ile  Tyr  Tyr  Thr  Pro  Gly  Trp  Asp  Cys  His  Gly  Leu  Pro  Ile  Glu  Gln
          90                            95                          100

CAA  ATT  TTA  GAG  CGA  TTA  GAA  AAA  GAA  AAA  ACG  AGC  CTA  GAA  AAC  CCC              508
Gln  Ile  Leu  Glu  Arg  Leu  Glu  Lys  Glu  Lys  Thr  Ser  Leu  Glu  Asn  Pro
105                           110                         115                     120

ACG  CTG  TTT  AGA  GAA  AAG  TGC  CGA  GAT  CAT  GCG  AAG  AAA  TTT  TTA  GAA              556
Thr  Leu  Phe  Arg  Glu  Lys  Cys  Arg  Asp  His  Ala  Lys  Lys  Phe  Leu  Glu
                    125                         130                         135

ATC  CAA  AAG  AAT  GAA  TTT  TTG  CAA  TTA  GGC  GTT  TTG  GGG  GAT  TTT  GAA              604
Ile  Gln  Lys  Asn  Glu  Phe  Leu  Gln  Leu  Gly  Val  Leu  Gly  Asp  Phe  Glu
               140                         145                         150

GAT  CCT  TAT  AAA  ACC  ATG  GAT  TTT  AAA  TTT  GAA  GCG  AGC  ATT  TAT  AGG              652
Asp  Pro  Tyr  Lys  Thr  Met  Asp  Phe  Lys  Phe  Glu  Ala  Ser  Ile  Tyr  Arg
                    155                         160                         165

GCC  TTA  GTG  GAA  GTG  GCT  AAA  AAA  GGG  CTT  TTG  AAA  GAG  CGC  CAT  AAG              700
Ala  Leu  Val  Glu  Val  Ala  Lys  Lys  Gly  Leu  Leu  Lys  Glu  Arg  His  Lys
          170                         175                         180

CCT  ATT  TAT  TGG  AGT  TAT  GCA  TGC  GAG  AGC  GCT  TTA  GCG  GAA  GCT  GAA              748
Pro  Ile  Tyr  Trp  Ser  Tyr  Ala  Cys  Glu  Ser  Ala  Leu  Ala  Glu  Ala  Glu
185                           190                         195                     200

GTG  GAA  TAC  AAG  ATG  AAA  AAA  TCG  CCC  TCC  ATT  TTC  GTG  GCG  TTT  GAT              796
Val  Glu  Tyr  Lys  Met  Lys  Lys  Ser  Pro  Ser  Ile  Phe  Val  Ala  Phe  Asp
                         205                         210                         215

TTG  AAA  AAA  GAG  AGT  TTA  GAA  AAA  TTA  AAA  GTC  AAA  AAA  GCG  AGC  TTG              844
Leu  Lys  Lys  Glu  Ser  Leu  Glu  Lys  Leu  Lys  Val  Lys  Lys  Ala  Ser  Leu
                    220                         225                         230

GTG  ATT  TGG  ACG  ACC  ACG  CCC  TGG  ACT  TTG  TAT  GCG  AAT  GAA  GCG  ATC              892
Val  Ile  Trp  Thr  Thr  Thr  Pro  Trp  Thr  Leu  Tyr  Ala  Asn  Glu  Ala  Ile
               235                         240                         245

GCT  TTG  AAA  AAG  GAC  GCT  GTT  TAT  GTG  CTC  ACC  CAA  AAA  GGC  TAT  TTA              940
Ala  Leu  Lys  Lys  Asp  Ala  Val  Tyr  Val  Leu  Thr  Gln  Lys  Gly  Tyr  Leu
          250                         255                         260

GTC  GCT  AAA  GCC  TTG  CAT  GAA  AAA  TTA  GCC  GCT  TTA  GGG  GTG  GTG  GAT              988
Val  Ala  Lys  Ala  Leu  His  Glu  Lys  Leu  Ala  Ala  Leu  Gly  Val  Val  Asp
265                           270                         275                     280

AGT  GAG  ATC  ACG  CAT  GAA  TTT  AAC  GCT  AAT  GAT  TTA  GAA  TAC  TTG  AAG              1036
Ser  Glu  Ile  Thr  His  Glu  Phe  Asn  Ala  Asn  Asp  Leu  Glu  Tyr  Leu  Lys
                         285                         290                         295

GCC  ACC  AAT  CCT  TTA  AAC  CAA  AGA  GAT  TCC  CTA  ATC  ACT  CTA  GGA  GAG              1084
Ala  Thr  Asn  Pro  Leu  Asn  Gln  Arg  Asp  Ser  Leu  Ile  Thr  Leu  Gly  Glu
                    300                         305                         310

CAT  GTC  GGT  TTA  GAA  GAT  GGC  ACA  GGA  GCC  GTG  CAT  ACC  GCA  CCT  GGG              1132
His  Val  Gly  Leu  Glu  Asp  Gly  Thr  Gly  Ala  Val  His  Thr  Ala  Pro  Gly
               315                         320                         325

CAT  GGT  GAA  GAG  GAC  TAT  TAT  TTA  GGC  TTA  AAA  TAC  AAT  TTA  GAA  GTG              1180
His  Gly  Glu  Glu  Asp  Tyr  Tyr  Leu  Gly  Leu  Lys  Tyr  Asn  Leu  Glu  Val
          330                         335                         340

TTA  ATG  TCC  GTA  GAT  GAG  AAA  GGT  TGC  TAT  GAT  GAG  GGC  ATT  ATC  CAT              1228
Leu  Met  Ser  Val  Asp  Glu  Lys  Gly  Cys  Tyr  Asp  Glu  Gly  Ile  Ile  His
345                           350                         355                     360

AAC  CAA  CTA  TTA  GAT  GAA  AGC  TAT  CTG  GGC  GAG  CAT  GTT  TTT  AAG  GCT              1276
Asn  Gln  Leu  Leu  Asp  Glu  Ser  Tyr  Leu  Gly  Glu  His  Val  Phe  Lys  Ala
                         365                         370                         375

CAA  AAA  CGC  ATT  ATA  GAG  CAA  TTG  GGC  GAT  TCT  TTA  TTG  CTG  GAG  CAA              1324
Gln  Lys  Arg  Ile  Ile  Glu  Gln  Leu  Gly  Asp  Ser  Leu  Leu  Leu  Glu  Gln
                    380                         385                         390

GAG  ATT  GAG  CAT  TCC  TAC  CCG  CAT  TGC  TGG  AGG  ACG  CAC  AAG  CCT  GTG              1372
Glu  Ile  Glu  His  Ser  Tyr  Pro  His  Cys  Trp  Arg  Thr  His  Lys  Pro  Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 395 |     |     |     | 400 |     |     |     |     | 405 |     |     |     |     |      |
| ATT | TAC | AGA | GCG | ACC | ACG | CAA | TGG | TTT | ATT | TTA | ATG | GAT | GAG | CCT | TTT | 1420 |
| Ile | Tyr | Arg | Ala | Thr | Thr | Gln | Trp | Phe | Ile | Leu | Met | Asp | Glu | Pro | Phe |      |
|     | 410 |     |     |     |     | 415 |     |     |     |     | 420 |     |     |     |     |      |
| ATT | CAA | AAT | GAT | GGT | TCT | CAA | AAA | ACC | TTA | AGA | GAA | GTG | GCT | TTG | AGT | 1468 |
| Ile | Gln | Asn | Asp | Gly | Ser | Gln | Lys | Thr | Leu | Arg | Glu | Val | Ala | Leu | Ser |      |
| 425 |     |     |     |     | 430 |     |     |     |     | 435 |     |     |     |     | 440 |      |
| GCG | ATT | GAA | AAG | GTG | GAA | TTT | GTG | CCA | AGC | AAC | GGG | AAA | AAC | CGC | CTA | 1516 |
| Ala | Ile | Glu | Lys | Val | Glu | Phe | Val | Pro | Ser | Asn | Gly | Lys | Asn | Arg | Leu |      |
|     |     |     |     | 445 |     |     |     |     | 450 |     |     |     |     | 455 |     |      |
| AAA | ACC | ATG | ATA | GAA | AAC | CGC | CCT | GAT | TGG | TGC | TTG | AGC | CGG | CAA | AGA | 1564 |
| Lys | Thr | Met | Ile | Glu | Asn | Arg | Pro | Asp | Trp | Cys | Leu | Ser | Arg | Gln | Arg |      |
|     |     | 460 |     |     |     |     |     | 465 |     |     |     | 470 |     |     |     |      |
| AAA | TGG | GGC | GTG | CCA | CTG | GCC | TTT | TTC | ATA | GAC | AAA | CGT | ACG | AAT | AAG | 1612 |
| Lys | Trp | Gly | Val | Pro | Leu | Ala | Phe | Phe | Ile | Asp | Lys | Arg | Thr | Asn | Lys |      |
|     |     | 475 |     |     |     |     |     | 480 |     |     |     |     | 485 |     |     |      |
| CCT | TGT | TTT | GAA | AGC | GAA | GTT | TTA | GAG | CAT | GTG | GCG | AAT | CTT | TTT | GAG | 1660 |
| Pro | Cys | Phe | Glu | Ser | Glu | Val | Leu | Glu | His | Val | Ala | Asn | Leu | Phe | Glu |      |
|     | 490 |     |     |     |     | 495 |     |     |     |     | 500 |     |     |     |     |      |
| AAA | AAA | GGT | TGT | GAT | GTG | TGG | TGG | GAG | TCT | AGC | GTA | AAA | GAT | TTA | TTA | 1708 |
| Lys | Lys | Gly | Cys | Asp | Val | Trp | Trp | Glu | Ser | Ser | Val | Lys | Asp | Leu | Leu |      |
| 505 |     |     |     |     | 510 |     |     |     |     | 515 |     |     |     |     | 520 |      |
| CCC | CCT | AGC | TAT | CAA | GAG | GAC | GCC | AAG | CAT | TAC | GAA | AAA | ATC | ATG | CAC | 1756 |
| Pro | Pro | Ser | Tyr | Gln | Glu | Asp | Ala | Lys | His | Tyr | Glu | Lys | Ile | Met | His |      |
|     |     |     |     | 525 |     |     |     |     | 530 |     |     |     |     | 535 |     |      |
| ATT | TTA | GAT | GTG | TGG | TTT | GAT | AGT | GGT | AGC | ACC | TTT | AAG | GCG | GTT | TTA | 1804 |
| Ile | Leu | Asp | Val | Trp | Phe | Asp | Ser | Gly | Ser | Thr | Phe | Lys | Ala | Val | Leu |      |
|     |     |     | 540 |     |     |     |     | 545 |     |     |     |     | 550 |     |     |      |
| GAA | GAC | TAT | CAT | GGA | GAA | AAA | GGG | CAA | AGC | CCT | AGT | GAT | GTG | GTT | TTA | 1852 |
| Glu | Asp | Tyr | His | Gly | Glu | Lys | Gly | Gln | Ser | Pro | Ser | Asp | Val | Val | Leu |      |
|     |     | 555 |     |     |     |     | 560 |     |     |     |     | 565 |     |     |     |      |
| GAA | GGG | AGC | GAT | CAG | CAT | AGG | GGG | TGG | TTT | CAA | AGT | TCG | CTT | CTA | ATC | 1900 |
| Glu | Gly | Ser | Asp | Gln | His | Arg | Gly | Trp | Phe | Gln | Ser | Ser | Leu | Leu | Ile |      |
|     | 570 |     |     |     |     | 575 |     |     |     |     | 580 |     |     |     |     |      |
| GGT | TGT | GTT | TTA | AAC | AAC | CAA | GCC | CCT | TTT | AAA | AAG | GTC | ATT | ACG | CAT | 1948 |
| Gly | Cys | Val | Leu | Asn | Asn | Gln | Ala | Pro | Phe | Lys | Lys | Val | Ile | Thr | His |      |
| 585 |     |     |     |     | 590 |     |     |     |     | 595 |     |     |     |     | 600 |      |
| GGC | TTT | ATC | GTC | GAT | GAA | AAG | GGC | GAG | AAA | ATG | AGT | AAA | TCT | AAG | GGC | 1996 |
| Gly | Phe | Ile | Val | Asp | Glu | Lys | Gly | Glu | Lys | Met | Ser | Lys | Ser | Lys | Gly |      |
|     |     |     |     | 605 |     |     |     |     | 610 |     |     |     |     | 615 |     |      |
| AAT | GTG | GTG | TCT | TTG | GAC | AAC | TTA | CTC | AAA | AAG | CAT | GGG | AGC | GAT | GTG | 2044 |
| Asn | Val | Val | Ser | Leu | Asp | Asn | Leu | Leu | Lys | Lys | His | Gly | Ser | Asp | Val |      |
|     |     |     | 620 |     |     |     |     | 625 |     |     |     |     | 630 |     |     |      |
| GTG | CGT | TTG | TGG | GTA | GCG | TTT | AAT | GAC | TAT | CAA | AAC | GAT | TTG | AGG | GTC | 2092 |
| Val | Arg | Leu | Trp | Val | Ala | Phe | Asn | Asp | Tyr | Gln | Asn | Asp | Leu | Arg | Val |      |
|     |     | 635 |     |     |     |     | 640 |     |     |     |     | 645 |     |     |     |      |
| TCT | CAA | ACC | TTC | TTC | ATT | CAA | ACA | GAA | CAG | CAT | TAT | AAG | AAA | TTC | CGC | 2140 |
| Ser | Gln | Thr | Phe | Phe | Ile | Gln | Thr | Glu | Gln | His | Tyr | Lys | Lys | Phe | Arg |      |
|     | 650 |     |     |     |     | 655 |     |     |     |     | 660 |     |     |     |     |      |
| AAC | ACC | CTT | AAA | TTC | TTA | CTC | GCC | AAT | TTT | AGC | GAT | ATG | GAT | CTT | AAG | 2188 |
| Asn | Thr | Leu | Lys | Phe | Leu | Leu | Ala | Asn | Phe | Ser | Asp | Met | Asp | Leu | Lys |      |
| 665 |     |     |     |     | 670 |     |     |     |     | 675 |     |     |     |     | 680 |      |
| AAT | TTA | GAA | CGA | TCC | CAT | GAC | TTC | AGC | CCT | TTA | GAT | CAT | TTT | ATA | TTA | 2236 |
| Asn | Leu | Glu | Arg | Ser | His | Asp | Phe | Ser | Pro | Leu | Asp | His | Phe | Ile | Leu |      |
|     |     |     |     | 685 |     |     |     |     | 690 |     |     |     |     | 695 |     |      |
| GAG | GCT | TTA | GAA | ACA | ACA | AGC | GTT | GGA | GTC | AAT | AGC | GCG | TTT | GAA | GAG | 2284 |
| Glu | Ala | Leu | Glu | Thr | Thr | Ser | Val | Gly | Val | Asn | Ser | Ala | Phe | Glu | Glu |      |
|     |     |     | 700 |     |     |     |     | 705 |     |     |     |     | 710 |     |     |      |
| CAT | GAT | TTT | GTG | AAG | GGC | TTG | AAT | ATT | TTA | ATG | GCG | TTT | GTT | ACC | AAT | 2332 |
| His | Asp | Phe | Val | Lys | Gly | Leu | Asn | Ile | Leu | Met | Ala | Phe | Val | Thr | Asn |      |

-continued

```
                        715                                720                                725
GAA   TTG   AGT   GGG   ATT   TAT   TTA   GAC   GCT   TGT   AAG   GAT   AGC   TTG   TAT   TGC        2380
Glu   Leu   Ser   Gly   Ile   Tyr   Leu   Asp   Ala   Cys   Lys   Asp   Ser   Leu   Tyr   Cys
      730                     735                                 740

GAT   AGC   AAA   AAC   AAT   GAA   AAA   CGC   CAA   GCC   ATT   CAA   ATG   GTC   TTA   CTC        2428
Asp   Ser   Lys   Asn   Asn   Glu   Lys   Arg   Gln   Ala   Ile   Gln   Met   Val   Leu   Leu
745                           750                                 755                          760

GCT   GTG   GCT   AGT   AAG   TTG   TGC   TAC   TTT   TTA   GCC   CCG   ATT   TTA   ACG   CAC        2476
Ala   Val   Ala   Ser   Lys   Leu   Cys   Tyr   Phe   Leu   Ala   Pro   Ile   Leu   Thr   His
                  765                                 770                                 775

ACG   ATT   GAA   GAG   GTT   TTA   GAG   CAT   AGT   CAG   GTG   CTG   TGC   GCG   TTT   TTA        2524
Thr   Ile   Glu   Glu   Val   Leu   Glu   His   Ser   Gln   Val   Leu   Cys   Ala   Phe   Leu
            780                                 785                                 790

CAA   GCC   AAA   GAT   GTG   TTT   GAT   TTA   AAA   GAC   ATT   AGC   GTT   TCA   GAA   AAA        2572
Gln   Ala   Lys   Asp   Val   Phe   Asp   Leu   Lys   Asp   Ile   Ser   Val   Ser   Glu   Lys
      795                                 800                                 805

CTC   CAC   CTT   AAA   GAG   TTT   AAA   AAA   CCA   GAA   AAT   TTT   GAA   GCC   GTT   TTA        2620
Leu   His   Leu   Lys   Glu   Phe   Lys   Lys   Pro   Glu   Asn   Phe   Glu   Ala   Val   Leu
810                                 815                                 820

GCC   TTG   CGT   TCT   GCC   TTT   AAT   GAA   GAG   TTA   GAC   CGA   TTG   AAA   AAA   GAA        2668
Ala   Leu   Arg   Ser   Ala   Phe   Asn   Glu   Glu   Leu   Asp   Arg   Leu   Lys   Lys   Glu
825                           830                                 835                          840

GGC   GTC   ATT   AAA   AAT   TCG   TTG   GAG   TGC   GCT   ATT   GAA   GTA   AAA   GAA   AAA        2716
Gly   Val   Ile   Lys   Asn   Ser   Leu   Glu   Cys   Ala   Ile   Glu   Val   Lys   Glu   Lys
                        845                                 850                          855

GCG   TTG   CGT   GAA   AAT   TTG   ATA   GAA   GAA   TTG   CTG   ATG   GTG   AGC   TTT   GTG        2764
Ala   Leu   Arg   Glu   Asn   Leu   Ile   Glu   Glu   Leu   Leu   Met   Val   Ser   Phe   Val
                  860                                 865                           870

GGG   GTT   GCA   AAA   GAA   AAA   TTA   AGC   GAA   ACG   CCA   GCA   TTC   ACG   CTC   TTT        2812
Gly   Val   Ala   Lys   Glu   Lys   Leu   Ser   Glu   Thr   Pro   Ala   Phe   Thr   Leu   Phe
            875                                 880                                 885

AAA   GCC   CCC   TTT   TAT   AAA   TGC   CCT   AGG   TGT   TGG   CGT   TTT   AAA   AGC   GAA        2860
Lys   Ala   Pro   Phe   Tyr   Lys   Cys   Pro   Arg   Cys   Trp   Arg   Phe   Lys   Ser   Glu
      890                                 895                                 900

TTA   GAA   AAC   ACC   CCT   TGC   AAG   CGC   TGC   GAA   GAG   GTT   TTA   AAA   GAG   CGA        2908
Leu   Glu   Asn   Thr   Pro   Cys   Lys   Arg   Cys   Glu   Glu   Val   Leu   Lys   Glu   Arg
905                           910                                 915                          920

TGATAAAAGG   ATAGGGCTTT   TGGAAACTTT   ACAAACCCAT   AGAGTTTTAC   AAGCCCTAAT                         2968

CGGCCATTTC   ACCCCATTTT   TAGAAAGTGG                                                                2998
```

( 2 ) INFORMATION FOR SEQ ID NO:2:

( i ) SEQUENCE CHARACTERISTICS:
        ( A ) LENGTH: 920 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met   Lys   Glu   Tyr   Lys   Asp   Thr   Leu   Asn   Leu   Asn   Thr   Thr   Thr   Phe   Ser
1                       5                             10                            15

Met   Lys   Gly   Asn   Leu   Ser   Val   Asn   Glu   Pro   Lys   Thr   Tyr   Ala   Lys   Trp
                  20                            25                            30

Gln   Glu   Gln   Gln   Ala   Phe   Lys   Arg   Met   Gln   Ala   Arg   Lys   Asp   Asn   His
                        35                            40                            45

Gly   Asp   Phe   Thr   Leu   His   Asp   Gly   Pro   Pro   Tyr   Ala   Asn   Gly   His   Leu
                  50                            55                            60

His   Leu   Gly   His   Ala   Leu   Asn   Lys   Ile   Leu   Lys   Asp   Ile   Val   Ile   Lys
65                            70                            75                            80
```

| | | | | | | | | | | | | | | | |
|---|---|---|---|---|---|---|---|---|---|---|---|---|---|---|---|
|Arg|Glu|Tyr|Phe|Lys 85|Gly|Lys|Lys|Ile 90|Tyr|Thr|Pro|Gly|Trp 95|Asp|
|Cys|His|Gly|Leu 100|Pro|Ile|Glu|Gln 105|Ile|Leu|Glu|Arg|Leu 110|Glu|Lys|
|Glu|Lys|Thr 115|Ser|Leu|Glu|Asn|Pro 120|Thr|Leu|Phe|Arg|Glu 125|Lys|Cys|Arg|
|Asp|His 130|Ala|Lys|Lys|Phe|Leu 135|Glu|Ile|Gln|Lys|Asn 140|Glu|Phe|Leu|Gln|
|Leu 145|Gly|Val|Leu|Gly|Asp 150|Phe|Glu|Asp|Pro|Tyr 155|Lys|Thr|Met|Asp|Phe 160|
|Lys|Phe|Glu|Ala|Ser 165|Ile|Tyr|Arg|Ala|Leu 170|Val|Glu|Val|Ala|Lys 175|Lys|
|Gly|Leu|Leu|Lys 180|Glu|Arg|His|Lys|Pro 185|Ile|Tyr|Trp|Ser|Tyr 190|Ala|Cys|
|Glu|Ser|Ala 195|Leu|Ala|Glu|Ala|Glu 200|Val|Glu|Tyr|Lys|Met 205|Lys|Lys|Ser|
|Pro|Ser 210|Ile|Phe|Val|Ala|Phe 215|Asp|Leu|Lys|Lys|Glu 220|Ser|Leu|Glu|Lys|
|Leu 225|Lys|Val|Lys|Lys|Ala 230|Ser|Leu|Val|Ile|Trp 235|Thr|Thr|Thr|Pro|Trp 240|
|Thr|Leu|Tyr|Ala|Asn 245|Glu|Ala|Ile|Ala|Leu 250|Lys|Lys|Asp|Ala|Val 255|Tyr|
|Val|Leu|Thr|Gln 260|Lys|Gly|Tyr|Leu|Val 265|Ala|Lys|Ala|Leu|His 270|Glu|Lys|
|Leu|Ala|Ala 275|Leu|Gly|Val|Val|Asp 280|Ser|Glu|Ile|Thr|His 285|Glu|Phe|Asn|
|Ala|Asn 290|Asp|Leu|Glu|Tyr|Leu 295|Lys|Ala|Thr|Asn|Pro 300|Leu|Asn|Gln|Arg|
|Asp 305|Ser|Leu|Ile|Thr|Leu 310|Gly|Glu|His|Val|Gly 315|Leu|Glu|Asp|Gly|Thr 320|
|Gly|Ala|Val|His|Thr 325|Ala|Pro|Gly|His|Gly 330|Glu|Glu|Asp|Tyr|Tyr 335|Leu|
|Gly|Leu|Lys|Tyr 340|Asn|Leu|Glu|Val|Leu 345|Met|Ser|Val|Asp|Glu 350|Lys|Gly|
|Cys|Tyr|Asp 355|Glu|Gly|Ile|Ile|His 360|Asn|Gln|Leu|Leu|Asp 365|Glu|Ser|Tyr|
|Leu|Gly 370|Glu|His|Val|Phe|Lys 375|Ala|Gln|Lys|Arg|Ile 380|Ile|Glu|Gln|Leu|
|Gly 385|Asp|Ser|Leu|Leu|Leu 390|Glu|Gln|Glu|Ile|Glu 395|His|Ser|Tyr|Pro|His 400|
|Cys|Trp|Arg|Thr|His 405|Lys|Pro|Val|Ile|Tyr 410|Arg|Ala|Thr|Thr|Gln 415|Trp|
|Phe|Ile|Leu|Met 420|Asp|Glu|Pro|Phe|Ile 425|Gln|Asn|Asp|Gly|Ser 430|Gln|Lys|
|Thr|Leu|Arg 435|Glu|Val|Ala|Leu|Ser 440|Ala|Ile|Glu|Lys|Val 445|Glu|Phe|Val|
|Pro|Ser 450|Asn|Gly|Lys|Asn|Arg 455|Leu|Lys|Thr|Met|Ile 460|Glu|Asn|Arg|Pro|
|Asp 465|Trp|Cys|Leu|Ser|Arg 470|Gln|Arg|Lys|Trp|Gly 475|Val|Pro|Leu|Ala|Phe 480|
|Phe|Ile|Asp|Lys|Arg 485|Thr|Asn|Lys|Pro|Cys 490|Phe|Glu|Ser|Glu|Val 495|Leu|
|Glu|His|Val|Ala|Asn|Leu|Phe|Glu|Lys|Lys|Gly|Cys|Asp|Val|Trp|Trp|

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 500 |     |     |     | 505 |     |     |     | 510 |     |     |
| Glu | Ser | Ser | Val | Lys | Asp | Leu | Leu | Pro | Pro | Ser | Tyr | Gln | Glu | Asp | Ala |
| Lys | His | Tyr | Glu | Lys | Ile | Met | His | Ile | Leu | Asp | Val | Trp | Phe | Asp | Ser |
|     |     | 515 |     |     |     | 520 |     |     |     |     | 525 |     |     |     |
|     |     | 530 |     |     |     | 535 |     |     |     | 540 |     |     |     |     |
| Gly | Ser | Thr | Phe | Lys | Ala | Val | Leu | Glu | Asp | Tyr | His | Gly | Glu | Lys | Gly |
| 545 |     |     |     |     | 550 |     |     |     |     | 555 |     |     |     |     | 560 |
| Gln | Ser | Pro | Ser | Asp | Val | Val | Leu | Glu | Gly | Ser | Asp | Gln | His | Arg | Gly |
|     |     |     |     | 565 |     |     |     |     | 570 |     |     |     |     | 575 |     |
| Trp | Phe | Gln | Ser | Ser | Leu | Leu | Ile | Gly | Cys | Val | Leu | Asn | Asn | Gln | Ala |
|     |     |     | 580 |     |     |     |     | 585 |     |     |     |     | 590 |     |     |
| Pro | Phe | Lys | Lys | Val | Ile | Thr | His | Gly | Phe | Ile | Val | Asp | Glu | Lys | Gly |
|     |     | 595 |     |     |     |     | 600 |     |     |     |     | 605 |     |     |     |
| Glu | Lys | Met | Ser | Lys | Ser | Lys | Gly | Asn | Val | Val | Ser | Leu | Asp | Asn | Leu |
|     | 610 |     |     |     |     | 615 |     |     |     |     | 620 |     |     |     |     |
| Leu | Lys | Lys | His | Gly | Ser | Asp | Val | Val | Arg | Leu | Trp | Val | Ala | Phe | Asn |
| 625 |     |     |     |     | 630 |     |     |     |     | 635 |     |     |     |     | 640 |
| Asp | Tyr | Gln | Asn | Asp | Leu | Arg | Val | Ser | Gln | Thr | Phe | Phe | Ile | Gln | Thr |
|     |     |     |     | 645 |     |     |     |     | 650 |     |     |     |     | 655 |     |
| Glu | Gln | His | Tyr | Lys | Lys | Phe | Arg | Asn | Thr | Leu | Lys | Phe | Leu | Leu | Ala |
|     |     |     | 660 |     |     |     |     | 665 |     |     |     | 670 |     |     |     |
| Asn | Phe | Ser | Asp | Met | Asp | Leu | Lys | Asn | Leu | Glu | Arg | Ser | His | Asp | Phe |
|     |     | 675 |     |     |     | 680 |     |     |     |     | 685 |     |     |     |     |
| Ser | Pro | Leu | Asp | His | Phe | Ile | Leu | Glu | Ala | Leu | Glu | Thr | Thr | Ser | Val |
|     | 690 |     |     |     |     | 695 |     |     |     |     | 700 |     |     |     |     |
| Gly | Val | Asn | Ser | Ala | Phe | Glu | Glu | His | Asp | Phe | Val | Lys | Gly | Leu | Asn |
| 705 |     |     |     |     | 710 |     |     |     |     | 715 |     |     |     |     | 720 |
| Ile | Leu | Met | Ala | Phe | Val | Thr | Asn | Glu | Leu | Ser | Gly | Ile | Tyr | Leu | Asp |
|     |     |     |     | 725 |     |     |     |     | 730 |     |     |     |     | 735 |     |
| Ala | Cys | Lys | Asp | Ser | Leu | Tyr | Cys | Asp | Ser | Lys | Asn | Asn | Glu | Lys | Arg |
|     |     |     | 740 |     |     |     |     | 745 |     |     |     |     | 750 |     |     |
| Gln | Ala | Ile | Gln | Met | Val | Leu | Leu | Ala | Val | Ala | Ser | Lys | Leu | Cys | Tyr |
|     |     | 755 |     |     |     |     | 760 |     |     |     |     | 765 |     |     |     |
| Phe | Leu | Ala | Pro | Ile | Leu | Thr | His | Thr | Ile | Glu | Glu | Val | Leu | Glu | His |
| 770 |     |     |     |     | 775 |     |     |     |     | 780 |     |     |     |     |     |
| Ser | Gln | Val | Leu | Cys | Ala | Phe | Leu | Gln | Ala | Lys | Asp | Val | Phe | Asp | Leu |
| 785 |     |     |     | 790 |     |     |     |     | 795 |     |     |     |     |     | 800 |
| Lys | Asp | Ile | Ser | Val | Ser | Glu | Lys | Leu | His | Leu | Lys | Glu | Phe | Lys | Lys |
|     |     |     | 805 |     |     |     |     | 810 |     |     |     |     | 815 |     |     |
| Pro | Glu | Asn | Phe | Glu | Ala | Val | Leu | Ala | Leu | Arg | Ser | Ala | Phe | Asn | Glu |
|     |     | 820 |     |     |     |     | 825 |     |     |     |     | 830 |     |     |     |
| Gln | Leu | Asp | Arg | Leu | Lys | Lys | Glu | Gly | Val | Ile | Lys | Asn | Ser | Leu | Glu |
|     | 835 |     |     |     |     | 840 |     |     |     |     | 845 |     |     |     |     |
| Cys | Ala | Ile | Glu | Val | Lys | Glu | Lys | Ala | Leu | Arg | Glu | Asn | Leu | Ile | Glu |
| 850 |     |     |     |     | 855 |     |     |     |     | 860 |     |     |     |     |     |
| Glu | Leu | Leu | Met | Val | Ser | Phe | Val | Gly | Val | Ala | Lys | Glu | Lys | Leu | Ser |
| 865 |     |     |     | 870 |     |     |     |     | 875 |     |     |     |     |     | 880 |
| Glu | Thr | Pro | Ala | Phe | Thr | Leu | Phe | Lys | Ala | Pro | Phe | Tyr | Lys | Cys | Pro |
|     |     |     |     | 885 |     |     |     |     | 890 |     |     |     |     | 895 |     |
| Arg | Cys | Trp | Arg | Phe | Lys | Ser | Glu | Leu | Glu | Asn | Thr | Pro | Cys | Lys | Arg |
|     |     |     | 900 |     |     |     |     | 905 |     |     |     |     | 910 |     |     |
| Cys | Glu | Glu | Val | Leu | Lys | Glu | Arg |     |     |     |     |     |     |     |     |
|     |     | 915 |     |     |     |     | 920 |     |     |     |     |     |     |     |     |

( 2 ) INFORMATION FOR SEQ ID NO:3:

( i ) SEQUENCE CHARACTERISTICS:
        ( A ) LENGTH: 2157 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 102..2045

( x i ) SEQUENCE DESCRIPTION: SEQ ID NO:3:

```
ACCCCACAAA TAAGCATAAA TTCAACCTCT ATTCTCTAAA TTTTAAAAG CATGTTAAAA            60

TTAAGAGATT TAAACAAATT TAAGGTAACA CGATTATAAA G ATG CAA AAA TCA             113
                                             Met Gln Lys Ser
                                              1

CTG ATC ACA ACC CCC ATT TAT TAT GTG AAT GAT ATT CCC CAT ATT GGC            161
Leu Ile Thr Thr Pro Ile Tyr Tyr Val Asn Asp Ile Pro His Ile Gly
 5              10                  15                  20

CAT GCT TAT ACG ACT TTG ATT GCG GAC ACT TTA AAG AAG TAT TAC ACG            209
His Ala Tyr Thr Thr Leu Ile Ala Asp Thr Leu Lys Lys Tyr Tyr Thr
                25                  30                  35

CTT CAA GGC GAA GAA GTC TTT TTT TTA ACC GGC ACC GAT GAG CAT GGG            257
Leu Gln Gly Glu Glu Val Phe Phe Leu Thr Gly Thr Asp Glu His Gly
        40                  45                  50

CAA AAG ATC GAA CAA AGC GCG AGA TTG AGA AAT CAA AGC CCT AAA GCT            305
Gln Lys Ile Glu Gln Ser Ala Arg Leu Arg Asn Gln Ser Pro Lys Ala
         55                  60                  65

TAC GCC GAT AGC ATT AGC GCG ATT TTT AAA GAC CAG TGG GAT TTT TTC            353
Tyr Ala Asp Ser Ile Ser Ala Ile Phe Lys Asp Gln Trp Asp Phe Phe
 70                  75                  80

AAT TTG GAT TAT GAT GGT TTT ATC CGC ACC ACA GAC AGC GAG CAT CAA            401
Asn Leu Asp Tyr Asp Gly Phe Ile Arg Thr Thr Asp Ser Glu His Gln
 85                  90                  95                 100

AAA TGC GTG CAA AAC GCC TTT GAA ATC ATG TTT GAA AAA GGG GAT ATT            449
Lys Cys Val Gln Asn Ala Phe Glu Ile Met Phe Glu Lys Gly Asp Ile
                105                 110                 115

TAT AAA GGC GCT TAT AGT GGG TAT TAT TGC GTG AGC TGT GAG AGT TAT            497
Tyr Lys Gly Ala Tyr Ser Gly Tyr Tyr Cys Val Ser Cys Glu Ser Tyr
                120                 125                 130

TGC GCG ATT TCT AAA GCG GAC AAT ACG AGT GAT AAA GTC CTA TGC CCT            545
Cys Ala Ile Ser Lys Ala Asp Asn Thr Ser Asp Lys Val Leu Cys Pro
         135                 140                 145

GAT TGC TTG AGG GAG ACT GCG CTT TTA GAA GAA GAG AGT TAT TTT TTT            593
Asp Cys Leu Arg Glu Thr Ala Leu Leu Glu Glu Glu Ser Tyr Phe Phe
 150                 155                 160

AAA TTG AGC GCG TAT GAG AAG CCT TTA TTG GAG TTT TAC GCC AAA AAC            641
Lys Leu Ser Ala Tyr Glu Lys Pro Leu Leu Glu Phe Tyr Ala Lys Asn
 165                 170                 175                 180

CCT GAA GCG ATT TTG CCT ATT TAT CGT AAA AAT GAG GTA ACT TCT TTT            689
Pro Glu Ala Ile Leu Pro Ile Tyr Arg Lys Asn Glu Val Thr Ser Phe
                185                 190                 195

ATT GAG CAG GGT TTA TTG GAT CTG TCT ATC ACG CGC ACG AGC TTT GAA            737
Ile Glu Gln Gly Leu Leu Asp Leu Ser Ile Thr Arg Thr Ser Phe Glu
                200                 205                 210

TGG GGC ATT CCT TTG CCT AAA AAA ATG AAC GAT CCT AAA CAT GTG GTG            785
Trp Gly Ile Pro Leu Pro Lys Lys Met Asn Asp Pro Lys His Val Val
         215                 220                 225

TAT GTT TGG CTA GAC GCT TTA TTG AAT TAT GCG AGC GCG TTA GGG TAT            833
Tyr Val Trp Leu Asp Ala Leu Leu Asn Tyr Ala Ser Ala Leu Gly Tyr
 230                 235                 240
```

```
TTG AAT GGT TTA GAC AAT AAA ATG GCG CAT TTT GAA TGC GCT AGG CAT        881
Leu Asn Gly Leu Asp Asn Lys Met Ala His Phe Glu Cys Ala Arg His
245             250                 255                 260

ATT GTG GGT AAG GAT ATT TTA CGC TTC CAT GCC ATT TAT TGG CCG GCT        929
Ile Val Gly Lys Asp Ile Leu Arg Phe His Ala Ile Tyr Trp Pro Ala
                265                 270                 275

TTT TTG ATG AGT TTG AAT TTG CCC CTA TTC AAA CAG CTT TGC GTG CAT        977
Phe Leu Met Ser Leu Asn Leu Pro Leu Phe Lys Gln Leu Cys Val His
            280                 285                 290

GGG TGG TGG ACG ATA GAG GGC GTG AAA ATG AGT AAG AGC TTG GGT AAT       1025
Gly Trp Trp Thr Ile Glu Gly Val Lys Met Ser Lys Ser Leu Gly Asn
        295                 300                 305

GTT TTA GAC GCT CAA AAG CTC GCT ATG GAG TAT GGG ATT GAA GAA TTA       1073
Val Leu Asp Ala Gln Lys Leu Ala Met Glu Tyr Gly Ile Glu Glu Leu
310                 315                 320

CGC TAT TTT TTA TTG CGT GAG GTG CCT TTT GGG CAA GAT GGG GAT TTT       1121
Arg Tyr Phe Leu Leu Arg Glu Val Pro Phe Gly Gln Asp Gly Asp Phe
325                 330                 335                 340

TCT AAA AAA GCG TTA ATA GAA AGG ATC AAC GCG AAT TTG AAC AAC GAT       1169
Ser Lys Lys Ala Leu Ile Glu Arg Ile Asn Ala Asn Leu Asn Asn Asp
                345                 350                 355

TTG GGG AAT TTG TTG AAT CGC TTG CTA GGC ATG GCT AAA AAA TAT TTC       1217
Leu Gly Asn Leu Leu Asn Arg Leu Leu Gly Met Ala Lys Lys Tyr Phe
            360                 365                 370

AAT TAT TCT CTA AAA AGC GCC AAA ATC ACC GCG TAT TAT TCT AAA GAG       1265
Asn Tyr Ser Leu Lys Ser Ala Lys Ile Thr Ala Tyr Tyr Ser Lys Glu
        375                 380                 385

CTA GAA AAA GCG CAT CAA ATC TTA GAT AAC GCT AAT TCT TTT GTG CCT       1313
Leu Glu Lys Ala His Gln Ile Leu Asp Asn Ala Asn Ser Phe Val Pro
390                 395                 400

AAA ATG CAA TTG CAT AAA GCT TTA GAG GAA TTG TTT AAC GTT TAT GAT       1361
Lys Met Gln Leu His Lys Ala Leu Glu Glu Leu Phe Asn Val Tyr Asp
405                 410                 415                 420

TTT TTA AAC AAA CTC ATC GCT AAA GAA GAG CCG TGG GTT TTG CAC AAA       1409
Phe Leu Asn Lys Leu Ile Ala Lys Glu Glu Pro Trp Val Leu His Lys
                425                 430                 435

AAC AAC GAA TCA GAA AAA CTA GAA GCC TTG TTG AGT TTG ATC GCA AAC       1457
Asn Asn Glu Ser Glu Lys Leu Glu Ala Leu Leu Ser Leu Ile Ala Asn
            440                 445                 450

GCG CTT TTG CAA TCA AGC TTT TTG CTC TAT GCG TTC ATG CCA AAG AGT       1505
Ala Leu Leu Gln Ser Ser Phe Leu Leu Tyr Ala Phe Met Pro Lys Ser
        455                 460                 465

GCT GTG AAA TTA GCG AGC GCT TTC AAC ACA GAA ATC ACG CCC AAT AAT       1553
Ala Val Lys Leu Ala Ser Ala Phe Asn Thr Glu Ile Thr Pro Asn Asn
470                 475                 480

TAC GAA CGC TTT TTT AAG GCC AAA AAA TTA CAA GAT ATG GTT TTA CAA       1601
Tyr Glu Arg Phe Phe Lys Ala Lys Lys Leu Gln Asp Met Val Leu Gln
485                 490                 495                 500

GAC ACC GAG CCT TTA TTT TGT AAA ATG GAG AAA ATT GAA AAG ACT GAC       1649
Asp Thr Glu Pro Leu Phe Cys Lys Met Glu Lys Ile Glu Lys Thr Asp
                505                 510                 515

AAA AGG GAA AAA GAA GTC CCA CCA GAA AAA GCA GAA AAA AAA GAA AAA       1697
Lys Arg Glu Lys Glu Val Pro Pro Glu Lys Ala Glu Lys Lys Glu Lys
            520                 525                 530

GAA AAA GCC CCA CCA AAA CAA GAA AAC TAT ATC GGC ATT GAG GAT TTC       1745
Glu Lys Ala Pro Pro Lys Gln Glu Asn Tyr Ile Gly Ile Glu Asp Phe
        535                 540                 545

AAA AAA GTA GAA ATT AAA GTA GGG CTT ATC AAA GAA GCT CAA AGG ATT       1793
Lys Lys Val Glu Ile Lys Val Gly Leu Ile Lys Glu Ala Gln Arg Ile
550                 555                 560
```

-continued

```
GAA AAA TCC AAT AAA TTA TTG CGC TTA AAA GTG GAT TTA GGC GAA AAT      1841
Glu Lys Ser Asn Lys Leu Leu Arg Leu Lys Val Asp Leu Gly Glu Asn
565             570                 575                 580

CGT TTG AGG CAG ATC ATC TCA GGG ATC GCT TTG GAT TAT GAG CCT GAA      1889
Arg Leu Arg Gln Ile Ile Ser Gly Ile Ala Leu Asp Tyr Glu Pro Glu
                    585                 590                 595

AGT TTG GTG GGG CAA ATG GTG TGC GTG GTG GCT AAT TTA AAG CCT GCA      1937
Ser Leu Val Gly Gln Met Val Cys Val Val Ala Asn Leu Lys Pro Ala
                600                 605                 610

AAG CTT ATG GGC GAA ATG AGT GAG GGC ATG ATT TTA GCG GTG CGA GAT      1985
Lys Leu Met Gly Glu Met Ser Glu Gly Met Ile Leu Ala Val Arg Asp
            615                 620                 625

AGC GAT AAT CTG GCT TTA ATC AGC CCT ACC AAA GAA AAA ATC GCA GGA      2033
Ser Asp Asn Leu Ala Leu Ile Ser Pro Thr Lys Glu Lys Ile Ala Gly
630                 635                 640

AGT TTG ATC AGC TAAATGCGAT TAGGGGTGAA TGAAGCCGTA GAATTGAGTT          2085
Ser Leu Ile Ser
645

TGGGCGAATT GCAAAACACG CCCTCAATCA GCTATTTCAA TTCCATTGTC TTGTCTTTAA    2145

ACAAAGTCAA AA                                                        2157
```

( 2 ) INFORMATION FOR SEQ ID NO:4:

( i ) SEQUENCE CHARACTERISTICS:
      ( A ) LENGTH: 648 amino acids
      ( B ) TYPE: amino acid
      ( D ) TOPOLOGY: linear ( i i ) MOLECULE TYPE: protein ( x i ) SEQUENCE DESCRIPTION: SEQ ID NO:4:

```
Met Gln Lys Ser Leu Ile Thr Thr Pro Ile Tyr Tyr Val Asn Asp Ile
1               5                   10                  15

Pro His Ile Gly His Ala Tyr Thr Thr Leu Ile Ala Asp Thr Leu Lys
                20                  25                  30

Lys Tyr Tyr Thr Leu Gln Gly Glu Glu Val Phe Phe Leu Thr Gly Thr
            35                  40                  45

Asp Glu His Gly Gln Lys Ile Glu Gln Ser Ala Arg Leu Arg Asn Gln
50                  55                  60

Ser Pro Lys Ala Tyr Ala Asp Ser Ile Ser Ala Ile Phe Lys Asp Gln
65                  70                  75                  80

Trp Asp Phe Phe Asn Leu Asp Tyr Asp Gly Phe Ile Arg Thr Thr Asp
                85                  90                  95

Ser Glu His Gln Lys Cys Val Gln Asn Ala Phe Glu Ile Met Phe Glu
                100                 105                 110

Lys Gly Asp Ile Tyr Lys Gly Ala Tyr Ser Gly Tyr Tyr Cys Val Ser
            115                 120                 125

Cys Glu Ser Tyr Cys Ala Ile Ser Lys Ala Asp Asn Thr Ser Asp Lys
130                 135                 140

Val Leu Cys Pro Asp Cys Leu Arg Glu Thr Ala Leu Leu Glu Glu Glu
145                 150                 155                 160

Ser Tyr Phe Phe Lys Leu Ser Ala Tyr Glu Lys Pro Leu Leu Glu Phe
                165                 170                 175

Tyr Ala Lys Asn Pro Glu Ala Ile Leu Pro Ile Tyr Arg Lys Asn Glu
                180                 185                 190

Val Thr Ser Phe Ile Glu Gln Gly Leu Leu Asp Leu Ser Ile Thr Arg
            195                 200                 205
```

| Thr | Ser | Phe | Glu | Trp | Gly | Ile | Pro | Leu | Pro | Lys | Lys | Met | Asn | Asp | Pro |
|-----|-----|-----|-----|-----|-----|-----|-----|-----|-----|-----|-----|-----|-----|-----|-----|
| 210 |     |     |     |     | 215 |     |     |     |     | 220 |     |     |     |     |     |
| Lys | His | Val | Val | Tyr | Val | Trp | Leu | Asp | Ala | Leu | Asn | Tyr | Ala | Ser |
| 225 |     |     |     |     | 230 |     |     |     | 235 |     |     |     |     | 240 |
| Ala | Leu | Gly | Tyr | Leu | Asn | Gly | Leu | Asp | Asn | Lys | Met | Ala | His | Phe | Glu |
|     |     |     |     | 245 |     |     |     |     | 250 |     |     |     |     | 255 |     |
| Cys | Ala | Arg | His | Ile | Val | Gly | Lys | Asp | Ile | Leu | Arg | Phe | His | Ala | Ile |
|     |     |     | 260 |     |     |     |     | 265 |     |     |     |     | 270 |     |     |
| Tyr | Trp | Pro | Ala | Phe | Leu | Met | Ser | Leu | Asn | Leu | Pro | Leu | Phe | Lys | Gln |
|     |     | 275 |     |     |     |     | 280 |     |     |     |     | 285 |     |     |     |
| Leu | Cys | Val | His | Gly | Trp | Trp | Thr | Ile | Glu | Gly | Val | Lys | Met | Ser | Lys |
|     | 290 |     |     |     |     | 295 |     |     |     |     | 300 |     |     |     |     |
| Ser | Leu | Gly | Asn | Val | Leu | Asp | Ala | Gln | Lys | Leu | Ala | Met | Glu | Tyr | Gly |
| 305 |     |     |     |     | 310 |     |     |     |     | 315 |     |     |     |     | 320 |
| Ile | Glu | Glu | Leu | Arg | Tyr | Phe | Leu | Leu | Arg | Glu | Val | Pro | Phe | Gly | Gln |
|     |     |     |     | 325 |     |     |     |     | 330 |     |     |     |     | 335 |     |
| Asp | Gly | Asp | Phe | Ser | Lys | Lys | Ala | Leu | Ile | Glu | Arg | Ile | Asn | Ala | Asn |
|     |     |     | 340 |     |     |     |     | 345 |     |     |     |     | 350 |     |     |
| Leu | Asn | Asn | Asp | Leu | Gly | Asn | Leu | Leu | Asn | Arg | Leu | Leu | Gly | Met | Ala |
|     |     | 355 |     |     |     |     | 360 |     |     |     |     | 365 |     |     |     |
| Lys | Lys | Tyr | Phe | Asn | Tyr | Ser | Leu | Lys | Ser | Ala | Lys | Ile | Thr | Ala | Tyr |
|     | 370 |     |     |     |     | 375 |     |     |     |     | 380 |     |     |     |     |
| Tyr | Ser | Lys | Glu | Leu | Glu | Lys | Ala | His | Gln | Ile | Leu | Asp | Asn | Ala | Asn |
| 385 |     |     |     |     | 390 |     |     |     |     | 395 |     |     |     |     | 400 |
| Ser | Phe | Val | Pro | Lys | Met | Gln | Leu | His | Lys | Ala | Leu | Glu | Glu | Leu | Phe |
|     |     |     |     | 405 |     |     |     |     | 410 |     |     |     |     | 415 |     |
| Asn | Val | Tyr | Asp | Phe | Leu | Asn | Lys | Leu | Ile | Ala | Lys | Glu | Glu | Pro | Trp |
|     |     |     | 420 |     |     |     |     | 425 |     |     |     |     | 430 |     |     |
| Val | Leu | His | Lys | Asn | Asn | Glu | Ser | Glu | Lys | Leu | Glu | Ala | Leu | Leu | Ser |
|     |     |     | 435 |     |     |     |     | 440 |     |     |     |     | 445 |     |     |
| Leu | Ile | Ala | Asn | Ala | Leu | Leu | Gln | Ser | Ser | Phe | Leu | Leu | Tyr | Ala | Phe |
|     | 450 |     |     |     |     | 455 |     |     |     |     | 460 |     |     |     |     |
| Met | Pro | Lys | Ser | Ala | Val | Lys | Leu | Ala | Ser | Phe | Asn | Thr | Glu | Ile |
| 465 |     |     |     |     | 470 |     |     |     | 475 |     |     |     |     | 480 |
| Thr | Pro | Asn | Asn | Tyr | Glu | Arg | Phe | Phe | Lys | Ala | Lys | Lys | Leu | Gln | Asp |
|     |     |     |     | 485 |     |     |     |     | 490 |     |     |     |     | 495 |     |
| Met | Val | Leu | Gln | Asp | Thr | Glu | Pro | Leu | Phe | Cys | Lys | Met | Glu | Lys | Ile |
|     |     |     | 500 |     |     |     |     | 505 |     |     |     | 510 |     |     |     |
| Glu | Lys | Thr | Asp | Lys | Arg | Glu | Lys | Glu | Val | Pro | Pro | Glu | Lys | Ala | Glu |
|     |     | 515 |     |     |     |     | 520 |     |     |     |     | 525 |     |     |     |
| Lys | Lys | Glu | Lys | Glu | Lys | Ala | Pro | Pro | Lys | Gln | Glu | Asn | Tyr | Ile | Gly |
|     | 530 |     |     |     |     | 535 |     |     |     |     | 540 |     |     |     |     |
| Ile | Glu | Asp | Phe | Lys | Lys | Val | Glu | Ile | Lys | Val | Gly | Leu | Ile | Lys | Glu |
| 545 |     |     |     |     | 550 |     |     |     |     | 555 |     |     |     |     | 560 |
| Ala | Gln | Arg | Ile | Glu | Lys | Ser | Asn | Lys | Leu | Leu | Arg | Leu | Lys | Val | Asp |
|     |     |     |     | 565 |     |     |     |     | 570 |     |     |     |     | 575 |     |
| Leu | Gly | Glu | Asn | Arg | Leu | Arg | Gln | Ile | Ile | Ser | Gly | Ile | Ala | Leu | Asp |
|     |     |     | 580 |     |     |     |     | 585 |     |     |     |     | 590 |     |     |
| Tyr | Glu | Pro | Glu | Ser | Leu | Val | Gly | Gln | Met | Val | Cys | Val | Val | Ala | Asn |
|     |     | 595 |     |     |     |     | 600 |     |     |     |     | 605 |     |     |     |
| Leu | Lys | Pro | Ala | Lys | Leu | Met | Gly | Glu | Met | Ser | Glu | Gly | Met | Ile | Leu |
|     |     | 610 |     |     |     |     | 615 |     |     |     |     | 620 |     |     |     |
| Ala | Val | Arg | Asp | Ser | Asp | Asn | Leu | Ala | Leu | Ile | Ser | Pro | Thr | Lys | Glu |
| 625 |     |     |     |     | 630 |     |     |     |     | 635 |     |     |     |     | 640 |

```
Lys Ile Ala Gly Ser Leu Ile Ser
                645
```

( 2 ) INFORMATION FOR SEQ ID NO:5:

( i ) SEQUENCE CHARACTERISTICS:
        ( A ) LENGTH: 2662 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 153..2570

( x i ) SEQUENCE DESCRIPTION: SEQ ID NO:5:

```
CCTCATACCG GCGTTTGTGT TTTTACAGAT TTTAAATAAT TTGGTTACAG CTTACATGCT        60

CATGATTGGG GCTTTGATTA GTAACGCTTT CAGCCTCATC TTTTTGTTGA TTGAAAGCGT       120

TGTAACGAGC GAAACGGATT AAGGGGTAGT TG ATG GAT TTT ATC AAT ATA GAA        173
                                   Met Asp Phe Ile Asn Ile Glu
                                    1                   5

AAA AAA TGG CAA GAA TTT TGG TGG AAA AAT AAG AGT TTT GAG CCT AAA        221
Lys Lys Trp Gln Glu Phe Trp Trp Lys Asn Lys Ser Phe Glu Pro Lys
         10                  15                  20

GAC GAT TTT AAC CTC CCT AAA AAA TAC ATT CTG AGC ATG CTG CCT TAT        269
Asp Asp Phe Asn Leu Pro Lys Lys Tyr Ile Leu Ser Met Leu Pro Tyr
     25                  30                  35

CCT AGT GGG GAA ATC CAT ATG GGG CAT GTG CGC AAT TAC ACC ATT GGC        317
Pro Ser Gly Glu Ile His Met Gly His Val Arg Asn Tyr Thr Ile Gly
 40                  45                  50                  55

GAT GCT TTG GCG CGT TAT TAT CGT TTG CAC CAT TAT AAT GTG TTA CAC        365
Asp Ala Leu Ala Arg Tyr Tyr Arg Leu His His Tyr Asn Val Leu His
                 60                  65                  70

CCT ATG GGG TTT GAT TCT TTT GGG ATG CCT GCA GAA AAT GCG GCC ATT        413
Pro Met Gly Phe Asp Ser Phe Gly Met Pro Ala Glu Asn Ala Ala Ile
             75                  80                  85

AAG CAT GGT ATC CAC CCT AAA ACC TGG ACT TAT GAA AAC ATT GAA GCC        461
Lys His Gly Ile His Pro Lys Thr Trp Thr Tyr Glu Asn Ile Glu Ala
         90                  95                 100

ATG CAA AAA GAG TTT GAA GCT TTA GGG TTT TCT TTT TCT AAA AAC AGG        509
Met Gln Lys Glu Phe Glu Ala Leu Gly Phe Ser Phe Ser Lys Asn Arg
    105                 110                 115

GAA TTT GCC ACT TCA GAT CCG GAT TAC ACG AAA TTT GAG CAG CAA TTT        557
Glu Phe Ala Thr Ser Asp Pro Asp Tyr Thr Lys Phe Glu Gln Gln Phe
120                 125                 130                 135

TTC ATT GAT TTG TGG GAA AAA GGG TTA ATT TAT CGC AAG AAA GCC ATG        605
Phe Ile Asp Leu Trp Glu Lys Gly Leu Ile Tyr Arg Lys Lys Ala Met
                140                 145                 150

CTC AAT TGG TGC CCT AAC GAC AAG ACC GTT TTA GCT AAT GAG CAA GTC        653
Leu Asn Trp Cys Pro Asn Asp Lys Thr Val Leu Ala Asn Glu Gln Val
            155                 160                 165

ATC GAT GGG AGG TGT TGG CGT TGC GAT ACG GAA GTT GTT CAA AAA GAA        701
Ile Asp Gly Arg Cys Trp Arg Cys Asp Thr Glu Val Val Gln Lys Glu
        170                 175                 180

CTC TAT CAA TAT TAT TTG AAG ATC ACA AAC TAC GCT GAA GAA TTA CTA        749
Leu Tyr Gln Tyr Tyr Leu Lys Ile Thr Asn Tyr Ala Glu Glu Leu Leu
    185                 190                 195

AAA GAC TTA GAA ACT TTA GAA AAT CAT TGG CCT TCT CAA GTC CTA ACC        797
Lys Asp Leu Glu Thr Leu Glu Asn His Trp Pro Ser Gln Val Leu Thr
200                 205                 210                 215

ATG CAA AAA AAC TGG ATA GGA AAA TCT ATC GGG TTG CAA TTT GGT TTT        845
```

-continued

| | | | | | | | | | | | | | | |
|---|---|---|---|---|---|---|---|---|---|---|---|---|---|---|
| Met | Gln | Lys | Asn | Trp<br>220 | Ile | Gly | Lys | Ser<br>225 | Ile | Gly | Leu | Gln | Phe<br>230 | Gly | Phe |

| | | | | | | | | | | | | | | | |
|---|---|---|---|---|---|---|---|---|---|---|---|---|---|---|---|
| AAA | ATC | GCT | GAT | GAG | TGC | TTG | AAG | GCT | TGC | AAC | GGC | ATT | CAA | GAA | ATT | 893 |
| Lys | Ile | Ala | Asp<br>235 | Glu | Cys | Leu | Lys | Ala<br>240 | Cys | Asn | Gly | Ile | Gln<br>245 | Glu | Ile |
| GAA | GTT | TTT | ACC | ACA | AGA | GCG | GAC | ACC | ATT | TAT | GGC | GTC | ACT | TAC | ATC | 941 |
| Glu | Val | Phe<br>250 | Thr | Thr | Arg | Ala | Asp<br>255 | Thr | Ile | Tyr | Gly | Val<br>260 | Thr | Tyr | Ile |
| GCC | ATC | GCC | CCA | GAA | CAC | CCT | TTA | GTA | GAG | CAT | GCC | ATT | AAG | CGA | GTG | 989 |
| Ala | Ile<br>265 | Ala | Pro | Glu | His | Pro<br>270 | Leu | Val | Glu | His | Ala<br>275 | Ile | Lys | Arg | Val |
| AGC | CAA | GAA | GAT | TCA | AAG | ATC | ATT | AAA | GCG | ATT | TTA | AAC | ACG | ACT | CAA | 1037 |
| Ser<br>280 | Gln | Glu | Asp | Ser | Lys<br>285 | Ile | Ile | Lys | Ala | Ile<br>290 | Leu | Asn | Thr | Thr | Gln<br>295 |
| AGA | GAA | AGA | GCT | TTA | GAG | AAA | AAA | GGG | GCG | TTT | TTA | GGC | GTT | TAT | GCT | 1085 |
| Arg | Glu | Arg | Ala | Leu<br>300 | Glu | Lys | Lys | Gly | Ala<br>305 | Phe | Leu | Gly | Val | Tyr<br>310 | Ala |
| ATC | CAC | CCT | TTA | ACA | AAG | CAA | AAA | ATC | CCT | GTT | TGG | GTG | GCT | AAT | TTC | 1133 |
| Ile | His | Pro | Leu<br>315 | Thr | Lys | Gln | Lys | Ile<br>320 | Pro | Val | Trp | Val | Ala<br>325 | Asn | Phe |
| GCC | TTA | GCT | AAT | TAT | GGC | TCT | GGG | GCG | TTA | ATG | GGC | GTG | CCA | GCC | TGC | 1181 |
| Ala | Leu | Ala<br>330 | Asn | Tyr | Gly | Ser | Gly<br>335 | Ala | Leu | Met | Gly | Val<br>340 | Pro | Ala | Cys |
| GAT | GAA | AGG | GAT | TTT | GAA | TTC | GCC | AAT | CTT | TAT | CAT | ATC | CCT | ATT | AAA | 1229 |
| Asp | Glu<br>345 | Arg | Asp | Phe | Glu | Phe<br>350 | Ala | Asn | Leu | Tyr | His<br>355 | Ile | Pro | Ile | Lys |
| GTG | ATC | ACT | CAA | AGC | CCT | CAA | AAT | TTG | CCC | CAC | ACC | AAA | GAA | GAG | GTT | 1277 |
| Val<br>360 | Ile | Thr | Gln | Ser | Pro<br>365 | Gln | Asn | Leu | Pro | His<br>370 | Thr | Lys | Glu | Glu | Val<br>375 |
| TTA | AAA | AAT | AGC | GGG | GAG | TGG | AGC | GAT | CTT | TCT | AGC | TCA | GTG | GCC | AGA | 1325 |
| Leu | Lys | Asn | Ser | Gly<br>380 | Glu | Trp | Ser | Asp | Leu<br>385 | Ser | Ser | Ser | Val | Ala<br>390 | Arg |
| GAG | CAA | ATC | ATC | GCT | TAT | TTT | GAA | AAA | GAA | AAC | CTC | GGT | AAA | AGG | GTG | 1373 |
| Glu | Gln | Ile | Ile<br>395 | Ala | Tyr | Phe | Glu | Lys<br>400 | Glu | Asn | Leu | Gly | Lys<br>405 | Arg | Val |
| ATC | AAC | TAC | CGT | TTG | CAA | GAT | TGG | GGA | GTG | AGC | CGT | CAA | AGG | TAT | TGG | 1421 |
| Ile | Asn | Tyr | Arg<br>410 | Leu | Gln | Asp | Trp | Gly<br>415 | Val | Ser | Arg | Gln | Arg<br>420 | Tyr | Trp |
| GGA | GCG | CCC | ATT | CCT | ATG | ATT | CAT | TGC | AAC | AAT | TGC | GGG | ATT | GTT | CCT | 1469 |
| Gly | Ala | Pro<br>425 | Ile | Pro | Met | Ile<br>430 | His | Cys | Asn | Asn | Cys<br>435 | Gly | Ile | Val | Pro |
| GAA | ACC | CAA | CTG | CCG | GTA | ACT | TTA | CCC | GAA | GAC | ATT | GTG | ATT | GAT | GGG | 1517 |
| Glu<br>440 | Thr | Gln | Leu | Pro | Val<br>445 | Thr | Leu | Pro | Glu | Asp<br>450 | Ile | Val | Ile | Asp | Gly<br>455 |
| GAG | GGC | AAT | CCG | TTA | GAA | AAG | CAT | GTG | AGT | TGG | AAA | TTC | GCT | CAA | TGC | 1565 |
| Glu | Gly | Asn | Pro | Leu<br>460 | Glu | Lys | His | Val | Ser<br>465 | Trp | Lys | Phe | Ala | Gln<br>470 | Cys |
| CCC | AAA | TGC | CAC | AAA | GAC | GCT | TTA | AGA | GAA | ACA | GAC | ACC | ATG | GAT | ACT | 1613 |
| Pro | Lys | Cys | His<br>475 | Lys | Asp | Ala | Leu | Arg<br>480 | Glu | Thr | Asp | Thr | Met<br>485 | Asp | Thr |
| TTC | ATC | CAG | TCT | AGT | TGG | TAT | TTC | TTG | CGC | TAC | ACC | ACC | CCC | AAA | AAT | 1661 |
| Phe | Ile | Gln<br>490 | Ser | Ser | Trp | Tyr | Phe<br>495 | Leu | Arg | Tyr | Thr | Thr<br>500 | Pro | Lys | Asn |
| CAG | CGT | GAA | AAT | CAA | GCG | TTT | GAT | CAA | AAT | TAC | TTG | AAG | TAT | TTC | ATG | 1709 |
| Gln | Arg | Glu<br>505 | Asn | Gln | Ala | Phe | Asp<br>510 | Gln | Asn | Tyr | Leu | Lys<br>515 | Tyr | Phe | Met |
| CCA | GTG | GAT | ACT | TAT | ATT | GGC | GGC | ATT | GAA | CAT | GCG | ATT | TTG | CAC | TTG | 1757 |
| Pro<br>520 | Val | Asp | Thr | Tyr | Ile<br>525 | Gly | Gly | Ile | Glu | His<br>530 | Ala | Ile | Leu | His | Leu<br>535 |
| TTA | TAC | GCG | CGC | TTT | TTC | ACT | AAG | GCT | TTA | AGG | GAT | TTG | GGC | TAT | ATT | 1805 |

```
Leu Tyr Ala Arg Phe Phe Thr Lys Ala Leu Arg Asp Leu Gly Tyr Ile
            540             545                 550

CAT TTA GAT GAG CCT TTC AAA CAG CTT ATC ACT CAA GGC ATG GTC TTA    1853
His Leu Asp Glu Pro Phe Lys Gln Leu Ile Thr Gln Gly Met Val Leu
            555             560                 565

AAA AAT GGC ACT AAG ATG AGC AAA TCT AAA GGT AAT GTC GTT AGC CCT    1901
Lys Asn Gly Thr Lys Met Ser Lys Ser Lys Gly Asn Val Val Ser Pro
            570             575                 580

AAA GAA ATA CTC AAA AAA TAC GGG GCC GAT GCC GCA AGG CTT TTT ATC    1949
Lys Glu Ile Leu Lys Lys Tyr Gly Ala Asp Ala Ala Arg Leu Phe Ile
    585             590                 595

CTT TTT GCT GCC CCA CCG GCT AAA GAA TTA GAA TGG AAT GAC AGC GCT    1997
Leu Phe Ala Ala Pro Pro Ala Lys Glu Leu Glu Trp Asn Asp Ser Ala
600             605             610                 615

TTA GAA GGT GCG CAC CGG TTT ATC AAG CGC TTA TAC GAT AAA GCG AGT    2045
Leu Glu Gly Ala His Arg Phe Ile Lys Arg Leu Tyr Asp Lys Ala Ser
                620             625                 630

GCC ATT ACC CCT ACC ACT TCT AAG CCT GAA TTT AAA GAA GTC AGC CTG    2093
Ala Ile Thr Pro Thr Thr Ser Lys Pro Glu Phe Lys Glu Val Ser Leu
            635             640                 645

AAT GAA GCG CAA AAA CTA GCT CGT AAA AAA GTC TAT GAA GCG TTA AAA    2141
Asn Glu Ala Gln Lys Leu Ala Arg Lys Lys Val Tyr Glu Ala Leu Lys
        650             655                 660

AAA TCG CAT GAA ATT TTC AAT AAG GCT GAA AGC GCT TAC GCG TTT AAC    2189
Lys Ser His Glu Ile Phe Asn Lys Ala Glu Ser Ala Tyr Ala Phe Asn
        665             670                 675

ACT TTG ATC GCA AGT TGC ATG GAG GCT TTA AAC GCT TTG AGT GCG CAA    2237
Thr Leu Ile Ala Ser Cys Met Glu Ala Leu Asn Ala Leu Ser Ala Gln
680             685             690                 695

ACT AAT GAG CAA ATT TTA TGC GAA GGT TAT TTT GTG TTG TTG CAA ATT    2285
Thr Asn Glu Gln Ile Leu Cys Glu Gly Tyr Phe Val Leu Leu Gln Ile
            700             705                 710

TTA GAG CCT ATT ATC CCG CAC ACC GCA TGG GAG TTG AGT GAG AGG CTT    2333
Leu Glu Pro Ile Ile Pro His Thr Ala Trp Glu Leu Ser Glu Arg Leu
            715             720                 725

TTT AAA AGA GAG AAT TTT AAG CCT ATA GCG ATC GAT GAA AGC GCT TTG    2381
Phe Lys Arg Glu Asn Phe Lys Pro Ile Ala Ile Asp Glu Ser Ala Leu
        730             735                 740

ATG GAA GAC TTT ATG ACT TTA GGG CTT ACC ATT AAT GGC AAA AGG CGC    2429
Met Glu Asp Phe Met Thr Leu Gly Leu Thr Ile Asn Gly Lys Arg Arg
    745             750                 755

GCG GAA TTG AAA GTC AAT ATT AAC GCC AGT AAA GAA GAA ATT ATT GTT    2477
Ala Glu Leu Lys Val Asn Ile Asn Ala Ser Lys Glu Glu Ile Ile Val
760             765             770                 775

TTG GCT AAA AAA GAA TTA GAG AAA TAT TTA GAA AAG GCG AGC GTT AAA    2525
Leu Ala Lys Lys Glu Leu Glu Lys Tyr Leu Glu Lys Ala Ser Val Lys
            780             785                 790

AAA GAA ATT TAT GTG CCT AAT AAG CTC GTT AAT TTT GTT ATC GCA         2570
Lys Glu Ile Tyr Val Pro Asn Lys Leu Val Asn Phe Val Ile Ala
            795             800                 805

TGAAAGCTTT ACTTTTTTTT ATTTGTTGC TTTTGTTCAA GGGCTGTGGG TATAAGCCCA    2630

TCGCCGCTTA CGCTCAAAAC GCTTTAGGCG AT                                2662
```

( 2 ) INFORMATION FOR SEQ ID NO:6:

( i ) SEQUENCE CHARACTERISTICS:
        ( A ) LENGTH: 806 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Asp | Phe | Ile | Asn | Ile | Glu | Lys | Lys | Trp | Gln | Glu | Phe | Trp | Trp | Lys |
|---|---|---|---|---|---|---|---|---|---|---|---|---|---|---|---|
| 1 | | | | 5 | | | | | 10 | | | | | 15 | |

| Asn | Lys | Ser | Phe | Glu | Pro | Lys | Asp | Asp | Phe | Asn | Leu | Pro | Lys | Lys | Tyr |
|---|---|---|---|---|---|---|---|---|---|---|---|---|---|---|---|
| | | | | 20 | | | | 25 | | | | | 30 | | |

| Ile | Leu | Ser | Met | Leu | Pro | Tyr | Pro | Ser | Gly | Glu | Ile | His | Met | Gly | His |
|---|---|---|---|---|---|---|---|---|---|---|---|---|---|---|---|
| | | | 35 | | | | 40 | | | | | 45 | | | |

| Val | Arg | Asn | Tyr | Thr | Ile | Gly | Asp | Ala | Leu | Ala | Arg | Tyr | Tyr | Arg | Leu |
|---|---|---|---|---|---|---|---|---|---|---|---|---|---|---|---|
| | 50 | | | | | 55 | | | | | 60 | | | | |

| His | His | Tyr | Asn | Val | Leu | His | Pro | Met | Gly | Phe | Asp | Ser | Phe | Gly | Met |
|---|---|---|---|---|---|---|---|---|---|---|---|---|---|---|---|
| 65 | | | | | 70 | | | | | 75 | | | | | 80 |

| Pro | Ala | Glu | Asn | Ala | Ala | Ile | Lys | His | Gly | Ile | His | Pro | Lys | Thr | Trp |
|---|---|---|---|---|---|---|---|---|---|---|---|---|---|---|---|
| | | | | | 85 | | | | | 90 | | | | 95 | |

| Thr | Tyr | Glu | Asn | Ile | Glu | Ala | Met | Gln | Lys | Glu | Phe | Glu | Ala | Leu | Gly |
|---|---|---|---|---|---|---|---|---|---|---|---|---|---|---|---|
| | | | 100 | | | | | 105 | | | | | 110 | | |

| Phe | Ser | Phe | Ser | Lys | Asn | Arg | Glu | Phe | Ala | Thr | Ser | Asp | Pro | Asp | Tyr |
|---|---|---|---|---|---|---|---|---|---|---|---|---|---|---|---|
| | | | 115 | | | | 120 | | | | | 125 | | | |

| Thr | Lys | Phe | Glu | Gln | Gln | Phe | Phe | Ile | Asp | Leu | Trp | Glu | Lys | Gly | Leu |
|---|---|---|---|---|---|---|---|---|---|---|---|---|---|---|---|
| | 130 | | | | | 135 | | | | | 140 | | | | |

| Ile | Tyr | Arg | Lys | Lys | Ala | Met | Leu | Asn | Trp | Cys | Pro | Asn | Asp | Lys | Thr |
|---|---|---|---|---|---|---|---|---|---|---|---|---|---|---|---|
| 145 | | | | | 150 | | | | | 155 | | | | | 160 |

| Val | Leu | Ala | Asn | Glu | Gln | Val | Ile | Asp | Gly | Arg | Cys | Trp | Arg | Cys | Asp |
|---|---|---|---|---|---|---|---|---|---|---|---|---|---|---|---|
| | | | | 165 | | | | | 170 | | | | | 175 | |

| Thr | Glu | Val | Val | Gln | Lys | Glu | Leu | Tyr | Gln | Tyr | Leu | Lys | Ile | Thr |
|---|---|---|---|---|---|---|---|---|---|---|---|---|---|---|
| | | | 180 | | | | | 185 | | | | | 190 | |

| Asn | Tyr | Ala | Glu | Glu | Leu | Leu | Lys | Asp | Leu | Glu | Thr | Leu | Glu | Asn | His |
|---|---|---|---|---|---|---|---|---|---|---|---|---|---|---|---|
| | | 195 | | | | | 200 | | | | | 205 | | | |

| Trp | Pro | Ser | Gln | Val | Leu | Thr | Met | Gln | Lys | Asn | Trp | Ile | Gly | Lys | Ser |
|---|---|---|---|---|---|---|---|---|---|---|---|---|---|---|---|
| | 210 | | | | | 215 | | | | | 220 | | | | |

| Ile | Gly | Leu | Gln | Phe | Gly | Phe | Lys | Ile | Ala | Asp | Glu | Cys | Leu | Lys | Ala |
|---|---|---|---|---|---|---|---|---|---|---|---|---|---|---|---|
| 225 | | | | | 230 | | | | | 235 | | | | | 240 |

| Cys | Asn | Gly | Ile | Gln | Glu | Ile | Glu | Val | Phe | Thr | Thr | Arg | Ala | Asp | Thr |
|---|---|---|---|---|---|---|---|---|---|---|---|---|---|---|---|
| | | | | 245 | | | | | 250 | | | | | 255 | |

| Ile | Tyr | Gly | Val | Thr | Tyr | Ile | Ala | Ile | Ala | Pro | Glu | His | Pro | Leu | Val |
|---|---|---|---|---|---|---|---|---|---|---|---|---|---|---|---|
| | | | 260 | | | | | 265 | | | | | 270 | | |

| Glu | His | Ala | Ile | Lys | Arg | Val | Ser | Gln | Glu | Asp | Ser | Lys | Ile | Ile | Lys |
|---|---|---|---|---|---|---|---|---|---|---|---|---|---|---|---|
| | | 275 | | | | | 280 | | | | | 285 | | | |

| Ala | Ile | Leu | Asn | Thr | Thr | Gln | Arg | Glu | Arg | Ala | Leu | Glu | Lys | Lys | Gly |
|---|---|---|---|---|---|---|---|---|---|---|---|---|---|---|---|
| | 290 | | | | | 295 | | | | | 300 | | | | |

| Ala | Phe | Leu | Gly | Val | Tyr | Ala | Ile | His | Pro | Leu | Thr | Lys | Gln | Lys | Ile |
|---|---|---|---|---|---|---|---|---|---|---|---|---|---|---|---|
| 305 | | | | | 310 | | | | | 315 | | | | | 320 |

| Pro | Val | Trp | Val | Ala | Asn | Phe | Ala | Leu | Ala | Asn | Tyr | Gly | Ser | Gly | Ala |
|---|---|---|---|---|---|---|---|---|---|---|---|---|---|---|---|
| | | | | 325 | | | | | 330 | | | | | 335 | |

| Leu | Met | Gly | Val | Pro | Ala | Cys | Asp | Glu | Arg | Asp | Phe | Glu | Phe | Ala | Asn |
|---|---|---|---|---|---|---|---|---|---|---|---|---|---|---|---|
| | | | 340 | | | | | 345 | | | | | 350 | | |

| Leu | Tyr | His | Ile | Pro | Ile | Lys | Val | Ile | Thr | Gln | Ser | Pro | Gln | Asn | Leu |
|---|---|---|---|---|---|---|---|---|---|---|---|---|---|---|---|
| | | 355 | | | | | 360 | | | | | 365 | | | |

| Pro | His | Thr | Lys | Glu | Glu | Val | Leu | Lys | Asn | Ser | Gly | Glu | Trp | Ser | Asp |
|---|---|---|---|---|---|---|---|---|---|---|---|---|---|---|---|
| | 370 | | | | | 375 | | | | | 380 | | | | |

| Leu | Ser | Ser | Ser | Val | Ala | Arg | Glu | Gln | Ile | Ile | Ala | Tyr | Phe | Glu | Lys |
|---|---|---|---|---|---|---|---|---|---|---|---|---|---|---|---|
| 385 | | | | | 390 | | | | | 395 | | | | | 400 |

| Glu | Asn | Leu | Gly | Lys | Arg | Val | Ile | Asn | Tyr | Arg | Leu | Gln | Asp | Trp | Gly |
|---|---|---|---|---|---|---|---|---|---|---|---|---|---|---|---|
| | | | | 405 | | | | | 410 | | | | | 415 | |

-continued

| | | | | | | | | | | | | | |
|---|---|---|---|---|---|---|---|---|---|---|---|---|---|
| Val | Ser | Arg | Gln 420 | Arg | Tyr | Trp | Gly | Ala 425 | Ile | Pro | Met | Ile 430 | His | Cys |
| Asn | Asn | Cys 435 | Gly | Ile | Val | Pro | Glu 440 | Thr | Gln | Leu | Pro | Val 445 | Thr | Leu | Pro |
| Glu | Asp 450 | Ile | Val | Ile | Asp | Gly 455 | Glu | Gly | Asn | Pro | Leu 460 | Glu | Lys | His | Val |
| Ser 465 | Trp | Lys | Phe | Ala | Gln 470 | Cys | Pro | Lys | Cys | His 475 | Lys | Asp | Ala | Leu | Arg 480 |
| Glu | Thr | Asp | Thr | Met 485 | Asp | Thr | Phe | Ile | Gln 490 | Ser | Ser | Trp | Tyr | Phe 495 | Leu |
| Arg | Tyr | Thr | Thr 500 | Pro | Lys | Asn | Gln | Arg 505 | Glu | Asn | Gln | Ala | Phe 510 | Asp | Gln |
| Asn | Tyr | Leu 515 | Lys | Tyr | Phe | Met | Pro 520 | Val | Asp | Thr | Tyr | Ile 525 | Gly | Gly | Ile |
| Glu | His 530 | Ala | Ile | Leu | His | Leu 535 | Leu | Tyr | Ala | Arg | Phe 540 | Phe | Thr | Lys | Ala |
| Leu 545 | Arg | Asp | Leu | Gly | Tyr 550 | Ile | His | Leu | Asp | Glu 555 | Pro | Phe | Lys | Gln | Leu 560 |
| Ile | Thr | Gln | Gly | Met 565 | Val | Leu | Lys | Asn | Gly 570 | Thr | Lys | Met | Ser | Lys 575 | Ser |
| Lys | Gly | Asn | Val 580 | Val | Ser | Pro | Lys | Glu 585 | Ile | Leu | Lys | Lys | Tyr 590 | Gly | Ala |
| Asp | Ala | Ala 595 | Arg | Leu | Phe | Ile | Leu 600 | Phe | Ala | Ala | Pro | Pro 605 | Ala | Lys | Glu |
| Leu | Glu 610 | Trp | Asn | Asp | Ser | Ala 615 | Leu | Glu | Gly | Ala | His 620 | Arg | Phe | Ile | Lys |
| Arg 625 | Leu | Tyr | Asp | Lys | Ala 630 | Ser | Ala | Ile | Thr | Pro 635 | Thr | Thr | Ser | Lys | Pro 640 |
| Glu | Phe | Lys | Glu | Val 645 | Ser | Leu | Asn | Glu | Ala 650 | Gln | Lys | Leu | Ala | Arg 655 | Lys |
| Lys | Val | Tyr | Glu 660 | Ala | Leu | Lys | Lys | Ser 665 | His | Glu | Ile | Phe | Asn 670 | Lys | Ala |
| Glu | Ser | Ala 675 | Tyr | Ala | Phe | Asn | Thr 680 | Leu | Ile | Ala | Ser | Cys 685 | Met | Glu | Ala |
| Leu | Asn 690 | Ala | Leu | Ser | Ala | Gln 695 | Thr | Asn | Glu | Gln | Ile 700 | Leu | Cys | Glu | Gly |
| Tyr 705 | Phe | Val | Leu | Leu | Gln 710 | Ile | Leu | Glu | Pro | Ile 715 | Ile | Pro | His | Thr | Ala 720 |
| Trp | Glu | Leu | Ser | Glu 725 | Arg | Leu | Phe | Lys | Arg 730 | Glu | Asn | Phe | Lys | Pro 735 | Ile |
| Ala | Ile | Asp | Glu 740 | Ser | Ala | Leu | Met | Glu 745 | Asp | Phe | Met | Thr | Leu 750 | Gly | Leu |
| Thr | Ile | Asn 755 | Gly | Lys | Arg | Arg | Ala 760 | Glu | Leu | Lys | Val | Asn 765 | Ile | Asn | Ala |
| Ser | Lys 770 | Glu | Glu | Ile | Ile | Val 775 | Leu | Ala | Lys | Lys | Glu 780 | Leu | Glu | Lys | Tyr |
| Leu 785 | Glu | Lys | Ala | Ser | Val 790 | Lys | Lys | Glu | Ile | Tyr 795 | Val | Pro | Asn | Lys | Leu 800 |
| Val | Asn | Phe | Val | Ile 805 | Ala |

( 2 ) INFORMATION FOR SEQ ID NO:7:

( i ) SEQUENCE CHARACTERISTICS:

```
          ( A ) LENGTH: 2973 base pairs
          ( B ) TYPE: nucleic acid
          ( C ) STRANDEDNESS: double
          ( D ) TOPOLOGY: linear ( i x ) FEATURE:
          ( A ) NAME/KEY: CDS
          ( B ) LOCATION: 219..2834

( x i ) SEQUENCE DESCRIPTION: SEQ ID NO:7:

TGAATAAGGA  ATCAATTTTT  TCCAAACGCA  CTTCATTGAT  ATGCTCAAAT  CCTAAAATAG       60

GGGCTTTTAA  AAAGTAATTC  ACTGGACTAT  CCTTTTTAAT  TTAAATGCTT  TGTTGTATAA      120

TTTTGAAAAA  ATACGCAACA  ATTAAAAGCG  TAAAAGCAAA  AGGCGTTCCA  AATTCAACCA      180

TTTTTGAAAG  AACGCTCTAT  TTAGGATAA  TAATAATA  ATG AAA CAA GAA CCC            233
                                             Met Lys Gln Glu Pro
                                              1               5

ACC ACC TAC CAA CCA GAA GAG ATA GAA AAA AAG ATT TAT GAA ATT TGC             281
Thr Thr Tyr Gln Pro Glu Glu Ile Glu Lys Lys Ile Tyr Glu Ile Cys
             10                  15                  20

TCT CAT AGG GGG TAT TTT GAA ATT GAT GGC AAT GAA GCA ATC CAA GAA             329
Ser His Arg Gly Tyr Phe Glu Ile Asp Gly Asn Glu Ala Ile Gln Glu
         25                  30                  35

AAA AAC AAA CGA TTT TGC TTG ATG ATG CCC CCT CCT AAT GTG ACC GGT             377
Lys Asn Lys Arg Phe Cys Leu Met Met Pro Pro Pro Asn Val Thr Gly
     40                  45                  50

ATC TTA CAC ATA GGG CAT GCT TTG ACT TTA AGC TTG CAA GAT ATT TTA             425
Ile Leu His Ile Gly His Ala Leu Thr Leu Ser Leu Gln Asp Ile Leu
 55                  60                  65

GCG CGC TAT AAG CGC ATG GAC GGG TAT AAG ACT TTG TAT CAG CCC GGA             473
Ala Arg Tyr Lys Arg Met Asp Gly Tyr Lys Thr Leu Tyr Gln Pro Gly
 70                  75                  80                  85

TTG GAT CAC GCC GGC ATT GCG ACG CAA AAT GTC GTG GAA AAG CAA CTT             521
Leu Asp His Ala Gly Ile Ala Thr Gln Asn Val Val Glu Lys Gln Leu
             90                  95                 100

TTA AAT CAA GGG ATT AAA AAA GAA GAT TTA GGG CGT GAA GCG TTC GTT             569
Leu Asn Gln Gly Ile Lys Lys Glu Asp Leu Gly Arg Glu Ala Phe Val
        105                 110                 115

CAA AAA GTG TGG GAG TGG AAA GAA AAG AGT GGG GGA GCG ATT TTA GAG             617
Gln Lys Val Trp Glu Trp Lys Glu Lys Ser Gly Gly Ala Ile Leu Glu
    120                 125                 130

CAA ATG AAG CGT TTA GGC GTG AGC GCG GCC TTT TCT AGG ACT CGT TTC             665
Gln Met Lys Arg Leu Gly Val Ser Ala Ala Phe Ser Arg Thr Arg Phe
135                 140                 145

ACG ATG GAT AAG GGC TTG CAA AGA GCG GTT AAA TTG GCG TTT TTG AAA             713
Thr Met Asp Lys Gly Leu Gln Arg Ala Val Lys Leu Ala Phe Leu Lys
150                 155                 160                 165

TGG TAT GAA AAA GGT CTC ATC GTT CAA GAT AAT TAC ATG GTG AAT TGG             761
Trp Tyr Glu Lys Gly Leu Ile Val Gln Asp Asn Tyr Met Val Asn Trp
             170                 175                 180

TGC ACT AAA GAT GGG GCA TTG AGC GAT ATT GAA GTG GAG TAT GAA GAG             809
Cys Thr Lys Asp Gly Ala Leu Ser Asp Ile Glu Val Glu Tyr Glu Glu
         185                 190                 195

CGT AAG GGG GCG TTG TAT TAT ATT AGA TAT TAT TTA GAA AAT CAA AAA             857
Arg Lys Gly Ala Leu Tyr Tyr Ile Arg Tyr Tyr Leu Glu Asn Gln Lys
     200                 205                 210

GAT TAT TTA GTG GTG GCC ACC ACA CGC CCT GAA ACT TTG TTT GGC GAT             905
Asp Tyr Leu Val Val Ala Thr Thr Arg Pro Glu Thr Leu Phe Gly Asp
 215                 220                 225

AGC GCG CTT ATG GTC AAT CCT AAT GAT GAA AGA TAC AGG CAT TTA GTG             953
Ser Ala Leu Met Val Asn Pro Asn Asp Glu Arg Tyr Arg His Leu Val
230                 235                 240                 245
```

```
GGG CAA AAA GCG GTC TTG CCT TTA ATC AAT CGC ACA ATC CCT ATT ATC        1001
Gly Gln Lys Ala Val Leu Pro Leu Ile Asn Arg Thr Ile Pro Ile Ile
            250                 255                 260

GCT GAT GAA CAT GTG GAA ATG GAG TTT GGC ACA GGG TGT GTG AAA GTT        1049
Ala Asp Glu His Val Glu Met Glu Phe Gly Thr Gly Cys Val Lys Val
            265                 270                 275

ACC CCT GGG CAT GAT TTT AAC GAT TAC GAA GTG GGC AAA CGC CAC CAT        1097
Thr Pro Gly His Asp Phe Asn Asp Tyr Glu Val Gly Lys Arg His His
            280                 285                 290

TTG GAG GCG ATT AAA ATC TTT GAT GAA AAA GGG ATT TTA AAC GCG CAT        1145
Leu Glu Ala Ile Lys Ile Phe Asp Glu Lys Gly Ile Leu Asn Ala His
            295                 300                 305

TGT GGG GAG TTT GAA AAT TTA GAG CGA TTA GAA GCT AGA GAT AAG GTC        1193
Cys Gly Glu Phe Glu Asn Leu Glu Arg Leu Glu Ala Arg Asp Lys Val
310                 315                 320                 325

GTA GAA AGA TTA AAA GAA AAC GCC TTA TTG GAA AAA ATA GAA GAG CAC        1241
Val Glu Arg Leu Lys Glu Asn Ala Leu Leu Glu Lys Ile Glu Glu His
            330                 335                 340

ACG CAT CAA GTG GGG CAT TGC TAT CGT TGT CAT AAT GTG GTA GAG CCT        1289
Thr His Gln Val Gly His Cys Tyr Arg Cys His Asn Val Val Glu Pro
            345                 350                 355

TAT GTG TCT AAG CAA TGG TTT GTC AAG CCT GAA ATC GCT CAA AGT TCT        1337
Tyr Val Ser Lys Gln Trp Phe Val Lys Pro Glu Ile Ala Gln Ser Ser
            360                 365                 370

ATT GAA AAA ATC CAA CAA GGT TTA GCA CGA TTC TAC CCT TCT AAT TGG        1385
Ile Glu Lys Ile Gln Gln Gly Leu Ala Arg Phe Tyr Pro Ser Asn Trp
375                 380                 385

ATC AAT AAT TAT AAC GCT TGG ATG AGG GAA TTA CGC CCT TGG TGT ATC        1433
Ile Asn Asn Tyr Asn Ala Trp Met Arg Glu Leu Arg Pro Trp Cys Ile
390                 395                 400                 405

AGC AGG CAA TTG TTT TGG GGG CAT CAA ATA CCG GTA TTT ACT TGT GAA        1481
Ser Arg Gln Leu Phe Trp Gly His Gln Ile Pro Val Phe Thr Cys Glu
            410                 415                 420

AAT AAC CAC CAG TTT GTA AGC CTA GAC ACC CCC TTA AGT TGC CCT ACT        1529
Asn Asn His Gln Phe Val Ser Leu Asp Thr Pro Leu Ser Cys Pro Thr
            425                 430                 435

TGC AAG AGT GAA ATA CTA GAG CAA GAT AAA GAT GTG CTA GAC ACA TGG        1577
Cys Lys Ser Glu Ile Leu Glu Gln Asp Lys Asp Val Leu Asp Thr Trp
            440                 445                 450

TTT AGT TCA GGG CTA TGG GCG TTT TCC ACT CTA GGG TGG GGG CAA GAA        1625
Phe Ser Ser Gly Leu Trp Ala Phe Ser Thr Leu Gly Trp Gly Gln Glu
455                 460                 465

AAA AGC GGT TTG TTT AAT GAA AGC GAT TTG AAA GAT TTC TAC CCT AAC        1673
Lys Ser Gly Leu Phe Asn Glu Ser Asp Leu Lys Asp Phe Tyr Pro Asn
470                 475                 480                 485

ACA ACG CTC ATT ACC GGG TTT GAC ATC CTC TTT TTT TGG GTG GCC AGA        1721
Thr Thr Leu Ile Thr Gly Phe Asp Ile Leu Phe Phe Trp Val Ala Arg
            490                 495                 500

ATG CTC TTT TGC AGC GAA TCG CTT TTA GGC GAA TTG CCT TTT AAA GAT        1769
Met Leu Phe Cys Ser Glu Ser Leu Leu Gly Glu Leu Pro Phe Lys Asp
            505                 510                 515

ATT TAC TTG CAC GCC TTG GTT AGG GAT GAA AAG GGT GAA AAA ATG AGC        1817
Ile Tyr Leu His Ala Leu Val Arg Asp Glu Lys Gly Glu Lys Met Ser
            520                 525                 530

AAA TCT AAG GGT AAT GTG ATC GAT CCT TTA GAG ATG ATA GAA AAA TAC        1865
Lys Ser Lys Gly Asn Val Ile Asp Pro Leu Glu Met Ile Glu Lys Tyr
535                 540                 545

GGC GCG GAT AGT TTG CGT TTC ACT TTA GCC AAT TTG TGC GCT ACG GGC        1913
Gly Ala Asp Ser Leu Arg Phe Thr Leu Ala Asn Leu Cys Ala Thr Gly
550                 555                 560                 565
```

| | | | | | | | | | | | | | | | | |
|---|---|---|---|---|---|---|---|---|---|---|---|---|---|---|---|---|
| AGG | GAC | ATT | AAG | CTT | TCC | ACT | ACG | CAT | TTA | GAA | AAC | AAC | AAG | AAT | TTC | 1961 |
| Arg | Asp | Ile | Lys 570 | Leu | Ser | Thr | Thr | His 575 | Leu | Glu | Asn | Asn | Lys 580 | Asn | Phe | |
| GCC | AAC | AAG | ATT | TTC | AAT | GCG | GTG | AGT | TAT | TTG | AAA | CTC | AAA | CAA | GAA | 2009 |
| Ala | Asn | Lys | Ile 585 | Phe | Asn | Ala | Val | Ser 590 | Tyr | Leu | Lys | Leu | Lys 595 | Gln | Glu | |
| GCT | TTC | AAA | GAC | AGG | GAG | CGT | TTG | AAC | GAA | TAC | CAA | ACG | CCT | TTG | GGG | 2057 |
| Ala | Phe | Lys 600 | Asp | Arg | Glu | Arg | Leu | Asn 605 | Glu | Tyr | Gln | Thr | Pro 610 | Leu | Gly | |
| CGT | TAT | GCG | AAA | TCG | CGC | CTA | AAT | TCA | GCG | ACT | AAA | GAG | GCG | CGT | AAC | 2105 |
| Arg | Tyr | Ala 615 | Lys | Ser | Arg | Leu | Asn 620 | Ser | Ala | Thr | Lys 625 | Glu | Ala | Arg | Asn | |
| GCT | TTG | GAT | AAC | TAC | CGC | TTT | AAT | GAT | GCG | ACG | ACT | TTG | TTA | TAC | CGC | 2153 |
| Ala 630 | Leu | Asp | Asn | Tyr | Arg 635 | Phe | Asn | Asp | Ala | Thr 640 | Thr | Leu | Leu | Tyr | Arg 645 | |
| TTT | TTG | TGG | GGG | GAA | TTT | TGC | GAT | TGG | TTC | ATT | GAA | TTT | TCT | AAA | GTG | 2201 |
| Phe | Leu | Trp | Gly | Glu 650 | Phe | Cys | Asp | Trp | Phe 655 | Ile | Glu | Phe | Ser | Lys 660 | Val | |
| GAA | AAT | GGA | GCG | ATA | GAC | GAG | TTA | GGG | AGC | GTG | TTA | AAA | GAG | GCT | TTA | 2249 |
| Glu | Asn | Gly | Ala 665 | Ile | Asp | Glu | Leu | Gly 670 | Ser | Val | Leu | Lys | Glu 675 | Ala | Leu | |
| AAA | CTC | TTG | CAC | CCT | TTC | ATG | CCC | TTT | ATC | AGC | GAG | TCT | TTA | TAC | CAC | 2297 |
| Lys | Leu | Leu 680 | His | Pro | Phe | Met | Pro 685 | Phe | Ile | Ser | Glu | Ser 690 | Leu | Tyr | His | |
| AAG | CTC | AGT | AAC | ACG | GAA | CTA | GAA | AAC | ACT | GAA | TCT | ATC | ATG | GTC | ATG | 2345 |
| Lys | Leu 695 | Ser | Asn | Thr | Glu | Leu 700 | Glu | Asn | Thr | Glu | Ser 705 | Ile | Met | Val | Met | |
| CCT | TAC | CCT | AAA | GAT | TTG | GCA | CAA | GAT | GAA | AAA | CTA | GAG | CAT | GAA | TTT | 2393 |
| Pro 710 | Tyr | Pro | Lys | Asp | Leu 715 | Ala | Gln | Asp | Glu | Lys 720 | Leu | Glu | His | Glu | Phe 725 | |
| GAA | GTG | ATC | AAA | GAT | TGC | ATT | GTG | TCT | TTA | AGG | CGT | TTG | AAA | ATC | ATG | 2441 |
| Glu | Val | Ile | Lys | Asp 730 | Cys | Ile | Val | Ser | Leu 735 | Arg | Arg | Leu | Lys | Ile 740 | Met | |
| CTA | GAA | ACC | CCA | CCG | ATT | GTT | TTA | AAG | GAA | GCG | AGC | GTG | GGA | TTA | AGG | 2489 |
| Leu | Glu | Thr | Pro 745 | Pro | Ile | Val | Leu | Lys 750 | Glu | Ala | Ser | Val | Gly 755 | Leu | Arg | |
| GAA | AAA | ATA | GAA | AAC | ACA | GAG | CGT | TTG | CAA | ACT | TAT | GCT | CAA | AAA | TTA | 2537 |
| Glu | Lys | Ile | Glu 760 | Asn | Thr | Glu | Arg | Leu 765 | Gln | Thr | Tyr | Ala | Gln 770 | Lys | Leu | |
| GCG | AGG | TTA | GAA | AAA | GTC | AGC | GTG | ATA | ACT | TAT | AAG | CCT | TTA | AAA | AGC | 2585 |
| Ala | Arg 775 | Leu | Glu | Lys | Val | Ser 780 | Val | Ile | Thr | Tyr | Lys 785 | Pro | Leu | Lys | Ser | |
| GTG | AGC | GAT | GTG | GGG | GAA | TTT | TGC | CAA | ACT | TAT | GCA | AAT | TTA | GAA | AAT | 2633 |
| Val | Ser | Asp | Val 790 | Gly | Glu | Phe | Cys | Gln 795 | Thr | Tyr | Ala | Asn | Leu 800 | Glu | Asn 805 | |
| CTT | GAT | TTA | AGC | CCG | CTC | ATT | GCT | CGT | TTA | AAA | AAG | CAG | CTA | GAA | AAA | 2681 |
| Leu | Asp | Leu | Ser | Pro 810 | Leu | Ile | Ala | Arg | Leu 815 | Lys | Lys | Gln | Leu | Glu 820 | Lys | |
| CTG | GAA | AAA | GAA | AAA | TTA | AAA | CTC | AAT | TTG | CAC | AAT | GAA | AAT | TTT | GTT | 2729 |
| Leu | Glu | Lys | Glu 825 | Lys | Leu | Lys | Leu | Asn 830 | Leu | His | Asn | Glu | Asn 835 | Phe | Val | |
| AAA | AAC | GCA | CCT | AAA | AGC | GTG | CTA | GAA | AAA | GCC | AAA | GAG | AGT | TTA | AAA | 2777 |
| Lys | Asn | Ala | Pro 840 | Lys | Ser | Val | Leu | Glu 845 | Lys | Ala | Lys | Glu | Ser 850 | Leu | Lys | |
| ACG | CTT | TTA | GAA | AAA | GAA | AGT | AAA | ATT | AAG | CAA | GAA | TTG | GAT | TTG | TTA | 2825 |
| Thr | Leu | Leu 855 | Glu | Lys | Glu | Ser | Lys 860 | Ile | Lys | Gln | Glu | Leu 865 | Asp | Leu | Leu | |
| AAA | CAA | CCA | TAATAAAGG | | ATAGAAAATG | | TTTCAAGCAT | | TAAGCGATGG | | | | | | | 2874 |
| Lys | Gln | Pro 870 | | | | | | | | | | | | | | |

```
GTTTAAAAAC GCGCTCAATA AAATCCGCTT TCAAGACGAT GAAAAAGCGC TAGACAGAGC    2934

GTTAGATGAA TTGAAAAAAA CGCTTTTAAA AAACGATGT                            2973
```

( 2 ) INFORMATION FOR SEQ ID NO:8:

( i ) SEQUENCE CHARACTERISTICS:
        ( A ) LENGTH: 872 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Lys Gln Glu Pro Thr Thr Tyr Gln Pro Glu Glu Ile Glu Lys Lys
  1               5                  10                  15

Ile Tyr Glu Ile Cys Ser His Arg Gly Tyr Phe Glu Ile Asp Gly Asn
             20                  25                  30

Glu Ala Ile Gln Glu Lys Asn Lys Arg Phe Cys Leu Met Met Pro Pro
         35                  40                  45

Pro Asn Val Thr Gly Ile Leu His Ile Gly His Ala Leu Thr Leu Ser
     50                  55                  60

Leu Gln Asp Ile Leu Ala Arg Tyr Lys Arg Met Asp Gly Tyr Lys Thr
 65                  70                  75                  80

Leu Tyr Gln Pro Gly Leu Asp His Ala Gly Ile Ala Thr Gln Asn Val
                 85                  90                  95

Val Glu Lys Gln Leu Leu Asn Gln Gly Ile Lys Lys Glu Asp Leu Gly
            100                 105                 110

Arg Glu Ala Phe Val Gln Lys Val Trp Glu Trp Lys Glu Lys Ser Gly
        115                 120                 125

Gly Ala Ile Leu Glu Gln Met Lys Arg Leu Gly Val Ser Ala Ala Phe
    130                 135                 140

Ser Arg Thr Arg Phe Thr Met Asp Lys Gly Leu Gln Arg Ala Val Lys
145                 150                 155                 160

Leu Ala Phe Leu Lys Trp Tyr Glu Lys Gly Leu Ile Val Gln Asp Asn
                165                 170                 175

Tyr Met Val Asn Trp Cys Thr Lys Asp Gly Ala Leu Ser Asp Ile Glu
            180                 185                 190

Val Glu Tyr Glu Glu Arg Lys Gly Ala Leu Tyr Tyr Ile Arg Tyr Tyr
        195                 200                 205

Leu Glu Asn Gln Lys Asp Tyr Leu Val Val Ala Thr Thr Arg Pro Glu
    210                 215                 220

Thr Leu Phe Gly Asp Ser Ala Leu Met Val Asn Pro Asn Asp Glu Arg
225                 230                 235                 240

Tyr Arg His Leu Val Gly Gln Lys Ala Val Leu Pro Leu Ile Asn Arg
                245                 250                 255

Thr Ile Pro Ile Ile Ala Asp Glu His Val Glu Met Glu Phe Gly Thr
            260                 265                 270

Gly Cys Val Lys Val Thr Pro Gly His Asp Phe Asn Asp Tyr Glu Val
        275                 280                 285

Gly Lys Arg His His Leu Glu Ala Ile Lys Ile Phe Asp Glu Lys Gly
    290                 295                 300

Ile Leu Asn Ala His Cys Gly Glu Phe Glu Asn Leu Glu Arg Leu Glu
305                 310                 315                 320

Ala Arg Asp Lys Val Val Glu Arg Leu Lys Glu Asn Ala Leu Leu Glu
                325                 330                 335
```

```
Lys Ile Glu Glu His Thr His Gln Val Gly His Cys Tyr Arg Cys His
            340                 345                 350

Asn Val Val Glu Pro Tyr Val Ser Lys Gln Trp Phe Val Lys Pro Glu
            355                 360                 365

Ile Ala Gln Ser Ser Ile Glu Lys Ile Gln Gln Gly Leu Ala Arg Phe
            370                 375                 380

Tyr Pro Ser Asn Trp Ile Asn Asn Tyr Asn Ala Trp Met Arg Glu Leu
385                     390                 395                 400

Arg Pro Trp Cys Ile Ser Arg Gln Leu Phe Trp Gly His Gln Ile Pro
                405                 410                 415

Val Phe Thr Cys Glu Asn Asn His Gln Phe Val Ser Leu Asp Thr Pro
                420                 425                 430

Leu Ser Cys Pro Thr Cys Lys Ser Glu Ile Leu Glu Gln Asp Lys Asp
            435                 440                 445

Val Leu Asp Thr Trp Phe Ser Ser Gly Leu Trp Ala Phe Ser Thr Leu
    450                 455                 460

Gly Trp Gly Gln Glu Lys Ser Gly Leu Phe Asn Glu Ser Asp Leu Lys
465                 470                 475                 480

Asp Phe Tyr Pro Asn Thr Thr Leu Ile Thr Gly Phe Asp Ile Leu Phe
                485                 490                 495

Phe Trp Val Ala Arg Met Leu Phe Cys Ser Glu Ser Leu Leu Gly Glu
                500                 505                 510

Leu Pro Phe Lys Asp Ile Tyr Leu His Ala Leu Val Arg Asp Glu Lys
            515                 520                 525

Gly Glu Lys Met Ser Lys Ser Lys Gly Asn Val Ile Asp Pro Leu Glu
    530                 535                 540

Met Ile Glu Lys Tyr Gly Ala Asp Ser Leu Arg Phe Thr Leu Ala Asn
545                 550                 555                 560

Leu Cys Ala Thr Gly Arg Asp Ile Lys Leu Ser Thr Thr His Leu Glu
                565                 570                 575

Asn Asn Lys Asn Phe Ala Asn Lys Ile Phe Asn Ala Val Ser Tyr Leu
            580                 585                 590

Lys Leu Lys Gln Glu Ala Phe Lys Asp Arg Glu Arg Leu Asn Glu Tyr
    595                 600                 605

Gln Thr Pro Leu Gly Arg Tyr Ala Lys Ser Arg Leu Asn Ser Ala Thr
610                 615                 620

Lys Glu Ala Arg Asn Ala Leu Asp Asn Tyr Arg Phe Asn Asp Ala Thr
625                 630                 635                 640

Thr Leu Leu Tyr Arg Phe Leu Trp Gly Glu Phe Cys Asp Trp Phe Ile
                645                 650                 655

Glu Phe Ser Lys Val Glu Asn Gly Ala Ile Asp Glu Leu Gly Ser Val
            660                 665                 670

Leu Lys Glu Ala Leu Lys Leu Leu His Pro Phe Met Pro Phe Ile Ser
    675                 680                 685

Glu Ser Leu Tyr His Lys Leu Ser Asn Thr Glu Leu Glu Asn Thr Glu
    690                 695                 700

Ser Ile Met Val Met Pro Tyr Pro Lys Asp Leu Ala Gln Asp Glu Lys
705                 710                 715                 720

Leu Glu His Glu Phe Glu Val Ile Lys Asp Cys Ile Val Ser Leu Arg
                725                 730                 735

Arg Leu Lys Ile Met Leu Glu Thr Pro Pro Ile Val Leu Lys Glu Ala
                740                 745                 750

Ser Val Gly Leu Arg Glu Lys Ile Glu Asn Thr Glu Arg Leu Gln Thr
            755                 760                 765
```

```
Tyr  Ala  Gln  Lys  Leu  Ala  Arg  Leu  Glu  Lys  Val  Ser  Val  Ile  Thr  Tyr
     770                 775                 780

Lys  Pro  Leu  Lys  Ser  Val  Ser  Asp  Val  Gly  Glu  Phe  Cys  Gln  Thr  Tyr
785                      790                 795                           800

Ala  Asn  Leu  Glu  Asn  Leu  Asp  Leu  Ser  Pro  Leu  Ile  Ala  Arg  Leu  Lys
                    805                 810                           815

Lys  Gln  Leu  Glu  Lys  Leu  Glu  Lys  Glu  Lys  Leu  Lys  Leu  Asn  Leu  His
               820                 825                           830

Asn  Glu  Asn  Phe  Val  Lys  Asn  Ala  Pro  Lys  Ser  Val  Leu  Glu  Lys  Ala
          835                      840                      845

Lys  Glu  Ser  Leu  Lys  Thr  Leu  Leu  Glu  Lys  Glu  Ser  Lys  Ile  Lys  Gln
     850                      855                 860

Glu  Leu  Asp  Leu  Leu  Lys  Gln  Pro
865                      870
```

( 2 ) INFORMATION FOR SEQ ID NO:9:

( i ) SEQUENCE CHARACTERISTICS:
        ( A ) LENGTH: 1692 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 121..1623

( x i ) SEQUENCE DESCRIPTION: SEQ ID NO:9:

```
GGCGTGGAAT  CTTTAAAAGA  AAAGGCTAAA  GACTTGCCTA  AAAACATGTT  AGATCCAAAA           60

GCTAACCAAA  CCCCACCAAA  CCCTACCCCA  TCTAATAAAG  AACCCCTATA  AAGGCATCAC          120

ATG  TTT  TCT  AAC  CAA  TAC  ATC  CAA  CAA  CGC  ATC  CAT  AAA  GCC  AAT  AGC   168
Met  Phe  Ser  Asn  Gln  Tyr  Ile  Gln  Gln  Arg  Ile  His  Lys  Ala  Asn  Ser
1                   5                        10                       15

TTG  AGG  GAA  GAA  GGG  AAA  AAC  CCT  TAT  CAA  AAT  GGC  TTG  AAA  CGA  AGC   216
Leu  Arg  Glu  Glu  Gly  Lys  Asn  Pro  Tyr  Gln  Asn  Gly  Leu  Lys  Arg  Ser
                    20                       25                       30

CTC  ACC  AAC  GCC  GCT  TTT  TTA  GAA  AAA  TAC  GCT  TAT  ATT  AAG  GAT  TTA   264
Leu  Thr  Asn  Ala  Ala  Phe  Leu  Glu  Lys  Tyr  Ala  Tyr  Ile  Lys  Asp  Leu
          35                       40                       45

GAA  GAG  CCT  AAA  GAC  AAA  GAA  AAA  TGC  GAG  AGT  GTT  GTA  GGG  AGA  GTC   312
Glu  Glu  Pro  Lys  Asp  Lys  Glu  Lys  Cys  Glu  Ser  Val  Val  Gly  Arg  Val
     50                       55                       60

AAG  CTT  TTG  CGT  TTA  ATG  GGT  AAG  GCT  TGT  TTT  ATT  AAA  ATT  GAA  GAT   360
Lys  Leu  Leu  Arg  Leu  Met  Gly  Lys  Ala  Cys  Phe  Ile  Lys  Ile  Glu  Asp
65                       70                       75                       80

GAA  AGC  GCG  ATT  TTG  CAA  GCC  TAT  GTT  TCG  CAA  AAT  GAA  TTG  AAT  GAT   408
Glu  Ser  Ala  Ile  Leu  Gln  Ala  Tyr  Val  Ser  Gln  Asn  Glu  Leu  Asn  Asp
                    85                       90                       95

GAA  TTT  AAA  AGC  CTG  AAA  AAG  CAT  TTA  GAA  GTG  GGC  GAT  ATT  GTG  TTG   456
Glu  Phe  Lys  Ser  Leu  Lys  Lys  His  Leu  Glu  Val  Gly  Asp  Ile  Val  Leu
          100                      105                      110

GTG  AAA  GGT  TTC  CCT  TTT  GCT  ACC  AAA  ACC  GGT  GAA  TTA  AGC  GTT  CAT   504
Val  Lys  Gly  Phe  Pro  Phe  Ala  Thr  Lys  Thr  Gly  Glu  Leu  Ser  Val  His
     115                      120                      125

GCC  CTA  GAA  TTT  CAT  ATT  TTA  AGC  AAA  ACC  ATT  GTG  CCT  TTA  CCT  GAA   552
Ala  Leu  Glu  Phe  His  Ile  Leu  Ser  Lys  Thr  Ile  Val  Pro  Leu  Pro  Glu
130                      135                      140

AAG  TTT  CAT  GGA  TTA  AGC  GAT  ATA  GAA  TTG  CGT  TAC  CGC  CAG  CGC  TAC   600
Lys  Phe  His  Gly  Leu  Ser  Asp  Ile  Glu  Leu  Arg  Tyr  Arg  Gln  Arg  Tyr
145                      150                      155                      160
```

```
TTG GAT TTG ATC GTC AAT CCT AGC GTT AAA GAT GTG TTC AAA AAA CGC         648
Leu Asp Leu Ile Val Asn Pro Ser Val Lys Asp Val Phe Lys Lys Arg
            165                 170                 175

AGT TTG ATT GTT TCT AGC GTG CGG AAA TTC TTT GAA ATG GCA GGG TTT         696
Ser Leu Ile Val Ser Ser Val Arg Lys Phe Phe Glu Met Ala Gly Phe
        180                 185                 190

TTA GAA GTG GAA ACC CCC ATG ATG CAC CCC ATT CCT GGC GGG GCG AAC         744
Leu Glu Val Glu Thr Pro Met Met His Pro Ile Pro Gly Gly Ala Asn
            195                 200                 205

GCA AGG CCT TTT ATC ACT TAC CAT AAC GCT TTG GAG GTG GAG AGG TAT         792
Ala Arg Pro Phe Ile Thr Tyr His Asn Ala Leu Glu Val Glu Arg Tyr
    210                 215                 220

TTA AGA ATC GCC CCA GAA TTA TAC CTC AAA CGC TTG ATT GTA GGG GGG         840
Leu Arg Ile Ala Pro Glu Leu Tyr Leu Lys Arg Leu Ile Val Gly Gly
225                 230                 235                 240

TTT GAA GCG GTG TTT GAA ATC AAT CGT AAT TTC AGG AAT GAA GGC ATG         888
Phe Glu Ala Val Phe Glu Ile Asn Arg Asn Phe Arg Asn Glu Gly Met
                245                 250                 255

GAT CAC AGC CAT AAC CCC GAA TTC ACG ATG ATT GAG TTT TAT TGG GCG         936
Asp His Ser His Asn Pro Glu Phe Thr Met Ile Glu Phe Tyr Trp Ala
            260                 265                 270

TAT CAC ACT TAT GAA GAT TTG ATT GAA CTC AGT AAG AGG CTG TTT GAC         984
Tyr His Thr Tyr Glu Asp Leu Ile Glu Leu Ser Lys Arg Leu Phe Asp
        275                 280                 285

TAC TTG CTA AAG ACT TTG AAC TTA CCT TCA AAA ATC ATT TAT AAC GAT         1032
Tyr Leu Leu Lys Thr Leu Asn Leu Pro Ser Lys Ile Ile Tyr Asn Asp
    290                 295                 300

ATG GAA GTG GAT TTC AAC CAA ACG AGC GTG ATT TCC TAT TTG GAC GCT         1080
Met Glu Val Asp Phe Asn Gln Thr Ser Val Ile Ser Tyr Leu Asp Ala
305                 310                 315                 320

TTA GAA ACG ATA GGG GGC ATT AGT AAG GGT ATT TTA GAA AAA GAA GAC         1128
Leu Glu Thr Ile Gly Gly Ile Ser Lys Gly Ile Leu Glu Lys Glu Asp
                325                 330                 335

AGG CTT TTG GCT TAT TTG TTA GAG CAA GGC ATC AAA GTA GAG CCC AAT         1176
Arg Leu Leu Ala Tyr Leu Leu Glu Gln Gly Ile Lys Val Glu Pro Asn
            340                 345                 350

CTC ACT TAT GGC AAG TTG CTC GCT GAA GCG TTT GAT CAT TTT GTA GAG         1224
Leu Thr Tyr Gly Lys Leu Leu Ala Glu Ala Phe Asp His Phe Val Glu
        355                 360                 365

CAT CAA CTC ATT AAC CCC ACT TTT GTA ACC CAA TAC CCT ATT GAG ATT         1272
His Gln Leu Ile Asn Pro Thr Phe Val Thr Gln Tyr Pro Ile Glu Ile
    370                 375                 380

AGC CCT TTA GCC AGA CGC AAC GAT AGT AAC CCT AAT ATT GCT GAC AGG         1320
Ser Pro Leu Ala Arg Arg Asn Asp Ser Asn Pro Asn Ile Ala Asp Arg
385                 390                 395                 400

TTT GAA TTG TTC ATT GCA GGA AAA GAA ATC GCT AAT GGC TTT AGC GAG         1368
Phe Glu Leu Phe Ile Ala Gly Lys Glu Ile Ala Asn Gly Phe Ser Glu
                405                 410                 415

TTG AAC GAC CCT TTA GAT CAA TTA GAA CGC TTT AAA AAT CAA GTG GCT         1416
Leu Asn Asp Pro Leu Asp Gln Leu Glu Arg Phe Lys Asn Gln Val Ala
            420                 425                 430

GAA AAA GAA AAA GGC GAT GAA GAA GCC CAA TAC ATG GAT GAA GAT TAC         1464
Glu Lys Glu Lys Gly Asp Glu Glu Ala Gln Tyr Met Asp Glu Asp Tyr
        435                 440                 445

GTG TGG GCC CTA GCC CAT GGA ATG CCC CCC ACT GCA GGG CAA GGC ATA         1512
Val Trp Ala Leu Ala His Gly Met Pro Pro Thr Ala Gly Gln Gly Ile
    450                 455                 460

GGC ATT GAC CGA TTA GTG ATG TTA CTC ACT GGA GCT AAA AGC ATT AAA         1560
Gly Ile Asp Arg Leu Val Met Leu Leu Thr Gly Ala Lys Ser Ile Lys
465                 470                 475                 480
```

```
GAT GTG ATT TTA TTC CCA GCG ATG CGT CCT GTT AAA AAC GAT TTT AAT      1608
Asp Val Ile Leu Phe Pro Ala Met Arg Pro Val Lys Asn Asp Phe Asn
            485                 490                 495

GTG GAG AGT GGA GAA TAATGGCGTA TTTTTAGAA CAAACGGATA GTGAAATTTT        1663
Val Glu Ser Gly Glu
            500

TGAATTGATC TTTGAAGAAT ATAAGCGGC                                       1692
```

( 2 ) INFORMATION FOR SEQ ID NO:10:

( i ) SEQUENCE CHARACTERISTICS:
        ( A ) LENGTH: 501 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Phe Ser Asn Gln Tyr Ile Gln Gln Arg Ile His Lys Ala Asn Ser
 1               5                  10                  15

Leu Arg Glu Glu Gly Lys Asn Pro Tyr Gln Asn Gly Leu Lys Arg Ser
            20                  25                  30

Leu Thr Asn Ala Ala Phe Leu Glu Lys Tyr Ala Tyr Ile Lys Asp Leu
            35                  40                  45

Glu Glu Pro Lys Asp Lys Glu Lys Cys Glu Ser Val Val Gly Arg Val
        50                  55                  60

Lys Leu Leu Arg Leu Met Gly Lys Ala Cys Phe Ile Lys Ile Glu Asp
 65                  70                  75                  80

Glu Ser Ala Ile Leu Gln Ala Tyr Val Ser Gln Asn Glu Leu Asn Asp
                85                  90                  95

Glu Phe Lys Ser Leu Lys Lys His Leu Glu Val Gly Asp Ile Val Leu
            100                 105                 110

Val Lys Gly Phe Pro Phe Ala Thr Lys Thr Gly Glu Leu Ser Val His
            115                 120                 125

Ala Leu Glu Phe His Ile Leu Ser Lys Thr Ile Val Pro Leu Pro Glu
130                 135                 140

Lys Phe His Gly Leu Ser Asp Ile Glu Leu Arg Tyr Arg Gln Arg Tyr
145                 150                 155                 160

Leu Asp Leu Ile Val Asn Pro Ser Val Lys Asp Val Phe Lys Lys Arg
                165                 170                 175

Ser Leu Ile Val Ser Ser Val Arg Lys Phe Glu Met Ala Gly Phe
            180                 185                 190

Leu Glu Val Glu Thr Pro Met Met His Pro Ile Pro Gly Gly Ala Asn
            195                 200                 205

Ala Arg Pro Phe Ile Thr Tyr His Asn Ala Leu Glu Val Glu Arg Tyr
210                 215                 220

Leu Arg Ile Ala Pro Glu Leu Tyr Leu Lys Arg Leu Ile Val Gly Gly
225                 230                 235                 240

Phe Glu Ala Val Phe Glu Ile Asn Arg Asn Phe Arg Asn Glu Gly Met
                245                 250                 255

Asp His Ser His Asn Pro Glu Phe Thr Met Ile Glu Phe Tyr Trp Ala
            260                 265                 270

Tyr His Thr Tyr Glu Asp Leu Ile Glu Leu Ser Lys Arg Leu Phe Asp
        275                 280                 285

Tyr Leu Leu Lys Thr Leu Asn Leu Pro Ser Lys Ile Ile Tyr Asn Asp
290                 295                 300
```

```
Met  Glu  Val  Asp  Phe  Asn  Gln  Thr  Ser  Val  Ile  Ser  Tyr  Leu  Asp  Ala
305            310                 315                 320

Leu  Glu  Thr  Ile  Gly  Gly  Ile  Ser  Lys  Gly  Ile  Leu  Glu  Lys  Glu  Asp
                    325                 330                      335

Arg  Leu  Leu  Ala  Tyr  Leu  Leu  Glu  Gln  Gly  Ile  Lys  Val  Glu  Pro  Asn
                340                 345                 350

Leu  Thr  Tyr  Gly  Lys  Leu  Leu  Ala  Glu  Ala  Phe  Asp  His  Phe  Val  Glu
               355                 360                 365

His  Gln  Leu  Ile  Asn  Pro  Thr  Phe  Val  Thr  Gln  Tyr  Pro  Ile  Glu  Ile
     370                      375                 380

Ser  Pro  Leu  Ala  Arg  Arg  Asn  Asp  Ser  Asn  Pro  Asn  Ile  Ala  Asp  Arg
385                      390                 395                           400

Phe  Glu  Leu  Phe  Ile  Ala  Gly  Lys  Glu  Ile  Ala  Asn  Gly  Phe  Ser  Glu
                    405                 410                      415

Leu  Asn  Asp  Pro  Leu  Asp  Gln  Leu  Glu  Arg  Phe  Lys  Asn  Gln  Val  Ala
                420                 425                 430

Glu  Lys  Glu  Lys  Gly  Asp  Glu  Ala  Gln  Tyr  Met  Asp  Glu  Asp  Tyr
          435                 440                 445

Val  Trp  Ala  Leu  Ala  His  Gly  Met  Pro  Pro  Thr  Ala  Gly  Gln  Gly  Ile
     450                      455                      460

Gly  Ile  Asp  Arg  Leu  Val  Met  Leu  Leu  Thr  Gly  Ala  Lys  Ser  Ile  Lys
465                      470                 475                           480

Asp  Val  Ile  Leu  Phe  Pro  Ala  Met  Arg  Pro  Val  Lys  Asn  Asp  Phe  Asn
                    485                 490                      495

Val  Glu  Ser  Gly  Glu
               500
```

( 2 ) INFORMATION FOR SEQ ID NO:11:

( i ) SEQUENCE CHARACTERISTICS:
    ( A ) LENGTH: 1431 base pairs
    ( B ) TYPE: nucleic acid
    ( C ) STRANDEDNESS: double
    ( D ) TOPOLOGY: linear ( i x ) FEATURE:
    ( A ) NAME/KEY: CDS
    ( B ) LOCATION: 80..1324

( x i ) SEQUENCE DESCRIPTION: SEQ ID NO:11:

```
TTTGAACGCT  CAAATAGATA  AAAATGAAAT  TGATGAATGG  GCTAAATTGT  GGCATTTTAG                60

AACGATTAAA  GAGGGTTGA  ATG  ATT  GAT  AGA  AAA  CTT  TTA  TTG  CAA  GAT  TTT        112
                       Met  Ile  Asp  Arg  Lys  Leu  Leu  Leu  Gln  Asp  Phe
                        1                 5                      10

GAC  AAG  GTG  GCT  CTT  TCT  TTA  AAA  AAG  CGT  AAT  CAT  GCG  ATG  GAT  GAT     160
Asp  Lys  Val  Ala  Leu  Ser  Leu  Lys  Lys  Arg  Asn  His  Ala  Met  Asp  Asp
               15                      20                      25

GGA  TTG  GAG  CGT  TTG  CGC  GAA  GTC  ATC  ACG  CGT  TAT  AAA  AAG  CAA  CTC     208
Gly  Leu  Glu  Arg  Leu  Arg  Glu  Val  Ile  Thr  Arg  Tyr  Lys  Lys  Gln  Leu
          30                      35                      40

ATT  GAA  TTG  GAA  GGC  TTG  CAA  GCC  TTT  CAA  AAC  AAG  GTT  TCT  AAA  GAA     256
Ile  Glu  Leu  Glu  Gly  Leu  Gln  Ala  Phe  Gln  Asn  Lys  Val  Ser  Lys  Glu
     45                      50                      55

TTT  GGT  ATC  AAA  ATG  GCT  CAA  AAA  GTG  GAT  ACA  AGC  GAT  CTC  AAA  AAA     304
Phe  Gly  Ile  Lys  Met  Ala  Gln  Lys  Val  Asp  Thr  Ser  Asp  Leu  Lys  Lys
60                      65                      70                           75

GAG  CTA  GAA  AGC  AAT  AAA  ATC  AAA  TTG  AAT  GAG  CTT  TCT  AAA  AGC  GTG     352
Glu  Leu  Glu  Ser  Asn  Lys  Ile  Lys  Leu  Asn  Glu  Leu  Ser  Lys  Ser  Val
               80                      85                      90
```

| | | | | | | | | | | | | | | | | |
|---|---|---|---|---|---|---|---|---|---|---|---|---|---|---|---|---|
| GGC | GAA | TTG | GAG | CAA | CAA | ATT | GAT | TTG | AAG | CTT | TCC | ATA | ATC | CCT | AAT | 400 |
| Gly | Glu | Leu | Glu | Gln | Gln | Ile | Asp | Leu | Lys | Leu | Ser | Ile | Ile | Pro | Asn | |
| | | 95 | | | | | 100 | | | | | 105 | | | | |
| CTA | GTG | GAT | GAA | AAA | ACC | CCT | TTA | GGC | GCA | AAT | GAA | GAA | GAC | AAC | ATA | 448 |
| Leu | Val | Asp | Glu | Lys | Thr | Pro | Leu | Gly | Ala | Asn | Glu | Glu | Asp | Asn | Ile | |
| | | 110 | | | | | 115 | | | | | 120 | | | | |
| GAA | ATT | AAA | AAA | ATC | TTA | ACC | CCA | AGG | GTT | TTT | ACT | TTC | AAA | CCC | AAA | 496 |
| Glu | Ile | Lys | Lys | Ile | Leu | Thr | Pro | Arg | Val | Phe | Thr | Phe | Lys | Pro | Lys | |
| | 125 | | | | | 130 | | | | | 135 | | | | | |
| GAG | CAT | TTT | GAG | CTC | GCT | CAA | CAA | AAC | GGC | TGG | ATT | GAT | TTT | GAA | GGC | 544 |
| Glu | His | Phe | Glu | Leu | Ala | Gln | Gln | Asn | Gly | Trp | Ile | Asp | Phe | Glu | Gly | |
| 140 | | | | | 145 | | | | | 150 | | | | | 155 | |
| GGC | GTG | AAA | CTC | GCC | AAA | AGC | CGT | TTT | TCG | GTC | ATT | AGG | GGT | TTT | GGG | 592 |
| Gly | Val | Lys | Leu | Ala | Lys | Ser | Arg | Phe | Ser | Val | Ile | Arg | Gly | Phe | Gly | |
| | | | | 160 | | | | | 165 | | | | | 170 | | |
| GCT | AAA | ATT | TAT | CGC | GCG | CTC | ATT | CAT | TTA | ATG | CTG | GAT | TTT | AAT | GAA | 640 |
| Ala | Lys | Ile | Tyr | Arg | Ala | Leu | Ile | His | Leu | Met | Leu | Asp | Phe | Asn | Glu | |
| | | | 175 | | | | | 180 | | | | | 185 | | | |
| AAA | AAT | GGC | TTT | GAA | ATC | ATC | TAC | ACG | CCG | GCG | TTA | GTG | AAT | GAA | AAA | 688 |
| Lys | Asn | Gly | Phe | Glu | Ile | Ile | Tyr | Thr | Pro | Ala | Leu | Val | Asn | Glu | Lys | |
| | | 190 | | | | | 195 | | | | | 200 | | | | |
| ATG | CTT | TTT | GGG | ACC | GGG | CAA | TTA | CCC | AAA | TTC | AAA | GAA | GAT | ATT | TTC | 736 |
| Met | Leu | Phe | Gly | Thr | Gly | Gln | Leu | Pro | Lys | Phe | Lys | Glu | Asp | Ile | Phe | |
| | 205 | | | | | 210 | | | | | 215 | | | | | |
| AAA | ATA | GAA | AAT | GAA | AAT | TTG | TAT | CTG | ATT | CCC | ACC | GCT | GAG | GTA | ACG | 784 |
| Lys | Ile | Glu | Asn | Glu | Asn | Leu | Tyr | Leu | Ile | Pro | Thr | Ala | Glu | Val | Thr | |
| 220 | | | | | 225 | | | | | 230 | | | | | 235 | |
| CTC | ACC | AAT | CTA | TAC | AAC | GAC | ACC | ATT | ATT | AGC | GTT | GAA | AAC | CTC | CCC | 832 |
| Leu | Thr | Asn | Leu | Tyr | Asn | Asp | Thr | Ile | Ile | Ser | Val | Glu | Asn | Leu | Pro | |
| | | | 240 | | | | | 245 | | | | | 250 | | | |
| ATT | AAA | ATG | ACC | GCG | CAC | ACG | CCT | TGT | TTC | AGG | AGC | GAA | GCG | GGG | AGC | 880 |
| Ile | Lys | Met | Thr | Ala | His | Thr | Pro | Cys | Phe | Arg | Ser | Glu | Ala | Gly | Ser | |
| | | | 255 | | | | | 260 | | | | | 265 | | | |
| GCG | GGC | AAG | GAC | ACA | AGG | GGG | ATG | ATA | AGA | CAG | CAC | CAA | TTT | GAT | AAA | 928 |
| Ala | Gly | Lys | Asp | Thr | Arg | Gly | Met | Ile | Arg | Gln | His | Gln | Phe | Asp | Lys | |
| | | 270 | | | | | 275 | | | | | 280 | | | | |
| GTA | GAA | TTA | GTG | GCT | ATC | ACG | CAC | CCT | AAA | GAA | AGC | GAT | GTT | ATG | CAA | 976 |
| Val | Glu | Leu | Val | Ala | Ile | Thr | His | Pro | Lys | Glu | Ser | Asp | Val | Met | Gln | |
| | 285 | | | | | 290 | | | | | 295 | | | | | |
| GAG | CAT | ATG | CTA | GAG | AGC | GCG | AGC | GAG | ATC | TTA | AAG | GCT | TTG | GAA | TTA | 1024 |
| Glu | His | Met | Leu | Glu | Ser | Ala | Ser | Glu | Ile | Leu | Lys | Ala | Leu | Glu | Leu | |
| 300 | | | | | 305 | | | | | 310 | | | | | 315 | |
| CCG | CAC | CGG | TTC | GTG | CAA | TTG | TGC | AGC | GCG | GAT | TTA | GGC | TTT | AGT | GCG | 1072 |
| Pro | His | Arg | Phe | Val | Gln | Leu | Cys | Ser | Ala | Asp | Leu | Gly | Phe | Ser | Ala | |
| | | | 320 | | | | | 325 | | | | | 330 | | | |
| AGC | AAC | ACG | ATA | GAC | ATT | GAA | GTG | TGG | CTG | CCC | GGG | CAA | AAT | TGC | TAC | 1120 |
| Ser | Asn | Thr | Ile | Asp | Ile | Glu | Val | Trp | Leu | Pro | Gly | Gln | Asn | Cys | Tyr | |
| | | | 335 | | | | | 340 | | | | | 345 | | | |
| CGA | GAA | ATC | AGC | TCC | GTG | TCT | AAC | ACG | AGG | GAT | TTC | CAG | GCC | AGG | CGT | 1168 |
| Arg | Glu | Ile | Ser | Ser | Val | Ser | Asn | Thr | Arg | Asp | Phe | Gln | Ala | Arg | Arg | |
| | | 350 | | | | | 355 | | | | | 360 | | | | |
| GCC | AAA | ATC | CGC | TTC | AAA | GAA | AAT | CAA | AAA | AAC | CAA | TTA | GCG | CAC | ACC | 1216 |
| Ala | Lys | Ile | Arg | Phe | Lys | Glu | Asn | Gln | Lys | Asn | Gln | Leu | Ala | His | Thr | |
| | 365 | | | | | 370 | | | | | 375 | | | | | |
| TTA | AAC | GGC | TCT | TCT | TTA | GCG | GTA | GGC | AGG | ACG | ATG | GTC | GCT | TTA | ATG | 1264 |
| Leu | Asn | Gly | Ser | Ser | Leu | Ala | Val | Gly | Arg | Thr | Met | Val | Ala | Leu | Met | |
| 380 | | | | | 385 | | | | | 390 | | | | | 395 | |
| GAA | AAC | CAC | CAG | CAA | GCG | GAT | GGA | AAC | ATC | CAC | ATT | CCT | AAG | GCG | TTA | 1312 |
| Glu | Asn | His | Gln | Gln | Ala | Asp | Gly | Asn | Ile | His | Ile | Pro | Lys | Ala | Leu | |
| | | | 400 | | | | | 405 | | | | | 410 | | | |

```
GAA AAA TAC CTT TAAGGCTAGT TCGTGCTGAA TGAAGAGCAA AATTCATTAG        1364
Glu Lys Tyr Leu
            415

AAGAAAAAGG GGGCGAAAAC AAAAACGAAA AAGAAACCCC CTAAAAGGCA TTCATTCTAA  1424

AATCCCC                                                            1431
```

( 2 ) INFORMATION FOR SEQ ID NO:12:

( i ) SEQUENCE CHARACTERISTICS:
        ( A ) LENGTH: 415 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Ile Asp Arg Lys Leu Leu Leu Gln Asp Phe Asp Lys Val Ala Leu
 1               5                  10                  15

Ser Leu Lys Lys Arg Asn His Ala Met Asp Asp Gly Leu Glu Arg Leu
             20                  25                  30

Arg Glu Val Ile Thr Arg Tyr Lys Lys Gln Leu Ile Glu Leu Glu Gly
             35                  40                  45

Leu Gln Ala Phe Gln Asn Lys Val Ser Lys Glu Phe Gly Ile Lys Met
     50                  55                  60

Ala Gln Lys Val Asp Thr Ser Asp Leu Lys Lys Glu Leu Glu Ser Asn
 65                  70                  75                  80

Lys Ile Lys Leu Asn Glu Leu Ser Lys Ser Val Gly Glu Leu Glu Gln
                 85                  90                  95

Gln Ile Asp Leu Lys Leu Ser Ile Ile Pro Asn Leu Val Asp Glu Lys
             100                 105                 110

Thr Pro Leu Gly Ala Asn Glu Glu Asp Asn Ile Glu Ile Lys Lys Ile
         115                 120                 125

Leu Thr Pro Arg Val Phe Thr Phe Lys Pro Lys Glu His Phe Glu Leu
     130                 135                 140

Ala Gln Gln Asn Gly Trp Ile Asp Phe Glu Gly Gly Val Lys Leu Ala
145                 150                 155                 160

Lys Ser Arg Phe Ser Val Ile Arg Gly Phe Gly Ala Lys Ile Tyr Arg
                165                 170                 175

Ala Leu Ile His Leu Met Leu Asp Phe Asn Glu Lys Asn Gly Phe Glu
             180                 185                 190

Ile Ile Tyr Thr Pro Ala Leu Val Asn Glu Lys Met Leu Phe Gly Thr
         195                 200                 205

Gly Gln Leu Pro Lys Phe Lys Glu Asp Ile Phe Lys Ile Glu Asn Glu
     210                 215                 220

Asn Leu Tyr Leu Ile Pro Thr Ala Glu Val Thr Leu Thr Asn Leu Tyr
225                 230                 235                 240

Asn Asp Thr Ile Ile Ser Val Glu Asn Leu Pro Ile Lys Met Thr Ala
                245                 250                 255

His Thr Pro Cys Phe Arg Ser Glu Ala Gly Ser Ala Gly Lys Asp Thr
             260                 265                 270

Arg Gly Met Ile Arg Gln His Gln Phe Asp Lys Val Glu Leu Val Ala
         275                 280                 285

Ile Thr His Pro Lys Glu Ser Asp Val Met Gln Glu His Met Leu Glu
     290                 295                 300

Ser Ala Ser Glu Ile Leu Lys Ala Leu Glu Leu Pro His Arg Phe Val
305                 310                 315                 320
```

| | | | | | | | | | | | | | | |
|---|---|---|---|---|---|---|---|---|---|---|---|---|---|---|
| Gln | Leu | Cys | Ser | Ala<br>325 | Asp | Leu | Gly | Phe | Ser<br>330 | Ala | Ser | Asn | Thr | Ile<br>335 | Asp |
| Ile | Glu | Val | Trp<br>340 | Leu | Pro | Gly | Gln | Asn<br>345 | Cys | Tyr | Arg | Glu | Ile<br>350 | Ser | Ser |
| Val | Ser | Asn<br>355 | Thr | Arg | Asp | Phe | Gln<br>360 | Ala | Arg | Arg | Ala | Lys<br>365 | Ile | Arg | Phe |
| Lys | Glu<br>370 | Asn | Gln | Lys | Asn | Gln<br>375 | Leu | Ala | His | Thr | Leu<br>380 | Asn | Gly | Ser | Ser |
| Leu<br>385 | Ala | Val | Gly | Arg | Thr<br>390 | Met | Val | Ala | Leu | Met<br>395 | Glu | Asn | His | Gln | Gln<br>400 |
| Ala | Asp | Gly | Asn | Ile<br>405 | His | Ile | Pro | Lys | Ala<br>410 | Leu | Glu | Lys | Tyr | Leu<br>415 | |

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 14
        ( D ) OTHER INFORMATION: /mod_base=i ( i x ) FEATURE:
        ( A ) NAME/KEY: modified_base
        ( B ) LOCATION: 17
        ( D ) OTHER INFORMATION: /mod_base=i ( i x ) FEATURE:
        ( A ) NAME/KEY: modified_base
        ( B ) LOCATION: 20
        ( D ) OTHER INFORMATION: /mod_base=i ( i x ) FEATURE:
        ( A ) NAME/KEY: modified_base
        ( B ) LOCATION: 23
        ( D ) OTHER INFORMATION: /mod_base=i ( x i ) SEQUENCE DESCRIPTION: SEQ ID NO:13:

```
GCGAATTCTW YCTNACNGGN ACNGAYGARC AYGG                                34
```

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 14
        ( D ) OTHER INFORMATION: /mod_base=i ( i x ) FEATURE:
        ( A ) NAME/KEY: modified_base
        ( B ) LOCATION: 20
        ( D ) OTHER INFORMATION: /mod_base=i ( i x ) FEATURE:
        ( A ) NAME/KEY: modified_base
        ( B ) LOCATION: 23
        ( D ) OTHER INFORMATION: /mod_base=i ( x i ) SEQUENCE DESCRIPTION: SEQ ID NO:14:

```
GCGAATTCTT YATNTGYGGN ACNGAYGARY AYGG                                34
```

( 2 ) INFORMATION FOR SEQ ID NO:15:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 15
        ( D ) OTHER INFORMATION: /mod_base=i ( i x ) FEATURE:
        ( A ) NAME/KEY: modified_base
        ( B ) LOCATION: 18
        ( D ) OTHER INFORMATION: /mod_base=i ( i x ) FEATURE:
        ( A ) NAME/KEY: modified_base
        ( B ) LOCATION: 21
        ( D ) OTHER INFORMATION: /mod_base=i ( i x ) FEATURE:
        ( A ) NAME/KEY: modified_base
        ( B ) LOCATION: 33
        ( D ) OTHER INFORMATION: /mod_base=i ( x i ) SEQUENCE DESCRIPTION: SEQ ID NO:15:

GCGAATTCRT ARTTNATNAG NGCRTCRAWC CANACRTA        38

( 2 ) INFORMATION FOR SEQ ID NO:16:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 12
        ( D ) OTHER INFORMATION: /mod_base=i ( i x ) FEATURE:
        ( A ) NAME/KEY: modified_base
        ( B ) LOCATION: 18
        ( D ) OTHER INFORMATION: /mod_base=i ( i x ) FEATURE:
        ( A ) NAME/KEY: modified_base
        ( B ) LOCATION: 21
        ( D ) OTHER INFORMATION: /mod_base=i ( i x ) FEATURE:
        ( A ) NAME/KEY: modified_base
        ( B ) LOCATION: 27
        ( D ) OTHER INFORMATION: /mod_base=i ( i x ) FEATURE:
        ( A ) NAME/KEY: modified_base
        ( B ) LOCATION: 33
        ( D ) OTHER INFORMATION: /mod_base=i ( x i ) SEQUENCE DESCRIPTION: SEQ ID NO:16:

GCGAATTCRT ANCCRATNGK NGCRTCNARC CANACRTA        38

( 2 ) INFORMATION FOR SEQ ID NO:17:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i x ) FEATURE:

( A ) NAME/KEY: modified_base
              ( B ) LOCATION: 11
              ( D ) OTHER INFORMATION: /mod_base=i ( i x ) FEATURE:
              ( A ) NAME/KEY: modified_base
              ( B ) LOCATION: 20
              ( D ) OTHER INFORMATION: /mod_base=i ( i x ) FEATURE:
              ( A ) NAME/KEY: modified_base
              ( B ) LOCATION: 26
              ( D ) OTHER INFORMATION: /mod_base=i ( i x ) FEATURE:
              ( A ) NAME/KEY: modified_base
              ( B ) LOCATION: 29
              ( D ) OTHER INFORMATION: /mod_base=i ( x i ) SEQUENCE DESCRIPTION: SEQ ID NO:17:

GCGAATTCGG NTGGGAYACN CAYGGNSTNC C     31

( 2 ) INFORMATION FOR SEQ ID NO:18:

( i ) SEQUENCE CHARACTERISTICS:
              ( A ) LENGTH: 31 base pairs
              ( B ) TYPE: nucleic acid
              ( C ) STRANDEDNESS: single
              ( D ) TOPOLOGY: linear ( i x ) FEATURE:
              ( A ) NAME/KEY: modified_base
              ( B ) LOCATION: 11
              ( D ) OTHER INFORMATION: /mod_base=i ( i x ) FEATURE:
              ( A ) NAME/KEY: modified_base
              ( B ) LOCATION: 26
              ( D ) OTHER INFORMATION: /mod_base=i ( i x ) FEATURE:
              ( A ) NAME/KEY: modified_base
              ( B ) LOCATION: 29
              ( D ) OTHER INFORMATION: /mod_base=i ( x i ) SEQUENCE DESCRIPTION: SEQ ID NO:18:

GCGAATTCGG NTGGGAYTGY CAYGGNCTNC C     31

( 2 ) INFORMATION FOR SEQ ID NO:19:

( i ) SEQUENCE CHARACTERISTICS:
              ( A ) LENGTH: 33 base pairs
              ( B ) TYPE: nucleic acid
              ( C ) STRANDEDNESS: single
              ( D ) TOPOLOGY: linear ( i x ) FEATURE:
              ( A ) NAME/KEY: modified_base
              ( B ) LOCATION: 10
              ( D ) OTHER INFORMATION: /mod_base=i ( i x ) FEATURE:
              ( A ) NAME/KEY: modified_base
              ( B ) LOCATION: 16
              ( D ) OTHER INFORMATION: /mod_base=i ( i x ) FEATURE:
              ( A ) NAME/KEY: modified_base
              ( B ) LOCATION: 25
              ( D ) OTHER INFORMATION: /mod_base=i ( i x ) FEATURE:
              ( A ) NAME/KEY: modified_base
              ( B ) LOCATION: 28
              ( D ) OTHER INFORMATION: /mod_base=i (ix) FEATURE:
  (A) NAME/KEY: modified_base
  (B) LOCATION: 31
  (D) OTHER INFORMATION: /mod_base=i (xi) SEQUENCE DESCRIPTION: SEQ ID NO:19:

GCGAATTCGN CARCGNTAYT GGGGNRTNCC NAT  33

(2) INFORMATION FOR SEQ ID NO:20:

(i) SEQUENCE CHARACTERISTICS:
    (A) LENGTH: 33 base pairs
    (B) TYPE: nucleic acid
    (C) STRANDEDNESS: single
    (D) TOPOLOGY: linear (ix) FEATURE:
    (A) NAME/KEY: modified_base
    (B) LOCATION: 10
    (D) OTHER INFORMATION: /mod_base=i (ix) FEATURE:
    (A) NAME/KEY: modified_base
    (B) LOCATION: 16
    (D) OTHER INFORMATION: /mod_base=i (ix) FEATURE:
    (A) NAME/KEY: modified_base
    (B) LOCATION: 25
    (D) OTHER INFORMATION: /mod_base=i (ix) FEATURE:
    (A) NAME/KEY: modified_base
    (B) LOCATION: 28
    (D) OTHER INFORMATION: /mod_base=i (ix) FEATURE:
    (A) NAME/KEY: modified_base
    (B) LOCATION: 31
    (D) OTHER INFORMATION: /mod_base=i (xi) SEQUENCE DESCRIPTION: SEQ ID NO:20:

GCGAATTCGN AAYCGNTWYT GGGGNACNCC NMT  33

(2) INFORMATION FOR SEQ ID NO:21:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (ix) FEATURE:
    (A) NAME/KEY: modified_base
    (B) LOCATION: 15
    (D) OTHER INFORMATION: /mod_base=i (ix) FEATURE:
    (A) NAME/KEY: modified_base
    (B) LOCATION: 18
    (D) OTHER INFORMATION: /mod_base=i (ix) FEATURE:
    (A) NAME/KEY: modified_base
    (B) LOCATION: 21
    (D) OTHER INFORMATION: /mod_base=i (ix) FEATURE:
    (A) NAME/KEY: modified_base
    (B) LOCATION: 30
    (D) OTHER INFORMATION: /mod_base=i (ix) FEATURE:
    (A) NAME/KEY: modified_base
    (B) LOCATION: 33
    (D) OTHER INFORMATION: /mod_base=i ( x i ) SEQUENCE DESCRIPTION: SEQ ID NO:21:

GCGAATTCRA ACCANCCNCG NGTYTGRTCN WWNCCYTC   38

( 2 ) INFORMATION FOR SEQ ID NO:22:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 3
        ( D ) OTHER INFORMATION: /mod_base=i ( i x ) FEATURE:
        ( A ) NAME/KEY: modified_base
        ( B ) LOCATION: 6
        ( D ) OTHER INFORMATION: /mod_base=i ( i x ) FEATURE:
        ( A ) NAME/KEY: modified_base
        ( B ) LOCATION: 12
        ( D ) OTHER INFORMATION: /mod_base=i ( i x ) FEATURE:
        ( A ) NAME/KEY: modified_base
        ( B ) LOCATION: 15
        ( D ) OTHER INFORMATION: /mod_base=i ( i x ) FEATURE:
        ( A ) NAME/KEY: modified_base
        ( B ) LOCATION: 18
        ( D ) OTHER INFORMATION: /mod_base=i ( i x ) FEATURE:
        ( A ) NAME/KEY: modified_base
        ( B ) LOCATION: 21
        ( D ) OTHER INFORMATION: /mod_base=i ( x i ) SEQUENCE DESCRIPTION: SEQ ID NO:22:

GGNARNGTCC ANGGNGTNGT NGTCCA   26

( 2 ) INFORMATION FOR SEQ ID NO:23:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 12
        ( D ) OTHER INFORMATION: /mod_base=i ( i x ) FEATURE:
        ( A ) NAME/KEY: modified_base
        ( B ) LOCATION: 15
        ( D ) OTHER INFORMATION: /mod_base=i ( i x ) FEATURE:
        ( A ) NAME/KEY: modified_base
        ( B ) LOCATION: 24
        ( D ) OTHER INFORMATION: /mod_base=i ( i x ) FEATURE:
        ( A ) NAME/KEY: modified_base
        ( B ) LOCATION: 27
        ( D ) OTHER INFORMATION: /mod_base=i ( x i ) SEQUENCE DESCRIPTION: SEQ ID NO:23:

TWYATGGART CNACNTGGTG GGYNTTNAAR CA   32

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 9
        ( D ) OTHER INFORMATION: /mod_base=i ( i x ) FEATURE:
        ( A ) NAME/KEY: modified_base
        ( B ) LOCATION: 12
        ( D ) OTHER INFORMATION: /mod_base=i ( i x ) FEATURE:
        ( A ) NAME/KEY: modified_base
        ( B ) LOCATION: 18
        ( D ) OTHER INFORMATION: /mod_base=i ( x i ) SEQUENCE DESCRIPTION: SEQ ID NO:24:

GAYCAYGCNG GNATHGCNAC NCA                                        23

( 2 ) INFORMATION FOR SEQ ID NO:25:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 7
        ( D ) OTHER INFORMATION: /mod_base=i ( i x ) FEATURE:
        ( A ) NAME/KEY: modified_base
        ( B ) LOCATION: 10
        ( D ) OTHER INFORMATION: /mod_base=i ( i x ) FEATURE:
        ( A ) NAME/KEY: modified_base
        ( B ) LOCATION: 13
        ( D ) OTHER INFORMATION: /mod_base=i ( x i ) SEQUENCE DESCRIPTION: SEQ ID NO:25:

RTCRTGNGCN GGNGTDATYT T                                         21

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 7
        ( D ) OTHER INFORMATION: /mod_base=i ( i x ) FEATURE:
        ( A ) NAME/KEY: modified_base
        ( B ) LOCATION: 13
        ( D ) OTHER INFORMATION: /mod_base=i ( i x ) FEATURE:
        ( A ) NAME/KEY: modified_base
        ( B ) LOCATION: 16
        ( D ) OTHER INFORMATION: /mod_base=i ( x i ) SEQUENCE DESCRIPTION: SEQ ID NO:26:

RAACCANGTR TCNARNACRT C  21

( 2 ) INFORMATION FOR SEQ ID NO:27:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 10
        ( D ) OTHER INFORMATION: /mod_base=i ( i x ) FEATURE:
        ( A ) NAME/KEY: modified_base
        ( B ) LOCATION: 13
        ( D ) OTHER INFORMATION: /mod_base=i ( i x ) FEATURE:
        ( A ) NAME/KEY: modified_base
        ( B ) LOCATION: 16
        ( D ) OTHER INFORMATION: /mod_base=i ( i x ) FEATURE:
        ( A ) NAME/KEY: modified_base
        ( B ) LOCATION: 25
        ( D ) OTHER INFORMATION: /mod_base=i ( i x ) FEATURE:
        ( A ) NAME/KEY: modified_base
        ( B ) LOCATION: 31
        ( D ) OTHER INFORMATION: /mod_base=i ( i x ) FEATURE:
        ( A ) NAME/KEY: modified_base
        ( B ) LOCATION: 34
        ( D ) OTHER INFORMATION: /mod_base=i ( x i ) SEQUENCE DESCRIPTION: SEQ ID NO:27:

GCGAATTCCN ATNGGNTGGG AYGCNTTYGG NCTNCC  36

( 2 ) INFORMATION FOR SEQ ID NO:28:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 20
        ( D ) OTHER INFORMATION: /mod_base=i ( i x ) FEATURE:
        ( A ) NAME/KEY: modified_base
        ( B ) LOCATION: 23
        ( D ) OTHER INFORMATION: /mod_base=i ( i x ) FEATURE:
        ( A ) NAME/KEY: modified_base
        ( B ) LOCATION: 26
        ( D ) OTHER INFORMATION: /mod_base=i ( i x ) FEATURE:
        ( A ) NAME/KEY: modified_base
        ( B ) LOCATION: 29
        ( D ) OTHER INFORMATION: /mod_base=i ( x i ) SEQUENCE DESCRIPTION: SEQ ID NO:28:

GCGAATTCAC YTGYTCRTTN GCNAGNACNG T  31

( 2 ) INFORMATION FOR SEQ ID NO:29:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 3
    ( D ) OTHER INFORMATION: /mod_base=i ( i x ) FEATURE:
    ( A ) NAME/KEY: modified_base
    ( B ) LOCATION: 6
    ( D ) OTHER INFORMATION: /mod_base=i ( i x ) FEATURE:
    ( A ) NAME/KEY: modified_base
    ( B ) LOCATION: 9
    ( D ) OTHER INFORMATION: /mod_base=i ( i x ) FEATURE:
    ( A ) NAME/KEY: modified_base
    ( B ) LOCATION: 21
    ( D ) OTHER INFORMATION: /mod_base=i ( i x ) FEATURE:
    ( A ) NAME/KEY: modified_base
    ( B ) LOCATION: 24
    ( D ) OTHER INFORMATION: /mod_base=i ( i x ) FEATURE:
    ( A ) NAME/KEY: modified_base
    ( B ) LOCATION: 27
    ( D ) OTHER INFORMATION: /mod_base=i ( x i ) SEQUENCE DESCRIPTION: SEQ ID NO:29:

CCNMTNGGNT WYCAYTGYAC NGGNMTNCC 29

( 2 ) INFORMATION FOR SEQ ID NO:30:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i x ) FEATURE:
    ( A ) NAME/KEY: modified_base
    ( B ) LOCATION: 12
    ( D ) OTHER INFORMATION: /mod_base=i ( i x ) FEATURE:
    ( A ) NAME/KEY: modified_base
    ( B ) LOCATION: 18
    ( D ) OTHER INFORMATION: /mod_base=i ( i x ) FEATURE:
    ( A ) NAME/KEY: modified_base
    ( B ) LOCATION: 24
    ( D ) OTHER INFORMATION: /mod_base=i ( i x ) FEATURE:
    ( A ) NAME/KEY: modified_base
    ( B ) LOCATION: 27
    ( D ) OTHER INFORMATION: /mod_base=i ( i x ) FEATURE:
    ( A ) NAME/KEY: modified_base
    ( B ) LOCATION: 30
    ( D ) OTHER INFORMATION: /mod_base=i ( x i ) SEQUENCE DESCRIPTION: SEQ ID NO:30:

GCRTCRTART ANGGRTTNGC RTCNGTNGTN ACRAA            35

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 6
        ( D ) OTHER INFORMATION: /mod_base=i ( i x ) FEATURE:
        ( A ) NAME/KEY: modified_base
        ( B ) LOCATION: 12
        ( D ) OTHER INFORMATION: /mod_base=i ( i x ) FEATURE:
        ( A ) NAME/KEY: modified_base
        ( B ) LOCATION: 18
        ( D ) OTHER INFORMATION: /mod_base=i ( i x ) FEATURE:
        ( A ) NAME/KEY: modified_base
        ( B ) LOCATION: 21
        ( D ) OTHER INFORMATION: /mod_base=i ( x i ) SEQUENCE DESCRIPTION: SEQ ID NO:31:

TTYMTNGARG TNGARACNCC NATGATG            27

( 2 ) INFORMATION FOR SEQ ID NO:32:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 9
        ( D ) OTHER INFORMATION: /mod_base=i ( i x ) FEATURE:
        ( A ) NAME/KEY: modified_base
        ( B ) LOCATION: 12
        ( D ) OTHER INFORMATION: /mod_base=i ( i x ) FEATURE:
        ( A ) NAME/KEY: modified_base
        ( B ) LOCATION: 15
        ( D ) OTHER INFORMATION: /mod_base=i ( i x ) FEATURE:
        ( A ) NAME/KEY: modified_base
        ( B ) LOCATION: 24
        ( D ) OTHER INFORMATION: /mod_base=i ( x i ) SEQUENCE DESCRIPTION: SEQ ID NO:32:

TARAAYTCNA TNGTNGTRAA YTCNGGRTTR TG            32

( 2 ) INFORMATION FOR SEQ ID NO:33:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i x ) FEATURE:
        ( A ) NAME/KEY: modified_base
        ( B ) LOCATION: 9

( D ) OTHER INFORMATION: /mod_base=i ( i x ) FEATURE:
              ( A ) NAME/KEY: modified_base
              ( B ) LOCATION: 15
              ( D ) OTHER INFORMATION: /mod_base=i ( i x ) FEATURE:
              ( A ) NAME/KEY: modified_base
              ( B ) LOCATION: 24
              ( D ) OTHER INFORMATION: /mod_base=i ( x i ) SEQUENCE DESCRIPTION: SEQ ID NO:33:

TACMAYTCNA KCATNGTRAA YTCNGGRTTR TG                                             32

( 2 ) INFORMATION FOR SEQ ID NO:34:

( i ) SEQUENCE CHARACTERISTICS:
              ( A ) LENGTH: 29 base pairs
              ( B ) TYPE: nucleic acid
              ( C ) STRANDEDNESS: single
              ( D ) TOPOLOGY: linear ( i x ) FEATURE:
              ( A ) NAME/KEY: modified_base
              ( B ) LOCATION: 15
              ( D ) OTHER INFORMATION: /mod_base=i ( i x ) FEATURE:
              ( A ) NAME/KEY: modified_base
              ( B ) LOCATION: 21
              ( D ) OTHER INFORMATION: /mod_base=i ( x i ) SEQUENCE DESCRIPTION: SEQ ID NO:34:

AARAARTAYG AYCTNGARGC NTGGTTYCC                                                 29

( 2 ) INFORMATION FOR SEQ ID NO:35:

( i ) SEQUENCE CHARACTERISTICS:
              ( A ) LENGTH: 29 base pairs
              ( B ) TYPE: nucleic acid
              ( C ) STRANDEDNESS: single
              ( D ) TOPOLOGY: linear ( i x ) FEATURE:
              ( A ) NAME/KEY: modified_base
              ( B ) LOCATION: 6
              ( D ) OTHER INFORMATION: /mod_base=i ( i x ) FEATURE:
              ( A ) NAME/KEY: modified_base
              ( B ) LOCATION: 15
              ( D ) OTHER INFORMATION: /mod_base=i ( i x ) FEATURE:
              ( A ) NAME/KEY: modified_base
              ( B ) LOCATION: 21
              ( D ) OTHER INFORMATION: /mod_base=i ( x i ) SEQUENCE DESCRIPTION: SEQ ID NO:35:

AARACNTAYG AYCTNGARGT NTGGATHCC                                                 29

( 2 ) INFORMATION FOR SEQ ID NO:36:

( i ) SEQUENCE CHARACTERISTICS:
              ( A ) LENGTH: 23 base pairs
              ( B ) TYPE: nucleic acid
              ( C ) STRANDEDNESS: single
              ( D ) TOPOLOGY: linear ( i x ) FEATURE:
              ( A ) NAME/KEY: modified_base
              ( B ) LOCATION: 9
              ( D ) OTHER INFORMATION: /mod_base=i (x i) SEQUENCE DESCRIPTION: SEQ ID NO:36:

CCYTTYTCNG TYTGRTARTT YTC  23

(2) INFORMATION FOR SEQ ID NO:37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i x) FEATURE:
        (A) NAME/KEY: modified_base
        (B) LOCATION: 9
        (D) OTHER INFORMATION: /mod_base=i (x i) SEQUENCE DESCRIPTION: SEQ ID NO:37:

CCRTCYTCNG TYTGRTARTT YTC  23

(2) INFORMATION FOR SEQ ID NO:38:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i x) FEATURE:
        (A) NAME/KEY: modified_base
        (B) LOCATION: 3
        (D) OTHER INFORMATION: /mod_base=i (i x) FEATURE:
        (A) NAME/KEY: modified_base
        (B) LOCATION: 12
        (D) OTHER INFORMATION: /mod_base=i (i x) FEATURE:
        (A) NAME/KEY: modified_base
        (B) LOCATION: 21
        (D) OTHER INFORMATION: /mod_base=i (x i) SEQUENCE DESCRIPTION: SEQ ID NO:38:

SCNTGTTTTM GNTCWGAAGC NGG  23

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i x) FEATURE:
        (A) NAME/KEY: modified_base
        (B) LOCATION: 6
        (D) OTHER INFORMATION: /mod_base=i (x i) SEQUENCE DESCRIPTION: SEQ ID NO:39:

TATMGNGAAA TTTCWTGTTC WAAT  24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i x) FEATURE:
        (A) NAME/KEY: modified_base ( B ) LOCATION: 19
              ( D ) OTHER INFORMATION: /mod_base=i ( x i ) SEQUENCE DESCRIPTION: SEQ ID NO:40:

TAAWGAACAW GAAATTTCNA KATA                                                          24

( 2 ) INFORMATION FOR SEQ ID NO:41:

( i ) SEQUENCE CHARACTERISTICS:
              ( A ) LENGTH: 23 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:41:

CCATCHKSTT GTTGATRATT TTC                                                           23

( 2 ) INFORMATION FOR SEQ ID NO:42:

( i ) SEQUENCE CHARACTERISTICS:
              ( A ) LENGTH: 29 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:42:

CGTGGATCCG TGAAAGAATA CAAAGACAC                                                     29

( 2 ) INFORMATION FOR SEQ ID NO:43:

( i ) SEQUENCE CHARACTERISTICS:
              ( A ) LENGTH: 32 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:43:

CCCAGTCGAC TTATCATCGC TCTTTTAAAA CC                                                 32

( 2 ) INFORMATION FOR SEQ ID NO:44:

( i ) SEQUENCE CHARACTERISTICS:
              ( A ) LENGTH: 29 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:44:

CGTGGATCCA TGCAAAAATC ACTGATCAC                                                     29

( 2 ) INFORMATION FOR SEQ ID NO:45:

( i ) SEQUENCE CHARACTERISTICS:
              ( A ) LENGTH: 31 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:45:

CCCAGTCGAC TTAGCTGATC AAACTTCCTG C                                                  31

( 2 ) INFORMATION FOR SEQ ID NO:46:

( i ) SEQUENCE CHARACTERISTICS:
              ( A ) LENGTH: 32 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:46:

GCGCGGATCC ATGGATTTTA TCAATATAGA AA  32

( 2 ) INFORMATION FOR SEQ ID NO:47:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

ACGCGTCGAC TTATGCGATA ACAAAATTAA CG  32

( 2 ) INFORMATION FOR SEQ ID NO:48:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

GCGCGGATCC ATGAAACAAG AACCCACCAC CT  32

( 2 ) INFORMATION FOR SEQ ID NO:49:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

ACGCGTCGAC TTATGGTTGT TTTAACAAAT C  31

( 2 ) INFORMATION FOR SEQ ID NO:50:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

GCGCGGATCC ATGATTGATA GAAAACTTTT AT  32

( 2 ) INFORMATION FOR SEQ ID NO:51:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

ACGCGTCGAC TTAAAGGTAT TTTTCTAACG C  31

( 2 ) INFORMATION FOR SEQ ID NO:52:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

```
GCGCGGATCC ATGTTTTCTA ACCAATACAT C                                                          31
```

( 2 ) INFORMATION FOR SEQ ID NO:53:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

```
ACGCGTCGAC TTATTCTCCA CTCTCTCCAC A                                                          31
```

( 2 ) INFORMATION FOR SEQ ID NO:54:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

```
GCGCTCTAGA TATCTGCTTA TGTCCCTAT ACTAGGTTAT TGG                                              43
```

( 2 ) INFORMATION FOR SEQ ID NO:55:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

```
GGGGTACCTC ACGATGCGGC CGCTCGAG                                                              28
```

( 2 ) INFORMATION FOR SEQ ID NO:56:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

```
CCGCTCGAGC GATGCAATGT CGATCAATTG TGC                                                        33
```

( 2 ) INFORMATION FOR SEQ ID NO:57:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

```
GGGGTACCCC TTTTTCATGA CCTCATATTC G                                                          31
```

( 2 ) INFORMATION FOR SEQ ID NO:58:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:58:

```
CAGACGTCTA GATATCTGCT TATGTTTTCT AACCAATAC                                                  39
```

( 2 ) INFORMATION FOR SEQ ID NO:59:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:59:

ACCGCTCGAG CGGTTATTCT CCACTCTCCA CATT                 34

( 2 ) INFORMATION FOR SEQ ID NO:60:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:60:

CAGACGTCTA GATATCTGCT TATGGCGGCC GTGCAGGCG            39

( 2 ) INFORMATION FOR SEQ ID NO:61:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:61:

TCTAGCTCGA GCTACACAGA AGTGCCAACT GTT                  33

( 2 ) INFORMATION FOR SEQ ID NO:62:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:62:

CCAAGAAGCT TGAAGTAATA ATAGGCGCAT GC                   32

( 2 ) INFORMATION FOR SEQ ID NO:63:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:63:

CGTACTGCAG GATTGTATGC TTGGTATAGC                      30

( 2 ) INFORMATION FOR SEQ ID NO:64:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:64:

GGAATTCTGA AAACAACTCA TATAAATACG                      30

(2) INFORMATION FOR SEQ ID NO:65:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (xi) SEQUENCE DESCRIPTION: SEQ ID NO:65:

GAGGCGCCCT CTTATCAATC CCTCCTCAA CC          32

(2) INFORMATION FOR SEQ ID NO:66:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (xi) SEQUENCE DESCRIPTION: SEQ ID NO:66:

CAGACGTCTA GATATCTGCT TATGCAAAAA TCACTGATCA          40

(2) INFORMATION FOR SEQ ID NO:67:

(i) SEQUENCE CHARACTERISTICS:
    (A) LENGTH: 12 amino acids
    (B) TYPE: amino acid
    (C) STRANDEDNESS: Not Relevant
    (D) TOPOLOGY: linear (xi) SEQUENCE DESCRIPTION: SEQ ID NO:67:

Arg Val Glu Asn Lys Ser Thr Arg Ala Ala Ala Ser
 1           5                   10

HELICOBACTER AMINOACYL-TRNA SYNTHETASE PROTEINS, NUCLEIC ACIDS AND STRAINS COMPRISING SAME

BACKGROUND OF THE INVENTION

H. pylori is a gram-negative, microaerophilic bacterium that infects the gastric mucosa of humans, and is one of the most common infections in humans worldwide. In industralized countries, about 50% of population is infected with H. pylori during their lifetime, and in nonindustrialized countries, this ratio is even higher (for review, see Goodwin, C. S. and B. W. Worsley (eds.), 1993, *Helicobacter pylori: Biology and Clinical Practice*, (CRC Press, Boca Raton, Fla.); Hunt, R. H. and G. N. J. Tytgat (eds.), 1994, *Helicobacter pylori: Basic Mechanisms to Clinical Cure*, (Kluwer Academic Publishers, Dordrecht, Netherlands).

H. pylori infection has been invariably found associated with chronic gastritis (Warren, J. D. and B. J. Marshall, *Lancet i:* 1273–1275 (1983); Marshall, B. J. and J. R. Warren, *Lancet ii:* 1311–1314 (1984)). Administration of Helicobacter species to humans and to animals leads to development of gastritis (Marshall, B. J. et al., *Med. J. Aust.* 142: 436–439 (1985); Morris, A. and G. Nicholson, *Am. J. Gastroenterol.* 82: 192–199 (1987); Krakowka, S. et al., *Infect. Immun.* 55: 2789 (1987)). H. pylori infection is also responsible for about 80% of gastric ulcers, and almost 100% of duodenal ulcers. Successful treatment of the infection leads to healing of the diseases (Coghlan, J. G. et al., *Lancet ii:* 1109–1111 (1987); Labenz, J. et al., *Am. J. Gastroenterol.*, 88: 491–495 (1993). In addition, various studies found that H. pylori infection increases gastric cancer by 4 to 6-fold (Correa, P., *Cancer Research* 52: 6735–6740 (1992); Nomura, A. et al., *N. Engl. J. Med.*, 325: 1132–1136 (1991); Parsonnet, J. et al., *J. Natl. Cancer Inst.*, 83: 640–643 (1991)).

The current most commonly used therapies to eradicate H. pylori infection are so-called triple therapies, in which patients are administered two different antibiotics and an anti-acid secretion drug simultaneously (for review, see O'Morain, C. and H. Lamouliatte, 1994, "Eradication", In: The year in Helicobacter pylori, P. Malfertheiner et al., (Eds.), (Current Science Ltd., London, UK) pp. 46–52). The efficacy of the therapies varies from clinical center to clinical center. Resistance to current antibiotics, in particular to metronidazole and other commonly used antibiotics for eradication of H. pylori infection, is well documented (for review, see Goodwin, C.S., 1993, "The susceptibility of Helicobacter pylori to antibiotics", In: *Helicobacter pylori: biology and clinical practice*, Goodwin, C. S. and B. W. Worsley (Eds.), (CRC Press, Boca Raton, Fla.) pp. 343–349). In addition, side effects of current antibiotic therapies are quite common and sometimes cause termination of the therapies before complete healing of the infection. Because of the development of resistance to antibiotics and adverse side-effects of current therapies for helicobacter infection, there is a continuing need for new drug targets and new antibiotics.

SUMMARY OF THE INVENTION

The invention relates to isolated and/or recombinant nucleic acids which encode aminoacyl-tRNA synthetases of helicobacter origin. The invention also relates to recombinant DNA constructs and vectors containing DNA having a sequence which encodes an aminoacyl-tRNA synthetase of helicobacter origin, or portions of the enzyme. These nucleic acids and constructs can be used to produce recombinant aminoacyl-tRNA synthetases of helicobacter origin.

A further embodiment of the invention is antisense nucleic acid which can hybridize to the nucleic acid which encodes an aminoacyl-tRNA synthetase of helicobacter. In cells, antisense nucleic acid can inhibit the function of an RNA which encodes an aminoacyl-tRNA synthetase of helicobacter.

The invention also relates to proteins or polypeptides, referred to herein as isolated and/or recombinant helicobacter aminoacyl-tRNA synthetases. These proteins are useful in the identification of inhibitors of aminoacyl-tRNA synthetase function (including inhibitors having antimicrobial activity), in biochemical separations of the amino acid which they specifically recognize, and in quantitations of the amino acid and ATP. Antibodies which bind to these enzymes can be made and can be used in the purification and study of the enzyme.

The recombinant helicobacter aminoacyl-tRNA synthetases can be produced in host cells using cells and methods described herein. Tester strains, which are cells engineered to rely on the function of the tRNA synthetase encoded by an introduced cloned gene, are also an embodiment of the invention. Tester strains can be used to test the effectiveness of drug candidates in the inhibition of the essential tRNA synthetase enzyme encoded by the introduced cloned gene. In this way, potential inhibitors of the enzyme can be screened for antimicrobial or antibiotic effects, without requiring the culture of pathogenic strains of helicobacter, such as *Helicobacter pylori*.

DETAILED DESCRIPTION OF THE INVENTION

Figure 1:
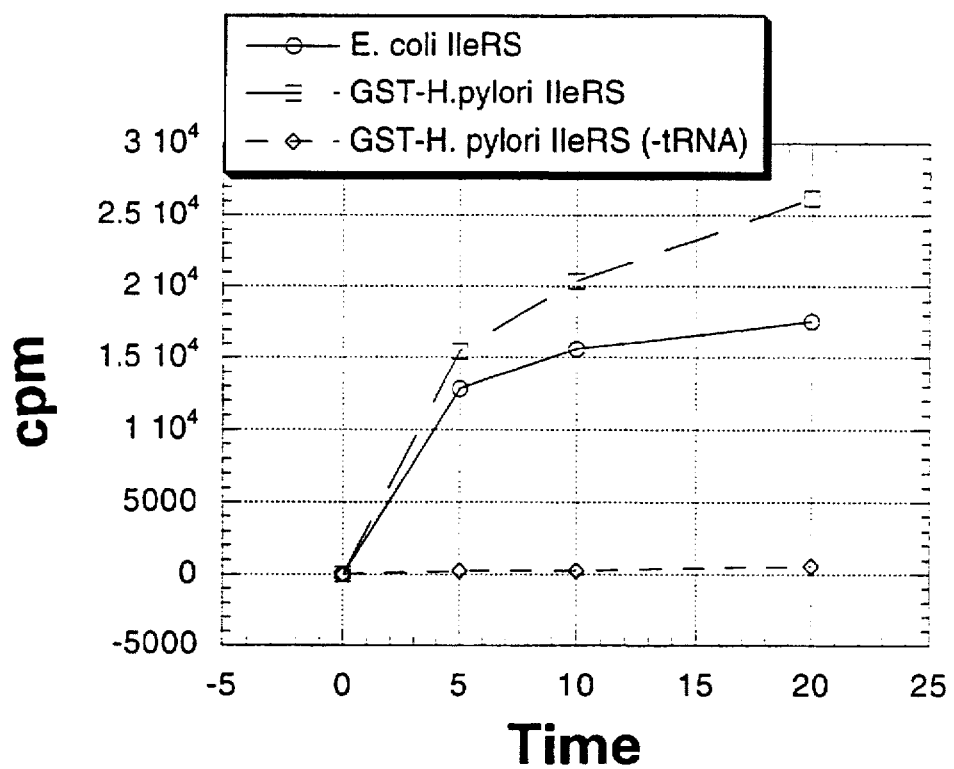
FIG. 1 is a graph illustrating the aminoacylation activity (cpm, counts per minute of [³H]isoleucyl-tRNA) over time (minutes) of the GST-*H. pylori* Ile tRNA synthetase as compared with that of purified *E. coli* Ile tRNA synthetase, using crude total *E. coli* tRNA as a substrate (Example 6). O, *E. coli* IleRS; □, GST-*H. pylori* Ile tRNA synthetase; ◊, GST-*H. pylori*-Ile tRNA synthetase minus tRNA.

The aminoacyl-tRNA synthetases are enzymes with the common general function of catalyzing the following reaction:

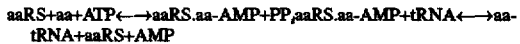

(aaRS=aminoacyl-tRNA synthetase; aa=amino acid; ATP=adenosine 5'-triphospate; AMP=adenosine 5'-monophosphate; PP$_i$=inorganic pyrophosphate) The second (aminoacylation) step is often referred to as "charging" the tRNA.

Generally, in each bacterial organism, there are 20 aminoacyl-tRNA synthetases, each specific for a different amino acid. Eucaryotic organisms also typically encode 20 cytoplasmic aaRSs, one specific for each amino acid. In addition, eucaryotic organisms generally encode a separate set of mitochondrial aaRSs. In the yeast *Saccharomyces cerevisiae*, the cytoplasmic and mitochondrial enzymes are encoded by separate nuclear genes, with the exception of histidyl- and valyl-tRNA synthetases (Natsoulis, G., et al. Cell 46:235–243 (1986); Chatton, B. et al., *J. Biol. Chem.* 263:52–57 (1988)). Each aminoacyl-tRNA synthetase enzyme recognizes and reacts with a specific amino acid and with one or more tRNAs that recognize the codons specific for that amino acid (cognate tRNAs). The specificity of the aaRS for the amino acid is determined by protein-amino acid interactions, and the specificity of the aaRS for the tRNA is determined by protein-RNA interactions, using different sites on the aaRS.

The tRNA synthetases can be subdivided into two groups of enzymes, class I and class II, based on short regions of sequence homology as well as distinct active site core tertiary structures (Eriani, G., et al., *Nature* 347:203–206 (1990); Moras, D., *Trends Biochem. Sci.* 17:159–164 (1992)). The twenty-one aminoacyl-tRNA synthetases from *E. coli* have been divided into two classes (see, e.g., Burbaum, J. J. and P. Schimmel, *J. Biol Chem.* 266(26):16965–16968 (1991)).

Nucleic Acids, Constructs and Vectors

The present invention relates to isolated and/or recombinant (including, e.g., essentially pure) nucleic acids having sequences which encode a helicobacter aminoacyl-tRNA synthetase, or a portion of a helicobacter aminoacyl-tRNA synthetase. In one embodiment, the nucleic acid or portion thereof encodes a protein or polypeptide having at least one function characteristic of a helicobacter aminoacyl-tRNA synthetase specific for a selected amino acid, such as a catalytic activity (e.g., catalysis of aminoacyl-adenylate formation, catalysis of aminoacylation of a tRNA with the amino acid), and/or binding function (e.g., tRNA-, amino acid- or ATP-binding), and/or antigenic function (e.g., binding of antibodies that also bind to non-recombinant helicobacter aaRS), and/or oligomerization function. Oligomerization activity is the ability of a protein subunit or protein fragment to bind together with one or more other protein subunits or protein fragments, thus altering the quaternary structure of the resulting complex. For example, "adhesive" fragments with oligomerization activity can bind to another fragment with no catalytic activity of its own to restore or partially restore enzymatic activity (Jasin, M., et al., U.S. Pat. No. 4,952,501). The present invention also relates more specifically to isolated and/or recombinant nucleic acids or a portion thereof having sequences which encode an aminoacyl-tRNA synthetase of *Helicobacter pylori* origin, or a portion thereof.

The invention further relates to isolated and/or recombinant nucleic acids that are characterized by (1) their ability to hybridize to (a) a nucleic acid encoding a helicobacter aminoacyl-tRNA synthetase specific for a selected amino acid, such as a nucleic acid having the sequence of SEQ ID NO:1 (having a GTG initiation codon as shown, or an ATG initiation codon as appropriate), SEQ ID NO:3, SEQ ID NO:5, SEQ ID NO:7, SEQ ID NO:9 or SEQ ID NO:11, (b) the complement of any one of (a), or (c) portions of either of the foregoing (e.g., a portion comprising the open reading frame); or (2) by their ability to encode a polypeptide having the amino acid sequence of a helicobacter aminoacyl-tRNA synthetase (e.g., SEQ ID NO:2, SEQ ID NO:4, SEQ ID NO:6, SEQ ID NO:8, SEQ ID NO:10 or SEQ ID NO:12), or functional equivalents thereof (e.g., a polypeptide which aminoacylates the isoaccepting cognate aminoacyl-tRNAs (such as tRNA$^{Ile}$, tRNA$^{Met}$, tRNA$^{Leu}$, tRNA$^{Val}$, tRNA$^{Lys}$ or tRNA$^{Ser}$ of *H. pylori*) with a selected amino acid); or (3) by both characteristics. In one embodiment, the percent amino acid sequence similarity between the polypeptides encoded by SEQ ID NO:2, 4, 6, 8, 10, and 12, and the respective functional equivalents of these polypeptides is at least about 80% (≧80%). In a preferred embodiment, the percent amino acid sequence similarity between the polypeptides encoded by SEQ ID NO:2, 4, 6, 8, 10, and 12, and their respective functional equivalents is at least about 85% (≧85%). More preferably, the percent amino acid sequence similarity between the polypeptides encoded by SEQ ID NO:2, 4, 6, 8, 10, and 12, and their respective functional equivalents is at least about 90%, and still more preferably, at least about 95%.

Isolated and/or recombinant nucleic acids meeting these criteria comprise nucleic acids having sequences identical to sequences of naturally occurring helicobacter aaRS genes and portions thereof, or variants of the naturally occurring sequences. Such variants include mutants differing by the addition, deletion or substitution of one or more residues, modified nucleic acids in which one or more residues are modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for sequence similarity.

Isolated and/or recombinant nucleic acids that are characterized by their ability to hybridize to (a) a nucleic acid encoding a helicobacter aminoacyl-tRNA synthetase (for example, those nucleic acids depicted in SEQ ID NO:1, SEQ ID NO:3, SEQ ID NO:5, SEQ ID NO:7, SEQ ID NO:9, and SEQ ID NO:11, (b) the complement of such nucleic acids, (c) or a portion thereof (e.g. under high or moderate stringency conditions), may further encode a protein or polypeptide having at least one function characteristic of a helicobacter aminoacyl-tRNA synthetase specific for a selected amino acid, such as a catalytic activity (e.g., aminoacyladenylate formation, aminoacylation of a tRNA with amino acid), binding function (e.g., tRNA-, amino acid-, or ATP-binding), antigenic function (e.g., binding of antibodies that also bind to non-recombinant helicobacter aaRS), and/or oligomerization function. The catalytic or binding function of a protein or polypeptide encoded by hybridizing nucleic acid may be detected by standard enzymatic assays for activity or binding (e.g., assays which monitor aminoacyladenylate formation, aminoacylation of tRNA). Functions characteristic of the aminoacyl-tRNA synthetase may also be assessed by in vivo complementation activity or other suitable methods. Enzymatic assays, complementation tests, or other suitable methods can also be used in procedures for the identification and/or isolation of nucleic acids which encode a polypeptide such as a polypeptide of the amino acid sequence SEQ ID NO:2, SEQ ID NO:4, SEQ ID NO:6, SEQ ID NO:8, SEQ ID NO:10 or SEQ ID NO:12, or functional equivalents of these polypeptides. The antigenic properties of proteins or polypeptides encoded by hybridizing nucleic acids can be determined by immunological methods employing antibodies that bind to a helicobacter aminoacyl-tRNA synthetase, such as immunoblot, immunoprecipitation and radioimmunoassay.

Nucleic acids of the present invention can be used in the production of proteins or polypeptides. For example, DNA containing all or part of the coding sequence for a helicobacter aminoacyl-tRNA synthetase such as lysyl-tRNA synthetase, or DNA which hybridizes to DNA having the sequence SEQ ID NO:9, can be incorporated into various constructs and vectors created for further manipulation of sequences or for production of the encoded polypeptide in suitable host cells. For expression in E. coli and other organisms, a GTG initiation codon can be altered to ATG as appropriate.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501. The aminoacyl-tRNA synthetases are known to have different quaternary structures, including both monomeric and multimeric structures (e.g., homodimers, tetramers and heteromultimeric $\alpha_2\beta_2$ forms). Thus, as used herein, a nucleic acid which encodes a portion of a helicobacter aminoacyl-tRNA synthetase can also refer to one of two or more distinct subunits of said tRNA synthetase.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In a particular embodiment, the antisense nucleic acid is wholly or partially complementary to and can hybridize with a target nucleic acid, wherein the target nucleic acid can hybridize to a nucleic acid having the sequence of the complement of the top strand shown in SEQ ID NO:1, SEQ ID NO:3, SEQ ID NO:5, SEQ ID NO:7, SEQ ID NO:9, or SEQ ID NO:11). For example, antisense nucleic acid can be complementary to a target nucleic acid having the sequence shown as the top strand of the open reading frame in SEQ ID NO:1, SEQ ID NO:3, SEQ ID NO:5, SEQ ID NO:7, SEQ ID NO:9, or SEQ ID NO:11, or to a portion thereof sufficient to allow hybridization. In another embodiment, the antisense nucleic acid is wholly or partially complementary to and can hybridize with a target nucleic acid which encodes a helicobacter aminoacyl-tRNA synthetase.

H. pylori is the most important human pathogen among helicobacter species. Because advances in the understanding and treatment of H. pylori infection would be of tremendous benefit, it was the species selected for most of the experimental work described herein. As described in the Exemplification, PCR fragments of H. pylori aaRS genes were isolated, cloned and used as probes to screen an ordered cosmid genomic library of H. pylori (Bukanov, N. O. and D. E. Berg, Mol. Microbiol. 11(3): 509–523 (1994)). Nucleic acids encoding complete aminoacyl-tRNA synthetases from H. pylori were isolated and characterized. These isolated genes, encoding isoleucyl-, methionyl-, leucyl-, valyl-, lysyl- and seryl-tRNA synthetases, are representatives of a broader class of helicobacter aminoacyl-tRNA synthetase genes, including synthetase genes encoding enzymes specific for each amino acid and derived from various species of helicobacter. These additional genes can also be used to express helicobacter aminoacyl-tRNA synthetases, with utilities corresponding to those described herein, and can be used in the production of host cells and tester strains comprising recombinant helicobacter aminoacyl-tRNA synthetase genes using methods described herein. The approaches described herein, including, but not limited to, the approaches to isolate and manipulate the isoleucyl-, methionyl-, leucyl-, valyl-, lysyl- and seryl-tRNA synthetase genes of H. pylori, to construct vectors and host strains, and to produce and use the proteins, to produce antibodies, etc., can be applied to other members of the genus Helicobacter, including, but not limited to, pathogenic species such as H. cinaedi and H. fennelliae, intestinal organisms which cause diarrheal illnesses (particularly in HIV-infected individuals), H. mustelae (in ferrets), H. felis (in dogs and cats), H. muridarum (in mice), H. nemestrinae (in nonhuman primates), and H. acinonyx (in cheetahs). For example, the H. pylori aminoacyl-tRNA synthetase genes described here, or sufficient portions thereof, whether isolated and/or recombinant or synthetic, including fragments produced by PCR, can be used as probes or primers to detect and/or recover homologous genes of the other helicobacter species (e.g., by hybridization, PCR or other suitable techniques). Similarly, genes encoding *H. pylori* aminoacyl-tRNA synthetases specific for other amino acids can be isolated from an ordered cosmid library, other genomic libraries (e.g., libraries constructed in λgt11 and pbluescript SK as described by Covaccio et al., *Proc. Natl. Acad. Sci. USA*, 90: 5791–5795 (1993), or lambda ZAPII as described by Evans et al., *J. Bacteriol.*, 175: 674–683 (1993) and Tummuru et al., *Infection and Inmunity*, 61: 1799–1809 (1993) ) or other Helicobacter libraries, according to methods described herein or other suitable methods.

Proteins

The invention also relates to proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in cells. "Isolated" proteins or polypeptides include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein or portion thereof has at least one function characteristic of a helicobacter aminoacyl-tRNA synthetase specific for a selected amino acid, for example, catalytic activity (e.g., catalysis of aminoacyl-adenylate formation, catalysis of aminoacylation of a tRNA with amino acid), binding function (e.g., tRNA-, amino acid-, or ATP-binding), antigenic function (e.g., binding of antibodies that also bind to non-recombinant helicobacter aminoacyl-tRNA synthetase), and/or oligomerization activity. As such, these proteins are referred to as aminoacyl-tRNA synthetases of helicobacter origin or helicobacter aminoacyl-tRNA synthetases, and include, for example, naturally occurring helicobacter aminoacyl-tRNA synthetases, variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues.

In a particularly preferred embodiment, like naturally occurring helicobacter aminoacyl-tRNA synthetases, isolated and/or recombinant helicobacter aminoacyl-tRNA synthetases of the present invention aminoacylate the isoaccepting cognate tRNAs of the helicobacter organism with a selected amino acid in a two-step reaction. For example, in the case of *H. pylori*, an isolated, recombinant lysyl-tRNA synthetase is able to aminoacylate each of the isoaccepting species of cognate tRNA$^{Lys}$ of *H. pylori* with lysine. In the first step, the lysyl-tRNA synthetase catalyzes the covalent linkage of lysine to ATP to form an adenylate complex (lysyl-adenylate) with the release of pyrophosphate, and, in a second step, catalyzes the covalent linkage of lysine to a specific tRNA recognized by the enzyme, releasing AMP.

The invention further relates to fusion proteins, comprising a helicobacter aminoacyl-tRNA synthetase (as described above) as a first moiety, linked to second moiety not occurring in the helicobacter aaRS as found in nature. Thus, the second moiety can be an amino acid or polypeptide. The first moiety can be in an N-terminal location, C-terminal location or internal to the fusion protein. In one embodiment, the fusion protein comprises a *H. pylori* aminoacyl-tRNA synthetase as the first moiety, and a second moiety comprising a linker sequence and affinity ligand.

Fusion proteins can be produced by a variety of methods. For example, a fusion protein can be produced by the insertion of an aaRS gene or portion thereof into a suitable expression vector, such as Bluescript SK +/– (Stratagene), pGEX-4T-2 (Pharmacia) and pET-15b (Novagen). The resulting construct is then introduced into a suitable host cell for expression. Upon expression, fusion protein can be purified from a cell lysate by means of a suitable affinity matrix (see e.g., Current Protocols in *Molecular Biology* (Ausubel, F. M. et al., eds., Vol. 2, Suppl. 26, pp. 16.4.1–16.7.8 (1991)).

The invention also relates to isolated and/or recombinant portions of an aminoacyl-tRNA synthetase of helicobacter origin. For example, a portion of an aminoacyl-tRNA synthetase can also refer to one of two or more distinct subunits of said tRNA synthetase. Portions of the enzyme can be made which have full or partial function on their own, or which when mixed together (though fully, partially, or nonfunctional alone), spontaneously assemble with one or more other polypeptides to reconstitute a functional protein having at least one function characteristic of an aminoacyl-tRNA synthetase. (See, e.g., Shiba, K. and Schimmel, P., *J. Biol. Chem.* 267:22703–22706 (1992) for an example of three inactive peptides from *E. coli* IleRS spontaneously assembling in vivo to reconstitute active enzyme; see also, Burbaum, J. and Schimmel, P., *Biochemistry* 30(2): 319–324 (1991), describing non-overlapping segments of *E. coli* MetRS that can fold together to reconstitute an active enzyme capable of recognizing and charging tRNA in vitro and in vivo; see also Jasin, M. et al. (U.S. Pat. No. 4,952, 501) describing deletion studies of *E. coli* alanyl-tRNA synthetase which showed that large portions of the protein were unnecessary for specific aminoacylation activity.) Based on this type of analysis, portions of a helicobacter aaRS can be made which have at least one function characteristic of a helicobacter aminoacyl-tRNA synthetase, such as a catalytic function, binding function, antigenic function and/or oligomerization function. Studies on the structure and function of the aaRSs provide the basis for being able to divide the helicobacter aaRS enzymes into functional domains (Schimmel, P., *Current Biology* 1:811–816 (1991)).

The sequences and structures of the catalytic domains of several tRNA synthetases which have been purified and studied led to the identification of two distinct classes designated class I and class II (Schimmel, P., *Ann. Rev. Biochem.* 56:125–158 (1987); Webster, T. A., et al., *Science* 226:1315–1317 (1984); Eriani, G. et al , *Nature* 347:203–206 (1990) and Cusack, S., et al., *Nature* 347:249–255 (1990)). Class I enzymes have a well-conserved N-terminal nucleotide binding fold responsible for amino acid binding, aminoacyl-adenylate formation, and tRNA acceptor helix docking. The N-terminal nucleotide binding fold is comprised of alternating β-strands and α-helices. The C-terminal domain is rich in α-helices and contains residues needed for interactions with the parts of the tRNA distal to the amino acid attachment site (Shepard, A., et al., *Proc. Natl. Acad. Sci. U.S.A.* 89:9964–9968 (1992); Hou, Y.-M.,et al., *Proc. Natl. Acad. Sci. U.S.A.* 88:976–980 (1991)). Five enzymes--cysteinyl-, isoleucyl-, leucyl-, methionyl-, and valyl-tRNA synthetases--have been grouped together because they are more closely related in sequence and arrangement of their domains to each other than to the other five members of class I (Hou, Y.-M., et al., *Proc. Natl. Acad. Sci. U.S.A.* 88:976–980 (1991); Eriani, G., et al., *Nucleic Acids Res.* 19:265–269 (1991)). Furthermore, the C-terminal domains of isoleucyl-, leucyl-, methionyl-, cysteinyl- and valyl-tRNA synthetases appear to have a common origin, which is distinct from the C-terminal domain found in other class I enzymes (Shiba, K., et al., *Proc. Natl. Acad. Sci. USA* 89:1880–1884 (1992); Shepard, A., et al., *Proc. Natl. Acad. Sci. U.S.A.* 89:9964–9968 (1992)). In *E. coli*, these five enzymes of class I vary in size from 461 to 951 amino acids and are active as monomers. The size variation is in large part explained by the variability in the lengths of the two insertions designated connective polypeptide 1 (CP1), which is inserted between the second α-helix and third β-strand of the nucleotide binding fold, and CP2, which is placed between the third a-helix and fourth β-strand (Starzyk, R. M., et al., *Science* 237:1614–1618 (1987)). In all of these enzymes, CP1 is the larger of the two insertions and varies in *E. coli* from 61 in cysteinyl-tRNA synthetase to 300 amino acids in isoleucyl-tRNA synthetase (Hou, Y.-M., et al., *Proc. Natl. Acad. Sci. USA* 88:976–980 (1991)). While a portion of CP1 may be deleted from isoleucyl-tRNA synthetase without loss of function (Starzyk, R. M., et al., *Science* 237:1614–1618 (1987)), this insertion is known to facilitate acceptor helix interactions in the related glutaminyl-tRNA synthetase whose three dimensional structure in complex with tRNA$^{Gln}$ has been determined by X-ray crystallography (Rould, M. A et al., *Science* 246:1135–1142 (1989)). In some tRNA synthetases, this second domain interacts directly with the anticodon (Rould, M. A. et al., *Science* 246:1135–1142 (1989) and Cavarelli, J., et al., *Nature* 362:181–184 (1993)), while in other enzymes there is no contact made between the second domain and the anticodon (Biou, V.,et al., *Science* 263:1404–1410 (1994)). To a first approximation, the two domains in class I tRNA synthetases interact with the two distinct domains of the L-shaped tRNA structure. Thus, the recognition elements of the tRNA synthetase and of the tRNA which are needed for the operational RNA code are segregated into discrete protein and RNA domains.

The primary sequence of the class II enzymes is generally characterized by three conserved motifs. These motifs are designated in the order they occur in the sequence as motif 1, motif 2, and motif 3. Although the motifs have a conserved core, they vary in length and are marked by as little as a single invariant amino acid residue. The motif sequences are defined as follows:

Motif 1: gΦxxΦxxPΦΦ
Motif 2: (F/Y/H)Rx(E/D)(4–12x)(R/H)xxxFxxx(D/E)
Motif 3: λxΦgΦgΦeRΦΦΦΦΦ

The abbreviations are: x, variant; Φ, hydrophobic; and λ, small amino acids. Lower case letters indicate that the amino acid is partially conserved. None of these motifs are found in the class I family. With the exception of *E. coli* Gly- and Phe-tRNA synthetases which only contain a discernible motif 3, class II enzymes characterized to date incorporate all three motifs (Ribas de Pouplana, L. et al., *Protein Science* 2:2259–2262 (1993)).

The second class of tRNA synthetases was firmly defined when the crystal structure of the *E. coli* Ser-tRNA synthetase active site was shown to have no relationship to the Rossmann fold of class I enzymes (Cusack, S. C., et al., *Nature* 347:249–255 (1990)). X-ray diffraction investigations with an ATP-bound Ser-tRNA synthetase co-crystal from *T. ther-* *mophilus* revealed the details of a novel ATP binding site (Cusack, S., et al., *In The Translational Apparatus,* K. H. Nierhaus et al., eds., Plenum Press, New York, pp. 1–9, 1993; Belrhali, H., et al., *Science* 263:1432–1436 (1994); Biou, V., et al., *Science* 263:1404–1410 (1994)).

Motif 3 is comprised of a β-strand followed by an α helix and is characterized by a GLER sequence. This motif is the only one that has been universally detected in all of the class II enzymes studied. The crystal structures of yeast Ser- and Asp- (Ruff, M. S. et al., *Science* 252:1682–1689 (1991)) tRNA synthetases suggest a role for motif 3 in amino acid and ATP binding. Mutations in this region have resulted in a reduction in binding and/or a high $K_m$ for amino acid or ATP binding (Eriani, G., et al., *Nature* 347:203–206 (1993); Anselme, J. and Härtlein, M., *FEBS Lett.* 280:163–166 (1991); Kast, P. and Hennecke, H., *J. Mol. Biol.,* 222:99–124 (1991); Kast, P. et al., *FEBS Lett.* 293:160–163 (1991); Lanker, S., et al., *Cell* 70:647–657 (1992)).

Yeast Asp-tRNA synthetase was the first class II enzyme to be co-crystallized with its cognate tRNA (Ruff, M., et al., *Science* 252:1682–1689 (1991)). The yeast Asp-tRNA synthetase contains a nucleotide binding structure similar to that found in Ser-tRNA synthetase. The combination of these two class II crystal structures provides a model for the active sites of all of the class II tRNA synthetases.

Because motif 1 is at the dimer interface in the crystal structures of yeast Asp-tRNA synthetase (Ruff, M. S., et al., *Science* 252:1682–1689 (1991)), *E. coli* Ser-tRNA synthetase (Cusack, S., et al., *Nature* 347:249–255 (1990); Cusack, S., et al., *In The Translational Apparatus,* K. H. Nierhaus et al., eds., Plenum Press, New York, pp. 1–9, 1993; Price, S., et al., *FEBS Lett.* 324:167–170 (1993)) and *T. thermophilus* Ser-tRNA synthetase (Cusack, S., et al., *In The Translational Apparatus,* K. H. Nierhaus et al., eds., Plenum Press, New York, pp. 1–9, 1993; Belrhali, H., et al., *Science* 263:1432–1436 (1994); Biou, V., et al., *Science* 263:1404–1410 (1994)), motif 1 was thought to be important for dimerization. This motif was identified in the N-terminal region of *E. coli* Ala-tRNA synthetase (Ribas de Pouplana, et al., *Protein Science* 2:2259–2262 (1993)), but a series of deletion mutations had also previously demonstrated that a region at the C-terminus of the protein is needed for oligomerization (Jasin, M., et al., *Nature* 306:441–447 (1983); Jasin, et al., *Cell* 36:1089–1095 (1984)). Thus, motif 1 is not sufficient for oligomerization of this enzyme.

An idiographic representation of the predicted eight-stranded β-structure with three a-helices of the *E. coli* Ala-tRNA synthetase has been constructed (Ribas de Pouplana, L., et al., *Protein Science* 2:2259–2262 (1993)); Shi, J.-P., et al., *Biochemistry* 33:5312–5318 (1994)).

Collectively, over 40 mutations in motif 2 and the region between motif 2 and 3 were individually constructed and tested (Davis, M. W., et al., *Biochemistry* 33:9904–9911 (1994); Shi, J.-P., et al., *Biochemistry* 33:5312–5318 (1994)). These mutations were mostly at conserved residues with chemical functional groups. Although motif 2 is of a different size and has only two identical amino acid residues with its counterpart in yeast Asp- and *T. thermophilus* Ser-tRNA synthetases, the mutational analysis of this motif can be explained in terms of those structures, and shows the importance of predicted motif 2 for adenylate synthesis (Ribas de Pouplana, L., et al., *Protein Science* 2:2259–2262 (1993)). A study of the products of random mutagenesis of this region also demonstrated the importance of motif 2 for adenylate transfer (Lu, Y. and Hill, K. A. W., *J. Biol. Chem.* 269:12137–12141 (1994)). Mutagenesis of specific residues in motif 2 of *E. coli* Ala-tRNA synthetase and mutagenesis of their predicted counterparts in motif 2 of yeast Asp-tRNA synthetase yielded similar results with regard to loss of function (Cavarelli, J., et al., *EMBO J.* 13:327–337 (1994); Davis, M. W., et al., Biochemistry 33:9904–9911 (1994)). Evidence was obtained for sequence context determining how the energy of adenylate binding is partitioned between ground and transition states in the two enzymes. In addition, a conserved aspartate residue among Ala-tRNA synthetases at the beginning of motif 3 was shown to be important for the adenylate synthesis and particularly for the adenylate transfer reaction (Davis, M. W., et al., *Biochemistry* 33:9904–9911 (1994)). The functional significance of motif 3 for adenylate synthesis has been demonstrated by mutagenesis in the yeast Asp-tRNA synthetase system (Cavarelli, J., et al., *EMBO J.* 13:327–337 (1994)).

Upon consideration of this information, with the remaining teachings of the specification, *H. pylori* tRNA synthetase derivatives can be constructed which possess at least one function characteristic of a helicobacter aminoacyl-tRNA synthetase.

Method of Producing Recombinant aaRSs

Another aspect of the invention relates to a method of producing a helicobacter aminoacyl-tRNA synthetase or a portion thereof, and to expression systems and host cells containing a vector appropriate for expression of a helicobacter aminoacyl-tRNA synthetase.

Cells that express a recombinant aminoacyl-tRNA synthetase or a portion thereof can be made and maintained in culture to produce protein for isolation and purification. These cells can be procaryotic or eucaryotic. Examples of procaryotic cells that can be used to express helicobacter aminoacyl-tRNA synthetases include *Escherichia coli*, *Bacillus subtilis* and other bacteria. Examples of eucaryotic cells that can be used to express the aminoacyl-tRNA synthetases include yeasts such as *Saccharomyces cerevisiae*, *S. pombe*, *Pichia pastoris*, and other lower eucaryotic cells, as well as cells of higher eucaryotes, such as those from insects and mammals. (See, e.g., Ausubel, F. M. et al., eds. *Current Protocols in Molecular Biology*, Greene Publishing Associates and John Wiley & Sons Inc., (1993)).

To make host cells that produce a recombinant aaRS protein or portion thereof for isolation and purification, as a first step the gene encoding the enzyme can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for aminoacyl-tRNA synthetase operably linked to one or more expression control sequences whereby the coding sequence is under the control of transcription signals and linked to appropriate translation signals to permit translation of the aaRS, portion thereof, or of a fusion protein comprising an aaRS or portion thereof. As a second step, the vector can be introduced into cells by a method appropriate to the type of host cells (e.g., transformation, electroporation, infection). In a third step, for expression from the aaRS gene, the host cells can be maintained under appropriate conditions, e.g., in the presence of inducer, normal growth conditions, etc.).

As a particular example of the above approach to producing active helicobacter aminoacyl-tRNA synthetase, a gene encoding the *H. pylori* aaRS can be integrated into the genome of a virus that enters the host cells. By infection of the host cells, the components of a system which permits the transcription and translation of the helicobacter aaRS gene are present in the host cells. Alternatively, an RNA polymerase gene, inducer, or other component required to complete such a gene expression system may be introduced into the host cells already containing the helicobacter aaRS gene, for example, by means of a virus that enters the host cells and contains the required component. The aaRS gene can be under the control of an inducible or constitutive promoter. The promoter can be one that is recognized by the host cell RNA polymerase. The promoter can, alternatively, be one that is recognized by a viral RNA polymerase and is transcribed following infection of the host cells with a virus.

Antibodies

The invention further relates to antibodies that bind to an isolated and/or recombinant helicobacter aminoacyl-tRNA synthetase, including portions of antibodies (e.g., a peptide), which can specifically recognize and bind to the tRNA synthetase. These antibodies can be used in methods to purify the enzyme or portion thereof by various methods of immunoaffinity chromatography, or to selectively inactivate one of the enzyme's active sites, or to study other aspects of enzyme structure, for example.

The antibodies of the present invention can be polyclonal or monoclonal, and the term antibody is intended to encompass both polyclonal and monoclonal antibodies. Antibodies of the present invention can be raised against an appropriate immunogen, including proteins or polypeptides of the present invention, such as an isolated and/or recombinant helicobacter aminoacyl-tRNA synthetase or portion thereof, or synthetic molecules, such as synthetic peptides. The immunogen, for example, can be a protein having at least one function of a helicobacter aminoacyl-tRNA synthetase, as described herein.

The term antibody is also intended to encompass single chain antibodies, chimeric, humanized or primatized (CDR-grafted) antibodies, as well as chimeric or CDR-grafted single chain antibodies, comprising portions from more than one species. For example, the chimeric antibodies can comprise portions of proteins derived from two different species, joined together chemically by conventional techniques or prepared as a contiguous protein using genetic engineering techniques (e.g., DNA encoding the protein portions of the chimeric antibody can be expressed to produce a contiguous protein chain). See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology*, 10: 1455–1460 (1992), regarding primatized antibody, and Ladner et al., U.S. Pat. No. 4,946,778 and Bird, R. E. et al., *Science*, 242: 423–426 (1988)) regarding single chain antibodies.

Whole antibodies and biologically functional fragments thereof are also encompassed by the term antibody. Biologically functional antibody fragments which can be used include those fragments sufficient for binding of the antibody fragment to a helicobacter aaRS to occur, such as Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Alternatively, antibodies can be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Preparation of immunizing antigen, and polyclonal and monoclonal antibody production can be performed using any suitable technique. A variety of methods have been described (see e.g., Kohler et al., Nature, 256: 495–497 (1975) and Eur. J. Immunol. 6: 511–519 (1976); Milstein et al., Nature 266: 550–552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those obtained from the spleen or lymph nodes, are obtained from animals immunized with the antigen of interest. The fused cells (hybridomas) are isolated using selective culture conditions, and cloned by limiting dilution. Cells which produce antibodies with the desired specificity can be selected by a suitable assay (e.g., ELISA).

Assays for Inhibitors and Tester Strains

The enzymatic assays, binding assays, and construction of tester strains described below, which rely upon the nucleic acids and proteins of the present invention, can be used, alone or in combination with each other or other suitable methods, to identify inhibitors of one or more helicoabacter aminoacyl-tRNA synthetases.

Enzyme Assay

Upon the isolation of an aaRS gene from helicobacter (as described herein), the gene can be incorporated into an expression system for production of the aaRS or a fusion protein, followed by isolation and testing of the enzyme in vitro. The isolated or purified helicobacter aaRSs can also be used in further structural studies that allow for the design of antibiotics which specifically target one or more aaRSs of helicobacter, while not affecting or minimally affecting host or mammalian (e.g., human) aaRSs. Because the amino acid sequences of the tRNA synthetases have diverged over evolution, significant differences exist between the structure of the enzymes from mammals (e.g., human, bovine) and mammalian pathogens, and the design or selection of inhibitors can exploit the structural differences between the pathogen aaRS and the host (e.g., a mammalian host, such a human) aaRS to yield specific inhibitors of the pathogen aaRS, which may further have antimicrobial activity.

Furthermore, isolated, active helicobacter aaRSs can be used in an in vitro method of screening for inhibitors of aminoacyl-tRNA synthetase activity in which the inhibitory effect of a compound is assessed by monitoring aaRS activity according to standard techniques. For example, inhibitors of the activity of isolated, recombinant H. pylori IleRS, MetRS, LeuRS, ValRS, LysRS or SerRS can be identified by the method. In one embodiment, the isolated aaRS enzyme is maintained under conditions suitable for aminoacyl-adenylate formation, the enzyme is contacted with a compound to be tested, and formation of the aminoacyl-adenylate is monitored by standard assay. A reduction in the activity measured in the presence of compound, as compared with the activity in the absence of compound, is indicative of inhibition of aminoacyl-tRNA synthetase activity by the compound. For example, the extent of isoleucyl-adenylate formation catalyzed by urified IleRS can be measured using an ATP-pyrophosphate exchange assay in the presence and in the absence of a candidate inhibitor (Calendar, R. and P. Berg, Biochemistry, 5:1690–1695 (1966)). In this reaction, the enzymatic synthesis of ATP from AMP and pyrophosphate in the absence of tRNA is monitored. A candidate inhibitor can be added to a suitable reaction mixture (e.g., 100 mM TrisCl, pH 7.5 / 5 mM $MgCl_2$ / 10 mM 2-mercaptoethanol/ 10 mM KF / 2 mM ATP / 2 mM [$^{32}$p] pyrophosphate / 1 mM isoleucine), and the mixture is incubated at 25° C. IleRS (to a final concentration of ~10 nM) is added to initiate the reaction. Aliquots of the reaction are removed at various times and quenched in 7% (vol/vol) cold perchloric acid, followed by the addition of 3% (wt/vol) charcoal suspended in 0.5% HCl. The ATP adsorbed to charcoal is filtered onto glass fiber pads (Schleicher & Schuell), and formation of [$^{32}$P]ATP is quantified by liquid scintillation counting in Hydrofluor (National Diagnostics, Manville, N.J.). The enzyme activity measured in the presence of the compound is compared with the activity in the absence of the compound to assess inhibition. Alternatively, a candidate inhibitor can be preincubated with enzyme under suitable conditions. Preincubation in the absence of substrate provides a more sensitive assay for the detection of inhibition (e.g., detects slow binding inhibitors). For example, the compound can be added to a mixture containing ~10 nM isoleucyl-tRNA synthetase in 100 mM TrisCl, pH 7.5 / 5 mM $MgCl_2$ / 10 mM 2-mercaptoethanol/ 10 mM KF, and preincubated at 25° C. for 20 minutes. To initiate the reaction, ATP, [$^{32}$P] pyrophosphate and isoleucine are added to final concentrations of 2 mM, 2 mM and 1 mM, respectively. The reaction is monitored as described above, and the activity measured in the presence of compound is compared with the activity in the absence of compound to assess inhibition.

In another embodiment, formation of the aminoacylated tRNA is monitored in a standard aminoacylation assay. Inhibitors identified by enzymatic assay can be further assessed for antimicrobial activity using tester strains as described herein, or using other suitable assays. For example, the extent of aminoacylation of tRNA with isoleucine catalyzed by IleRS (e.g., a GST fusion) can be measured by monitoring the incorporation of [$^3$H] isoleucine into trichloroacetic acid-precipitable [$^3$H] isoleucyl-tRNA in the presence of a candidate inhibitor, as compared with activity in the absence inhibitor. Appropriately diluted IleRS (~0.4 nM) can be preincubated for 20 minutes at 25° C. in, for example, 50 mM HEPES, pH 7.5 / 0.1 mg/ml BSA (bovine serum albumin) / 10 mM $MgCl_2$ / 10 mM 2-mercaptoethanol / 20 mM KCl / 1–20% DMSO (preferably about 1%) in the presence or absence of a compound to be tested. The preincubation mixture can be supplemented with ATP, [$^3$H]isoleucine and tRNA to final concentrations of, for example, 4 mM ATP/ 20 μM [$^3$H] isoleucine (0.6 μCi), and 90 μM crude tRNA or 2 μM specific $tRNA^{Ile}$. The reaction can be maintained at 25° C., and aliquots are removed at specific times, and applied to filter paper discs (3 MM, Whatman) that have been pre-soaked with 5% (wt/vol) trichloroacetic acid. Filters are washed for three 10-minute periods in 5% trichloroacetic acid, rinsed in 95% ethanol and 100% ether, and the incorporation of $^3$H-isoleucine into tRNA (formation of $^3$H-Ile-tRNA) is measured in Betafluor by liquid scintillation counting. The aminoacylation assay can also be performed without preincubation under suitable conditions (e.g., using ~0.4 nM IleRS in a reaction mixture containing 50 mM HEPES, pH 7.5 / 0.1 mg/ml BSA (bovine serum albumin) / 10 mM $MgCl_2$ / 10 mM 2-mercaptoethanol / 20 mM KCl / 1–20% DMSO / 4 mM ATP/ 20 μM [$^3$H]isoleucine (0.6 μCi), and 90 μM crude tRNA or 2 μM specific $tRNA^{Ile}$) in the presence or absence of test compound. An $IC_{50}$ value (the concentration of inhibitor causing 50% inhibition of enzyme activity) for a known amount of active IleRS can be determined.

Binding Assay

Isolated, recombinant aaRS or a portion thereof, and suitable fusion proteins can be used in a method to select and identify compounds which bind specifically to the aaRS, such as *H. pylori* isoleucyl-, methionyl-, leucyl-, valyl-, lysyl- or seryl-tRNA synthetase, and which are potential inhibitors of aaRS activity. Compounds selected by the method can be further assessed for their inhibitory effect on aaRS activity and for antimicrobial activity.

In one embodiment, an isolated or purified *H. pylori* aaRS can be immobilized on a suitable affinity matrix by standard techniques, such as chemical cross-linking, or via an antibody raised against the isolated or purified aaRS, and bound to a solid support. The matrix can be packed in a column or other suitable container and is contacted with one or more compounds (e.g., a mixture) to be tested under conditions suitable for binding of compound to the aaRS. For example, a solution containing compounds can be made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more substrates or substrate analogs which can disrupt binding of compound to the aaRS, such as lysine, ATP, tRNA$^{Lys}$ for a lysyl-tRNA synthethase, or other suitable molecules which competitively inhibit binding).

Fusion proteins comprising all of, or a portion of, the aaRS linked to a second moiety not occurring in the helicobacter aaRS as found in nature (see above), can be prepared for use in another embodiment of the method. Suitable fusion proteins for this purpose include those in which the second moiety comprises an affinity ligand (e.g., an enzyme, antigen, epitope). The fusion proteins can be produced by the insertion of an aaRS gene or portion thereof into a suitable expression vector, which encodes an affinity ligand (e.g., pGEX-4T-2 and pET-15b, encoding glutathione S-transferase and His-Tag affinity ligands, respectively). The expression vector is introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

In one aspect of this embodiment, the fusion protein is immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the aaRS portion of the bound fusion protein. Next, the affinity matrix with bound fusion protein is washed with a suitable wash buffer to remove unbound compounds and non-specifically bound compounds. Compounds which remain bound can be released by contacting the affinity matrix with fusion protein bound thereto with a suitable elution buffer (a compound elution buffer). Wash buffer is formulated to permit binding of the fusion protein to the affinity matrix, without significantly disrupting binding of specifically bound compounds. In this aspect, compound elution buffer is formulated to permit retention of the fusion protein by the affinity matrix, but is formulated to interfere with binding of the compound (s) tested to the aaRS portion of the fusion protein. For example, a change in the ionic strength or pH of the elution buffer can lead to release of compounds, or the elution buffer can comprise a release component or components designed to disrupt binding of compounds to the aaRS portion of the fusion protein (e.g., one or more substrates or substrate analogs which can disrupt binding of compounds to the aaRS portion of the fusion protein, such as lysine, ATP, or tRNA$^{Lys}$ for LysRS, or other suitable molecules which competitively inhibit binding).

Immobilization can be performed prior to, simultaneous with, or after contacting the fusion protein with compound, as appropriate. Various permutations of the method are possible, depending upon factors such as the compounds tested, the affinity matrix-ligand pair selected, and elution buffer formulation. For example, after the wash step, fusion protein with compound bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

To enrich for specific binding to the aaRS portion of the fusion protein, compounds can be pre-treated, for example with affinity matrix alone, with affinity ligand or a portion thereof (e.g., the portion present in the fusion protein), either alone or bound to matrix, under conditions suitable for binding of compound to the aaRS portion of the bound fusion protein.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also Rebek et al., Process for Creating Molecular Diversity, U.S. Ser. No. 08/180,215, filed Jan. 12, 1994, relating to compounds without tags; see also, Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

Random sequence RNA and DNA libraries (see Ellington, A. D. et al., *Nature* 346: 818–822 (1990); Bock, L. C. et al., *Nature* 355: 584–566 (1992); and Szostak, J. W., *Trends in Biochem. Sci.* 17:89–93 (March, 1992)) can also be screened according to the present method to select RNA or DNA molecules which bind to a helicobacter aaRS. Such molecules can be further assessed for antimicrobial effect upon introduction into a cell (e.g., by expression in the case of an RNA molecule selected by the method).

Tester Strains

Nucleic acids of the present invention can also be used in constructing tester strains for in vivo assays of the effect on the activity of the helicobacter enzyme of a substance which is added to tester strain cells. A tester strain comprises a host cell having a defect in a gene encoding an endogenous aaRS, and a heterologous aaRS gene which complements the defect in the host cell gene. Thus, complementation of a particular defective host cell aaRS gene by a heterologous aaRS gene is a threshold requirement for a tester strain. Because the aaRS genes are essential, the heterologous gene can be introduced into the host cell simultaneously with inactivation of the host cell gene to preserve viability. Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

If the heterologous gene complements the inactivated host cell gene, such a cell can be used to determine whether a substance that is introduced into the cells for testing, can interact specifically with the heterologous tRNA synthetase (or a component in the pathway of the expression of the heterologous tRNA synthetase gene) to cause loss of function of the tested heterologous tRNA synthetase in those host cells. Thus, such cells are "tester strains". Successful cross-species complementation has been described already, for example, for yeast seryl-tRNA synthetase and for yeast isoleucyl-tRNA synthetase in *E. coli* (Weygand-Durasevic, I., et al., *Eur. J. Biochem* 214:869–877 (1993); Racher, K. I., et al., *J. Biol. Chem.* 266:17158–17164 (1991)).

In tester cells to be used in an assay for chemical substances that can inhibit the function of a specific aaRS, the gene for the aminoacyl-tRNA synthetase can, for example, physically replace the host cell aaRS gene or can be present in addition to a host aaRS gene that does not produce a functional product, and the heterologous gene whose gene product is to be tested complements the host gene. A substance to be tested is administered to the tester cells, and the viability or growth of such cells can be compared with that of cells of a suitable control.

As a tester strain comprises a host cell comprising a heterologous aaRS gene (i.e., one from a heterologous species), a suitable host cell is heterologous with respect to the species from which the gene to be tested is isolated. For instance, suitable host cells to test *Helicobacter pylori* genes can be host cells of a species other than *H. pylori*. Examples of species which are suitable for use as hosts for the construction of tester strains are *E. coli*, *S. cerevisiae*, and *B. subtilis*. These species are especially amenable to genetic manipulation because of their history of extensive study.

Suitable host cells having a genotype useful for the construction of a tester strain can be constructed or selected using known methods. For example, both in *E. coli* and in *S. cerevisiae*, a first plasmid which contains a functional copy of a host chromosomal aaRS gene (which is to be inactivated later), and some selectable marker gene, can be constructed and introduced into cells. Then, an inactivating mutation can be caused in the chromosomal copy of the aaRS gene.

This can be accomplished, for instance, by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin et al., U.S. Pat. No. 4,713,337; Schimmel, P., U.S. Pat. No. 4,963,487; Toth, M. J. and Schimmel, P., *J. Biol. Chem.* 261:6643–6646 (1986); Rothstein, R., *Methods in Enzymology* 194:281–301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS.

A test plasmid which is compatible with the maintenance plasmid, and which contains the aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluoroorotic acid to select against *S. cerevisiae* cells which have a first plasmid containing the URA3 gene), cells which survive by virtue of having a complementing aaRS gene on the second plasmid can be selected (Sikorsky, R. S. and Boeke, J. D., *Methods in Enzymology* 194:302–318 (1991)).

Causing or selecting for a double crossover event which creates a deletion and insertion can be used in itself as a one-step method of constructing a tester strain in which a native aaRS gene is replaced by the corresponding foreign gene whose gene product is to be tested. Endogenous recombination mechanisms have been used to advantage previously in *E. coli*, *B. subtilis*, and *S. cerevisiae*, among other organisms. This method depends on the ability of the heterologous gene to be tested to complement the native corresponding aaRS gene. This can be done by introducing into the cells double-stranded DNA having regions of homology to the DNA flanking the target native aaRS gene, and having between these regions a gene encoding a selectable marker as well as the heterologous aaRS gene intended to replace the native aaRS gene. The survival of cells expressing the selectable marker is indicative of expression of the introduced heterologous aaRS gene and complementation of the defect in the endogenous synthetase.

For example, a tester strain useful for testing the effect of a compound on the function of LeuRS expressed by an inserted *H. pylori* gene, can be constructed in a one-step method in a suitable host cell. Optional positive and negative controls for this cross-species transformation can be used to show that the resulting strain depends on the LeuRS gene from *H. pylori* for growth and that this recombination event is not lethal. For example, *B. subtilis* cells made competent for transformation (Dubnau, D. and Davidoff-Abelson, R., *J. Mol. Biol.* 56:206–221 (1971)) can be transformed with a suitable construct, such as a linearized plasmid containing an insert. Generally, the construct includes a selectable marker gene for antibiotic resistance, or other suitable selectable marker. In one embodiment, a linearized plasmid which contains the *H. pylori* LeuRS gene and an antibiotic resistance gene, situated between sequences homologous to the flanking sequences of the endogenous LeuRS gene of the host cells, is used to transform the host cell. For a positive control, the linearized plasmid can be constructed in a similar fashion, except that the native *B. subtilis* LeuRS gene replaces the *H. pylori* gene, such that a normal *B. subtilis* LeuRS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous LeuRS gene. Successful construction of a tester strain can also be confirmed by Southern analysis.

B. subtilis strains, which can be used as hosts for gene replacement (Dubnau, D. and Davidoff-Abelson, R., J. Mol. Biol. 56:209-221 (1971)), contain a cryptic tyrosyl-tRNA synthetase gene (tyrz) in addition to the tyrs gene, which can maintain viability (Glaser, P. et al., DNA Sequ. and Mapping, 1:251-61 (1990); Henken, T.M et al., J. Bacteriol., 174:1299-1306 (1992)). A suitable tester strain for TyrRS can be constructed in B. subtilis by, for example, simultaneous inactivation of both of the host genes, or by sequential inactivation. For instance, inactivation of one host gene by a suitable method, such as by insertion of a selectable marker, can be followed by a one-step gene replacement of the remaining host gene with a heterologous helicobacter TyrRS gene and a second selectable marker.

The yeast S. cerevisiae offers additional possibilities for genetic manipulations to create tester strains, relative to bacteria. Yeast integrating plasmids, which lack a yeast origin of replication, can be used for making alterations in the host chromosome (Sikorski, R. S. and Heiter, P., Genetics, 122:19-27 (1989); Gietz, R. D. and Sugino, A., Gene, 74:527-534 (1988)). In another embodiment, one-step gene disruptions can be performed in diploid cells using a DNA fragment comprising a copy of an aaRS gene (optionally containing a deletion in the aaRS gene) having an insertion of a selectable marker in the aaRS gene. A suitable fragment can be introduced into a diploid cell to disrupt a chromosomal copy of the yeast gene. Successful integration of the disrupted aaRS gene can be confirmed by Southern blotting and by tetrad analysis of the sporulated diploid cells. The diploid cells heterozygous for the disrupted aaRS gene provide a diploid host strain which can be transformed with a plasmid containing the heterologous aaRS gene. These cells can be sporulated and the haploid spores analyzed for rescue of the defective chromosomal aaRS by the heterologous aaRS gene.

Alternatively, those diploid cells that are found to contain one copy of the disrupted chromosomal aaRS gene, as well as one functional copy, can be transformed with a maintenance plasmid which contains a gene which complements the disruption, such as the corresponding wild type yeast aaRS gene, and which provides for a mechanism to select against survival of the cells containing this plasmid. These cells can then be made to sporulate to obtain a haploid null strain containing the disrupted chromosomal aaRS gene and the wild type gene on the maintenance plasmid. This haploid host strain can then be transformed with a test plasmid which expresses a heterologous aaRS gene, and the maintenance plasmid can be selected against by growing this strain under appropriate conditions.

Construction of a tester strain may start with the isolation of a mutant host strain which produces e.g., an inactive tRNA synthetase specific for a particular amino acid, a tRNA synthetase which is conditionally inactivatible, or no tRNA synthetase at all specific for that amino acid. A number of E. coli and S. cerevisiae strains have been described that can be used for constructing tester strains. Some of these strains are described below for purposes illustration. The procedures used to isolate and/or construct these E. coli and S. cerevisiae strains, or similar procedures, can be used or dapted to make additional mutant strains in E. coli, S. cerevisiae or in other host organisms.

A number of E. coli strains have been characterized in which an aaRS gene has been inactivated by some method, in whole or in part, yielding an observable phenotypic defect which can be detectably complemented. For example, null strains in which the gene encoding MetRS has been inactivated, and a mutant strain of E. coli in which the gene encoding MetRS has been conditionally inactivated, have been described (see Kim, et al., Proc. Natl. Acad. Sci. USA 90:10046-10050 (1993), describing a metG null strain of E. coli carrying a maintenance plasmid, MN9261/pRMS615); and Barker, D. G. et al. Eur. J. Biochem. 127:449-457 (1982) and Starzyk, R. M. et al., Biochemistry, 28:8479-8484 (1989), regarding a mutant strain having a methionine auxotrophy because the $K_m$ for methionine of the enzyme encoded by the chromosomal metG allele is elevated).

E. coli strain IQ843/pRMS711 and its derivative IQ844/pRMS711 contain a chromosomal deletion of the ileS gene (ΔileS203::kan), and are propagated by expression of wild type IleRS at 30° C. from a temperature-sensitive maintenance plasmid designated pRMS711, which encodes the wild type ileS gene and a gene which confers chloramphenicol resistance. pRMS711 cannot replicate at 42° C., thus, at the non-permissive temperature, the maintenance plasmid is lost. Following the introduction of a test construct into these strains, the growth of chloramphenicol sensitive colonies at a non-permissive temperature (e.g., 42° C.) is indicative of complementation of the chromosomal ileS deletion by the introduced construct (Shiba, K. and P. Schimmel, Proc. Natl. Acad. Sci. USA, 89:1880-1884 (1992); Shiba, K. and P. Schimmel, Proc. Natl. Acad. Sci. USA, 89:9964-9968 (1992); Shiba, K. and P. Schimmel, J. Biol. Chem., 267:22703-22706 (1992)).

An E. coli strain has been constructed in which both genes encoding a lysyl-tRNA synthetase, lysS (Kawakami, K. et al., Mol. Gen. Genet. 219:333-340 (1989)) and lysU (Leveque, F. et al. Nucleic Acids Res. 18:305-312 (1990); Clark, R. L. and Neidhardt, F. C., J. Bacteriol. 172:3237-3243 (1990)), have been mutated. This strain carries a temperature sensitive maintainence plasmid that is lost at 42° C. (Chen, J. et al., J. Bacteriol. 176:2699-2705 (1994)).

Temperature sensitive alleles are examples of genes encoding conditionally inactivatable tRNA synthetases. For example, temperature-sensitive alleles of the genes encoding cytoplasmic IleRS (ils1-1) and MetRS (mes1-1) have been described in S. cerevisiae (Hartwell, L. H., and McLaughlin, C.S., J. Bacteriol. 96:1664-1671 (1968); McLaughlin, C.S., and Hartwell, L. H. Genetics 61:557-566 (1969)), and are available from the Yeast Genetic Stock Center (University of California-Berkeley; catalog nos. 341 and 19:3:4, respectively). Temperature sensitive strains of E. coli having a defect in the tyrs gene encoding TyrRS (see, e.g., Bedouelle, H. and G. Winter, Nature 320:371-373 (1986)) and temperature-sensitive serS (encoding SerRS) strains of E. coli have been described (Low, B., et al., J. Bacteriol. 108:742-750 (1971); Clarke, S. J. et al., J. Bacteriol. 113:1096-1103 (1973); and Hartlein, M. et al., Nucl. Acids Res., 15(3):1005-1017 (1987)).

Temperature-sensitive alas strains of E. coli have also been described (Buckel, P. et al, J. Bacteriol. 108:1008-1016 (1971); Lee, A. L. and Beckwith, J., J. Bacteriol. 166:878-883 (1986)), in addition to a number of strains with well-characterized alas deletions and complementing alas alleles on plasmids (Jasin, M., et al., Cell 36:1089-1095 (1984); Jasin, M. and Schimmel, P., J. Bacteriol. 159:783-786 (1984)). Such strains can be used as host cells for the construction of E. coli tester strains for alanyl-tRNA synthetase genes of helicobacter.

E. coli strains having a defect, such as a null mutation, in an aminoacyl-tRNA synthetase gene can be constructed using a cloned E. coli aaRS gene. Each aminoacyl-tRNA synthetase from E. coli has been cloned (see Meinnel, T. et al., 1995, "Aminoacyl-tRNA synthetases: Occurrence, structure and function", In: tRNA: *Structure, Biosynthesis and Function*, Söll, D. and U. RajBhandary, Eds., (American Society for Microbiology: Washington, D.C.), Chapter 14, pp. 251–292, the teachings of which are incorporated herein by reference). For example, the *E. coli* tyrosyl-tRNA synthetase gene (Barker, D. G., Eur. *J. Biochem.*, 125:357–360 (1982); Barker, D. G. et al., *FEBS Letters*, 150:419–423 (1982)), isoleucyl-tRNA synthetase gene (Webster, T. et al., *Science* 226:1315–1317 (1984); see also, EMBL/GenBank Accession No. D10483), and seryl-tRNA synthetase gene have been cloned and sequenced (Härtlein, M. et al., *Nucl. Acids Res.*, 15(3):1005–1017 (1987)). The cloned genes can also be used as maintenance plasmids in a suitable host cell or can be incorporated into a suitable construct for use as a maintenance plasmid.

For construction of a tester strain in *S. cerevisiae*, a plasmid such as the one reported by P. Walter et al. (*Proc. Natl. Acad. Sci. USA* 80:2437–2441, 1983), which contains the wild type cytoplasmic methionyl-tRNA synthetase gene of *S. cerevisiae*, MES1, can be used to construct mesl strains, and for the construction of maintenance plasmids to create cytoplasmic tester strains for a MetRS (see also Fasiolo, F. et al., *J. Biol. Chem.* 260:15571–15576 (1985)). The ILS1 gene encoding cytoplasmic isoleucyl-tRNA synthetase (Englisch, U., et al., *Biol. Chem. Hoppe-Seyler* 368:971–979 (1987)), and the KRS1 gene encoding cytoplasmic lysyl-tRNA synthetase (Mirande, M. et al., *Biochemie* 68:1001–1007 (1986); Mirande, M. and Waller, J.-P., *J. Biol. Chem.* 263:18443–18451 (1988)) of *S. cerevisiae* have been cloned and sequenced. The KRS1 gene was shown to be essential by the construction of a disrupted allele of KRS1 (Martinez, R. et al., *Mol. Gen. Genet.* 227:149–154 (1991)). The yeast VAS1 gene encodes both mitochondrial and cytoplasmic ValRSs (Chatton, B. et al., *J. Biol. Chem.*, 263(1):52–57 (1988)). Leucyl- and seryl-tRNA synthetase genes from yeast cytoplasm, among others, have also been cloned and sequenced and can be used in the construction of tester strains (see e.g., Weygand-Durasevic, L et al., *Nucl. Acids Res.*, 15(5):1887–1904 (1987) regarding *S. cerevisiae* serS; see also Meinnel, T. et al., 1995, "Aminoacyl-tRNA synthetases: Occurrence, structure and function", In: tRNA: Structure, Biosynthesis and Function, Söll, D. and U. RajBhandary, Eds., (American Society for Microbiology: Washington, D.C.), Chapter 14, pp. 251–292 and references cited therein).

Mitochondrial mutant strains, such as an msml-1 strain or disruption strain QBY43 (aW303ΔMSM1) (MATa ade2-1 his3-11, 15 leu2-3,112 ura3-1 trp1-1 msml::HIS3; see Tzagoloff, A., et al., *Eur. J. Biochem.* 179:365–371 (1989)), can be used for the construction of tester strains comprising a helicobacter methionyl-tRNA synthetase (see e.g., Example 10 for construction of a tester strain in a QBY43 derivative). Strains having a defect in another mitochondrial aminoacyl-tRNA synthetase can be constructed using a cloned mitochondrial aaRS gene, and used to make tester strains (see Meinnel, T. et al., 1995, "Aminoacyl-tRNA synthetases: Occurrence, structure and function", In: tRNA: Structure, Biosynthesis and Function, Söll, D. and U. RajBhandary, Eds., (American Society for Microbiology: Washington, D.C.), Chapter 14, pp. 251–292 and ATCC Catalog of Recombinant DNA Materials, American Type Culture Collection, Rockville, M.D., regarding mitochondrial aaRS genes; a sequence designated as mitochondrial IleRS has been recently reported (GenBank Accession No. L38957, locus YSCMSI1)). The sequence and disruption of the *S. cerevisiae* mitochondrial leucyl-tRNA synthetase gene (MSL1) has been reported (Tzagoloff, A. et al., *J. Biol Chem.*, 263:850–856 (1988)). An *S. cerevisiae* strain has been constructed which carries a disruption of MSY1, the gene encoding mitochondrial tyrosyl-tRNA synthetase. Plasmids carrying MSY1 which rescue this defect, also have been constructed (Hill, J. and A. Tzagoloff, Columbia University; see Edwards, H. and P. Schimmel, *Cell* 51:643–649 (1987)). The construction of a tester strain using the gene encoding *S. cerevisiae* mitochondrial lysyl-tRNA synthetase (Gatti, D. L. and A. Tzagoloff, *J. Mol. Biol.* 218:557–568 (1991); GenBank Accession No. X57360) is described in Example 9.

In *S. cerevisiae*, to construct a maintenance plasmid or a test plasmid carrying a heterologous gene, a suitable vector, such as a yeast centromere plasmid (CEN; single-copy) or 2 μ vector (high copy) can be used. A heterologous gene to be tested can also be incorporated into the chromosome, using an integrating plasmid, for example. Examples of convenient yeast vectors for cloning include vectors such as those in the pRS series (integrating, CEN, or 2 μplasmids differing in the selectable marker (HIS3, TRP1, LEU2, URA3); see Christianson, T. W., et al., *Gene*, 110:119–122 (1992) regarding 2 μ vectors; see Sikorski, R. S. and Hieter, P. *Genetics*, 122:19–27 (1989) regarding integrating and CEN plasmids which are available from Stratagene, La Jolla)) and shuttle vectors (integrating, CEN or 2 μ vectors) which contain the multiple cloning site of pUC19 (Gietz, R. D. and Sugino, A., *Gene*, 74:527–534 (1988)). Examples of expression vectors include pEG (Mitchell, D. A. et al., *Yeast*, 9:715–723 (1993)) and pDAD1 and pDAD2, which contain a GAL1 promoter (Davis, L. L and Fink, G. R., *Cell* 61:965–978 (1990)).

A variety of promoters are suitable for expression. Available yeast vectors offer a choice of promoters. In one embodiment, the inducible GAL1 promoter is used. In another embodiment, the constitutive ADH1 promoter (alcohol dehydrogenase; Bennetzen, J. L. and Hall, B. D., *J. Biol. Chem.*, 257:3026–3031 (1982)) can be used to express an inserted gene on glucose-containing media. An example of a vector suitable for expression of a heterologous aaRS gene in yeast is pQB169 (Example 11).

For illustration, a yeast tester strain can be constructed as follows. An *S. cerevisiae* strain with convenient markers, such as FY83 (MATa/MATα lys2-128δ/lys2-128δ leu2Δ/leu2Δl ura3-52/ura3-52 trp1 Δ63/trp1 Δ63) can be used as a host cell.

A clone encoding yeast cytoplasmic seryl-tRNA synthetase has been isolated (Weygand-Durasevic, L et al., *Nucl. Acids Research*, 15(5):1887–1904 (1987); GenBank/EMBL Data Bank, Accession No. X04884). A nucleic acid encoding yeast cytoplasmic SerRS can be used to create a null allele of the yeast cytoplasmic SerRS gene. For example, a deletion/insertion allele can be constructed by excising the SerRS open reading frame, including the promoter region and 3' flanking region or portions thereof from a cloned gene, and replacing the excised sequence with a selectable marker (e.g., TRP1). This serrs::TRP1 fragment can be used to transform the diploid strain FY83, and Trp+ transformants can be selected (Rothstein, J., *Methods in Enzymol.* 101:202–211 (1983)). Standard genetic procedures can be employed to identify the appropriate integrant created by this one-step gene disruption (a diploid having the genotype MATa/MATα lys2-128δ/lys2-128δ leu2 Δl/leu2Δ1 ura3-52/ura3-52 trp1 Δ63/trp1 Δ63 serrs::TRP1/TyrRS); Rose, M. D. et al. *Methods in Yeast Genetics*, 1990, Cold Spring Harbor Press, Cold Spring Harbor, N.Y.).

To construct a maintenance plasmid, a fragment from containing the SerRS coding region, its promoter and some of the 3' untranslated region (e.g., a region approximately equivalent to that deleted in the construction of the null allele above) can be excised and introduced into a vector such as YCplac33, a CEN plasmid containing a URA3 selectable marker (Gietz, R. D. and Sugino, A., *Gene* 74:527–534 (1988)). The resulting plasmid can be used to transform the serrs::TRP1/SerRS diploid described above, and Ura+ transformants which contain the maintenance plasmid can be selected. The resulting diploid can be sporulated and a haploid Trp+Ura+ spore (a SerRS null strain), corresponding to a serrs: :TRP1 strain dependent upon the URA3-SerRS maintenance plasmid can be isolated.

To construct a test plasmid (a plasmid bearing a heterologous tRNA synthetase gene to be tested for its ability to complement the defect in the endogenous yeast gene), a heterologous aaRS gene to be tested can be inserted into a suitable vector for expression. For instance, the multicopy vector pQB169 described in Example 11 can be used. A fragment containing the *H. pylori* SerRS gene can be inserted into pQB169, using one or more suitable restriction sites in the multiple cloning site, for example. Alternatively, to test whether a relatively reduced level of expression of the heterologous tRNA synthetase gene permits complementation, a fragment containing the *H. pylori* SerRS gene can be inserted into a CEN plasmid such as pQB172 for expression (Example 11). Preferably, the heterologous gene is inserted into the vector so that its ATG start codon is the first ATG within 50 to 100 bp of the transcription start site of the ADH promoter of the vector.

Because these plasmids bear the LEU2 selectable marker, they can be used to transform a null strain, such as the Trp+Ura+Leu− strain described, and Leu++transformants containing the test plasmid can be selected. Leu+Ura+Trp+ transformants (containing a serrs::TRP1 allele, a URA3 maintenance plasmid, and the LEU2 test plasmid) can be tested for growth on media containing 5-fluoroorotic acid (5-FOA). 5-FOA is toxic to URA3 cells, and causes loss of the URA3 maintenance plasmid (Boeke, J. et al., *Mol. Gen. Genet.*, 197:345–346 (1984)). Accordingly, growth of cells on media containing 5-FOA is indicative of complementation of the lethal deletion in the aaRS gene on the chromosome (serrs::TRP1) by the heterologous TyrRS gene on the test plasmid. Cells that are unable to grow on 5-FOA are dependent upon the maintenance plasmid for viability, and therefore, are indicative of insufficient activity to complement the lethal deletion in the aaRS gene. Where complementation is observed, the strain can be used to test for inhibitors of the product of the heterologous gene encoded by the test plasmid.

In another embodiment, a eucaryotic host cell is used to construct a mitochondrial tester strain. For example, in yeast, each of the mitochondrial tRNA synthetases is essential for growth on non-fermentable carbon sources (e.g., glycerol). Thus, complementation tests can be conducted in mitochondrial tester strains. As the genes encoding mitochondrial aminoacyl-tRNA synthetases are typically nuclear-encoded, the procedures described above can be modified to construct mitochondrial tester strains having a defect in a mitochondrial aminoacyl-tRNA synthetase. Modification is necessitated by the fact that yeast strains with a defect in mitochondrial protein synthesis, such as a defective aminoacyl-tRNA synthetase, lose their mitochondrial DNA, rapidly becoming rho−. As a result, these strains are unable to grow on non-fermentable carbon sources even if a complementing gene is introduced into the strain. Therefore, in a haploid strain having a defect in, for example, the yeast mitochondrial leucyl-tRNA synthetase gene (e.g., a gene disruption with a cosegregating selectable marker constructed as indicated above; see also Tzagoloff, A. et al., *J. Biol. Chem.* 263(2): 850–856 (1988)), the haploid strain can be crossed with a rho+ strain having a wild-type mitochondrial leucyl-tRNA synthetase gene to restore the mitochondrial DNA. The resulting rho+ diploid can then be transformed with a plasmid which encodes the wild-type yeast mitochondrial leucyl-tRNA synthetase (i.e., a maintenance plasmid) and a second selectable marker. Following sporulation, progeny spores which carry the defective mitochondrial LeuRS, identified by the presence of the cosegregating selectable marker, and the maintenance plasmid, identified by the presence of the second selectable marker, and which are rho+, can be isolated (e.g., by tetrad analysis). Strains constructed in this manner would be suitable for complementation assays using the helicobacter aminoacyl-tRNA synthetases.

For instance, a plasmid encoding a helicobacter leucyl-tRNA synthetase gene can be introduced into such a strain on a second plasmid having a third selectable marker. As indicated above, the maintenance plasmid can be selected against (e.g., where the selectable marker is URA3, selection on 5-fluoroorotic acid leads to loss of the maintenance plasmid), and complementation by the helicobacter gene can be monitored on a non-fermentable carbon source.

In another embodiment, a mitochondrial aminoacyl-tRNA synthetase gene disruption with a cosegregating selectable marker can be constructed in a diploid rho+ strain (see e.g., Edwards, H. and P. Schimmel, *Cell*, 51:643–649 (1987)). A plasmid encoding a helicobacter aminoacyl-tRNA synthetase gene is introduced on a plasmid having a second selectable marker. Sporulation of a resulting diploid yields two progeny spores carrying the yeast mitochondrial aminoacyl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the helicobacter gene on the introduced plasmid is indicated by growth on non-fermentable carbon sources of spores carrying the disrupted aminoacyl-tRNA synthetase gene.

In the case of a mitochondrial tester strain, the helicobacter aminoacyl-tRNA synthetase can be imported into mitochondria to achieve complementation of the mitochondrial defect. When it is necessary to achieve import or desirable to improve the efficiency of import of the aminoacyl-tRNA synthetase in the host cell, a gene fusion can be constructed using a sequence encoding a mitochondrial targeting sequence which functions in the host cell. For example, a mitochondrial targeting sequence can be introduced at the amino-terminal end of the helicobacter aminoacyl-tRNA synthetase. In one embodiment in yeast, the helicobacter aaRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus et al., *J. Biol. Chem.*, 263:13097 (1988)). Expression of the construct yields a fusion protein with an N-terminally located cytochrome oxidase IV targeting signal joined to the helicobacter aaRS protein.

If the construction methods described here are not successful initially, one or more natural or synthetic helicobacter or other (e.g., procaryotic, such as a bacterial, or eukaryotic, such as a mammalian or fungal) tRNA gene(s) can be introduced into the host cell to provide one or more cognate tRNAs for the helicobacter aaRS. The tRNA genes of a number of species have been cloned and sequenced (Steinberg, S., et al., "Compilation of tRNA sequences and sequences of tRNA genes", *Nucleic Acids Res.* 21:3011–3015 (1993)). A method for constructing a strain of *Streptomyces lividans* in which an essential tRNA gene has been inactivated in the chromosome, and the gene is instead maintained on a plasmid, has been described (Cohen, S. N., WO 94/08033 (1994)).

Use of Tester Strains

To assess the inhibitory effect of a substance on a tester strain, the cells are maintained under conditions suitable for complementation of the host cell defect, under which complementation of the host cell defect is dependent upon the test gene (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired. For example, a substance to be tested can be administered to tester cells maintained under assay conditions, and the viability or growth of the tester cells in the presence of the substance can be compared with that of tester cells maintained under the same conditions in the absence of the substance. If it is determined that the substance inhibits growth of the tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous aminoacyl-tRNA synthetase gene present in the tester strain (i.e., the "test gene"), can serve as control strains. These control strains comprise a "control gene" which is an aminoacyl-tRNA synthetase gene other than the heterologous aaRS gene present in the tester strain (i.e., an aaRS gene from a different species, such as a procaryotic or eukaryotic species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, a cell which is a cell of the same species as the host cell used to construct the tester strain, and which further comprises a control aaRS gene, is selected as a control. For example, the control gene can be a wild-type aaRS gene from the control strain species which encodes an aaRS specific for the same amino acid as the aaRS encoded by the test gene. Such a cell can be used when, for example, the substance or compound to be tested does not significantly affect growth of the control strain under the assay conditions. For example, where an *E. coli* host is used to construct a tester strain having an *H. pylori* aaRS gene, an *E. coli* strain having a wild-type *E. coli* control gene can be used as a control strain. As another example, if a yeast host cell having a defect in a mitochondrial aaRS gene is used to construct the tester strain, a yeast strain comprising the wild type mitochondrial gene can be used as a control strain.

In another embodiment, the control strain can be a strain distinct from the tester strain, which is constructed in a manner which generally parallels that of the tester strain comprising the test gene, such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene", which, as indicated above, is an aaRS gene other than the test gene (i.e., an aaRS gene from a different species, such as a heterologous procaryotic or eukaryotic species). Furthermore, the control gene, which can be cytoplasmic or mitochondrial, encodes an aaRS specific for the same amino acid as the test gene. Preferably, the control gene is selected from a species which is a host for the pathogen from which the test gene is derived, permitting the identification of specific inhibitors which selectively inhibit the pathogen aaRS (e.g., human control gene for an *H. pylori* test gene). Alternatively, because the eukaryotic aminoacyl-tRNA synthetases are generally more closely related to each other than to procaryotic aminoacyl-tRNA synthetases, a control gene from another eukaryote (e.g., a different mammalian species) can be used in lieu of one selected from the host species (e.g., a rat or mouse control gene for an *H. pylori* test gene).

For example, a strain isogenic with a tester strain, except for the substitution of a human control gene, can serve as a control strain. Such a control strain can be constructed using the same methods and the same host cell used to construct the tester strain, with the exception that a human control gene is introduced into the host cell in lieu of the heterologous helicobacter aaRS gene present in the tester.

Under the conditions of this assay, growth or viability of the control strain is dependent upon the control aaRS gene, which complements the host cell aaRS defect in the control strain. Specific inhibition by a substance can be determined by comparing the viability or growth of the tester strain and control strain in the presence of the substance.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an *E. coli* host is used to construct a tester strain comprising an *H. pylori* test gene, an *E. coli* strain comprising a wild-type *E. coli* aaRS gene can be used as a comparison control strain. In another embodiment, "parental-type" cells (e.g., parent host cells or a similar strain) are used as comparison controls. For example, the parent host cells of the tester strain can serve as a comparison control strain for the tester strain. Where the tester strain and the control strain have the same parent, a single strain can be used as the comparison control strain for both tester and control strains.

For example, a parent host cell from which the tester and control strains were both constructed (e.g., by inactivation and replacement of the wild type host aaRS gene) can be used as a comparison control strain. This comparison control strain contains a wild type version of the aaRS gene which is inactivated in the tester and control strains, and the viability or growth of this comparison control strain is dependent upon the wild type aaRS under the conditions of the assay. Specific inhibition of the heterologous helicobacter aaRS encoded by the test gene (or a step in the expression of the helicobacter gene) is indicated if, after administering the substance to the tester strain, growth of the tester strain is reduced as compared with an appropriate comparison control strain, and growth of the control strain is not reduced, or is relatively less reduced, as compared with its appropriate comparison control strain.

Testing for Antibiotic Resistance to tRNA Synthetase Inhibitors

Mutation of a drug target can reduce the effectiveness of antimicrobial or antibiotic agents, and can confer drug resistance. Thus, mutation of a target aminoacyl-tRNA synthetase, such as a H. pylori IleRS, MetRS, LeuRS, ValRS, LysRS or SerRS, could reduce the effectiveness of an inhibitor of aaRS activity. To test for mutations that confer resistance to an inhibitor (e.g., an inhibitor of aaRS activity, including such an inhibitor having antimicrobial activity) a variety of approaches can be used. Mutant helicobacter aaRS genes can be obtained, for example, by isolation of a mutant gene, or by preparing an individual mutant gene or an expression library of mutant helicobacter aaRS genes, such as a library of mutants of an H. pylori LysRS gene. The mutant gene or gene library can be introduced into suitable host cells for screening for resistance to a compound.

An isolated tRNA synthetase gene, such as an H. pylori aaRS gene, can be mutagenized by any suitable method including, but not limited to, cassette mutagenesis, PCR mutagenesis (e.g., the fidelity of PCR replication can be reduced to induce mutation by varying $Mg^{2+}$) concentration, increasing the number of amplification cycles, altering temperatures for annealing and elongation, to yield random mutants), or chemical mutagenesis (e.g., nitrosoguanidine, ethylmethane sulfonate (EMS), hydroxylamine) of the entire gene or a portion thereof. The mutagenesis products can be used to construct an expression library of mutant genes (e.g., by inserting the gene into an expression vector, or replacing a portion of an expression vector comprising the wild-type gene with mutant fragments) which is introduced into a host cell.

In one embodiment, if the inhibitor is known to inhibit the host cell (e.g., E. coli, yeast, Bacillus subtilis) aminoacyl-tRNA synthetase specific for the same amino acid, the mutant genes can be introduced into the wild-type host and the resulting cells can be exposed to drug to assess resistance.

In another embodiment, the procedures described above relating to tester strains are used in the method to identify mutants resistant to inhibitor. Introduction of the heterologous mutant aaRS gene(s) (i.e., mutant test gene(s)) into a host cell is carried out as described above for the production of tester strains. For example, the library can be introduced into a host cell having a defect in the endogenous gene encoding MetRS. The metG null strain of E. coli designated MN9261/pRMS615 is an example of the type of strain that can be constructed and used as a host for the introduction of mutant helicobacter aaRS gene(s) (in that case, MetRS genes; see Kim et al., Proc. Natl. Acad. Sci. USA 90:10046–10050 (1993), describing a strain which carries a null allele of metG, and a temperature sensitive maintenance plasmid, carring a wild type metG allele (encoding E. coli MetRS) and having a temperature sensitive replicon which causes loss of the maintenance plasmid at the nonpermissive temperature).

Active, drug-resistant mutants are then identified by a selection process in which cells containing mutant genes encoding active aaRS are identified, and the effect of an inhibitor upon aaRS activity is assessed. Cells are maintained under conditions suitable for expression of the mutated gene, and cells containing an active mutant aaRS (e.g., an active recombinant H. pylori aaRS) are identified by complementation of the host cell defect. Where complementation occurs, each resulting transformant is, in essence, a tester strain comprising a mutant test gene. Cells containing active mutant aaRS as determined by complementation of the host cell defect are then exposed to inhibitor, and the effect of inhibitor on cell growth or viability is assessed to determine whether the active mutant aaRS further confers resistance to inhibitor.

In the case of the metG null strain, complementation by the helicobacter gene is indicated by growth at the nonpermissive temperature at which the maintenance plasmid is lost. Cells which survive loss of the maintenance plasmid due to the presence of the complementing mutant gene are then challenged with inhibitor to assess resistance. Resistance can be assessed by comparison to a suitable control by methods analogous to those described above for determining inhibition and/or the specificity of inhibition of a substance in tester cells. For example, the relative effects of an inhibitor upon a tester strain comprising the mutant test gene and upon a tester strain differing only in that it contains the test gene lacking the mutation, can be assessed by comparing the viability or growth of cells which are dependent upon either the test gene or mutant test gene for growth under conditions suitable for complementation of the host cell defect. For instance, the effect of inhibitor on the protein encoded by the test gene lacking the mutation can be determined by comparing the growth of cells containing the test gene in the presence of drug to the growth of such cells in the absence of drug, and the effect of inhibitor on the protein encoded by a mutant test gene can be determined by comparing growth of cells containing the mutant test gene in the presence of drug to the growth of such cells in the absence of drug. A decrease in the inhibitory effect on growth of cells carrying the mutant test gene as compared to the inhibitory effect against cells carrying the test gene lacking the mutation is indicative of resistance.

Cells containing a complementing mutant test gene which further confers resistance to an inhibitor can be used to identify derivatives of the inhibitor with improved antimicrobial effect, which circumvent resistance. Such cells can also be used to identify additional inhibitors having inhibitory activity against the active mutant aaRS encoded by the mutant test gene.

In another embodiment, a naturally occurring mutant helicobacter aaRS gene which confers resistance to an inhibitor upon a helicobacter cell, can be isolated from the helicobacter organism using nucleic acids of the present invention as probes. The cloned gene can then be introduced into a host cell as described for the production of tester strains. Tester cells comprising the mutant test gene which confers resistance, and which complements the host defect, can be used as described herein to identify additional inhibitors having reduced susceptibility to the resistance mutation or derivatives of the inhibitor with improved inhibitory activity.

Vectors carrying mutant genes which confer resistance to inhibitor can be recovered and the insert analyzed to locate and identify the mutation by standard techniques, such as DNA sequence analysis, to yield additional information regarding the nature of mutations capable of conferring resistance to selected inhibitors. Mutant proteins can also be expressed and purified for further characterization by in vitro kinetic and binding assays.

Applications in Biochemistry

The helicobacter aminoacyl-tRNA synthetase or stable subdomains of the protein can be used in a method to separate the amino acid that the enzyme specifically recognizes from a mixture of the amino acid and other compounds such as other amino acids, or to specifically isolate L-amino acid from D-amino acid. The tRNA synthetase can be chemically attached to a solid support material packed in a column or other suitable container. Alternatively, a fusion protein, such as a GST-tRNA synthetase fusion or a His tag-tRNA synthetase fusion (having a histidine hexamer tail), can permit attachment to a suitable solid support which binds the GST portion or His tag portion of the fusion protein, respectively. For example, a mixture of lysine and other compounds can be loaded onto a column under conditions in which lysine binds to lysyl-tRNA synthetase, while other compounds present in the mixture flow through the column. In a later step, lysine can be released from lysyl-tRNA synthetase by changing the conditions in the column, such as washing with a solution of high ionic strength to elute L-lysine, for example.

In a similar manner, the aminoacyl-tRNA synthetase can be used in a method to isolate tRNA that is specifically recognized by the tRNA synthetase.

The helicobacter aminoacyl-tRNA synthetase can be used in the quantitative determination of an amino acid (e.g., lysine) by its conversion to the corresponding aminoacyl-hydroxamate (e.g., lysyl-hydroxamate). An example of an appropriate assay is illustrated by the following series of reactions.

(in the presence of excess pyrophosphatase and ATP at pH 7.5, where pyrophosphatase catalyzes the conversion of the product inorganic pyrophospate ($PP_i$) to inorganic orthophospate ($P_i$); ATP is adenosine triphospate; AMP is adenosine monophosphate)

The resulting colored complex can be quantitated by spectrophotometric measurements of absorbance at 540 nm, and compared with a standard curve made using known concentrations of lysine. This assay is based on the reactions described by Stulberg and Novelli, *Methods in Enzymology* 5:703–707 (1962).

The helicobacter aminoacyl-tRNA synthetases can also be used for the quantitative determination of ATP. In the presence of excess amino acid such as lysine, and in the presence of pyrophosphatase to convert the product $PP_i$ to $P_i$, the ATP is quantitatively converted to AMP and inorganic pyrophosphate by the lysyl-tRNA synthetase. For example,

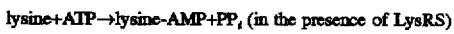

$P_i$ can be quantitated by reaction with molybdate, measuring the absorbance at 580 nm and comparing to a standard curve made using known quantities of orthophosphate.

EXEMPLIFICATION

The present invention will now be illustrated by the following Examples, which are not intended to be limiting in any way.

Example 1
PCR amplification of DNA fragments of aminoacyl-tRNA synthetase genes from *H. pylori* genomic DNA PCR was used to obtain the DNA fragments of aminoacyl-tRNA synthetase (aaRS) genes from *H. pylori* strain NCTC 11638 (National Collection of Type Cultures (NCTC), Central Public Health Laboratory, 61 Colindale Avenue, London, NW9 5HT, United Kingdom). The PCR primers were designed by aligning polypeptide sequences of corresponding aaRS from different species using the PILEUP program (Needleman and Wunsch, *J. Mol. Diol.*, 48:443–453 (1970)). Table 1 lists all the primers that have been used for amplification of the *H. pylori* aminoacyl-tRNA synthetases. A convenient EcoRI recognition sequence was introduced at the 5' end of several primers (extra sequence indicated by boldface in Table 1).

The PCR reactions were done in 50 μl volume with 10 mM Tris HCl (pH 8.3 at room temperature), 50 mM KCl, 2.5 mM $MgCl_2$, 200 μM of each dNTP (pH 7.0), 10 ng of *H. pylori* genomic DNA (NCTC 11638, provided by Douglas Berg; genomic DNA was prepared as described in Bukanov, N. O. and D. E. Berg, *Mol. Microbiol.* 11(3): 509–523 (1994)), 100 pmole each of the primers, and 2.5 units of AmpliTaq DNA polymerase (Perkin Elmer). The reactions were first incubated at 95° C. for 2 minutes, followed by 30 cycles of 95° C. (1 minute), 50° C. (1 minute), and 72° C. (2 minutes). The thermocycle reaction were extended for 8 minutes at 72° C.

The following combinations of primers were successfully used to amplify the partial sequences of *H. pylori* aaRS genes. For Ile, 3 combinations of primers produced PCR products: (a) primers KIYO-16 and KIYO-36 generated a DNA fragment of about 400 bp; (b) primers KIYO-37 and KIYO-20 generated a PCR product of 1.3 kb; and (c) primers KIYO-16, -17, and -20 generated a DNA fragment of about 1.5 kb. In the latter case, forward primers KIYO-16 and KIYO-17 were designed from the same region of the IleRS genes, but encode peptides having a different amino acid sequence bias. KIYO-16 and -17 were used simultaneously in a reaction in which KIYO-20 served as the reverse primer.

For Lys, the combination of KIYO-138, 139, and 140 produced a DNA fragment of about 250 bp. Primers KIYO-139 and KIYO-140 were designed from the same region of the LysRS genes, and were used simultaneously in a reaction in which they served as reverse primers and KIYO-138 served as the forward primer.

For Leu, primers KIYO-21 and KIYO-22 produced a DNA fragment of about 300 bp.

For Met, two primer mixtures yielded PCR products: (a) KIYO-12 and KIYO-15 produced a 550 bp DNA fragment; and (b) KIYO-12, -13, -14, and -15 produced a 550 bp fragment, with KIYO-12 and -13 serving as forward primers and KIYO-14 and -15 served as reverse primers.

For Ser, the combination of SerF266, SerR364, and SerR407 produced a DNA fragment of about 500 bp. Reverse primers SerR364 and SerR407 were designed from different regions of SerRS. Use of reverse primer SerR407 and forward primer SerF266 yielded the PCR product, as determined by matching the size of the resulting PCR fragment with the expected sizes.

For Val, primers Val2A and Val6 generated a DNA fragment of 1.2 kb.

In each case, the sizes of the amplified DNA fragments were in good agreement with the predicted sizes of the fragments.

TABLE 1

Degenerate PCR Primers for Amplification of *H. pylori* Aminoacyl-tRNA synthetases

| aaRS | Primer | SEQ ID NO: | Primer Sequence (5' → 3') |
|---|---|---|---|
| Met | KIYO-12 | 13 | GCG AAT TCT WYC TIA CIG GIA CIG AYG ARC AYG G |
|  | KIYO-13 | 14 | GCG AAT TCT TYA TIT GYG GIA CIG AYG ARY AYG G |
|  | KIYO-14 | 15 | GCG AAT TCR TAR TTI ATI AGI GCR TCR AWC CAI ACR TA |
|  | KIYO-15 | 16 | GCG AAT TCR TAI CCR ATI GKI GCR TCI ARC CAI ACR TA |
| Ile | KIYO-16 | 17 | GCG AAT TCG GIT GGG AYA CIC AYG GIS TIC C |
|  | KIYO-17 | 18 | GCG AAT TCG GIT GGG AYT GYC AYG GIC TIC C |
|  | KIYO-18 | 19 | GCG AAT TCG ICA RCG ITA YTG GGG IRT ICC IAT |
|  | KIYO-19 | 20 | GCG AAT TCG IAA YCG ITW YTG GGG IAC ICC IMT |
|  | KIYO-20 | 21 | GCG AAT TCR AAC CAI CCI CGI GTY TGR TCI WWI CCY TC |
|  | KIYO-36 | 22 | GGI ARI GTC CAI GGI GTI GTI GTC CA |
|  | KIYO-37 | 23 | TWY ATG GAR TCI ACI TGG TGG GYI TTI AAR CA |
| Val | Val2A | 24 | GAY CAY GCI GGI ATH GCI ACN CA |
|  | Val4 | 25 | RTC RTG IGC IGG IGT DAT YTT |
|  | Val6 | 26 | RAA CCA IGT RTC IAR IAC RTC |
| Leu | KIYO-21 | 27 | GCG AAT TCC IAT IGG ITG GGA YGC ITT YGG ICT ICC |
|  | KIYO-22 | 28 | GCG AAT TCA CYT GYT CRT TIG CIA GIA CIG T |
|  | KIYO-34 | 29 | CCI MTI GGI TWY CAY TGY ACI GGI MTI CC |
|  | KIYO-35 | 30 | GCR TCR TAR TAI GGR TTI GCR TCI GTI GTI ACR AA |
| Lys | KIYO-138 | 31 | TTY MTI GAR GTI GAR ACI CCI ATG ATG |
|  | KIYO-139 | 32 | TAR AAY TCI ATI GTI GTR AAY TCI GGR TTR TG |
|  | KIYO-140 | 33 | TAC MAY TCI AKC ATI GTR AAY TCI GGR TTR TG |
| Ser | KIYO-141 | 34 | AAR AAR TAY GAY CTI GAR GCI TGG TTY CC |
|  | KIYO-142 | 35 | AAR ACI TAY GAY CTI GAR GTI TGG ATH CC |
|  | KIYO-143 | 36 | CCY TTY TCI GTY TGR TAR TTY TC |
|  | KIYO-144 | 37 | CCR TCY TCI GTY TGR TAR TTY TC |
|  | SerF266 | 38 | SCI TGT TTT MGI TCW GAA GCI GG |
|  | SerF356 | 39 | TAT MGI GAA ATT TCW TGT TCW AAT |
|  | SerR364 | 40 | TAA WGA ACA WGA AAT TTC ICK ATA |
|  | SerR407 | 41 | CCA TCH KST TGT TGA TRA TTT TC |

Example 2

Cloning and characterization of the PCR products

The PCR products were isolated on a 1.2% agarose gel and purified by GeneClean (Bio 101). One third to one fifth of the purified DNA fragments were ligated to 50 ng of pT7Blue (R) T-vector (Novagen). The ligated plasmids were transformed into *E. coli* DH5α cells (competent cells purchased from Gibco/BRL), and the transformants were plated on LB-agar plates containing 100 µg/ml ampicillin, 30 µg/ml X-gal, and 0.1 mM IPTG. The white colonies were rapidly screened by using direct colony PCR with T7 and U19 primers that hybridize to the vector sequences flanking the cloning site (Novagen). The plasmids containing the inserts with expected sizes were isolated, and the sequences of the inserts were determined by dideoxy-sequenase sequencing (USB) with the T7 and U19 primers. By querying the sequences against the Non-redundant Protein Data Bases of the BLAST Network Service at the National Center for Biotechnology Information (NCBI), the following clones containing the partial sequences of the corresponding aaRS genes were identified: 2B-3, Ile; 9B-5, Lys; 10B-2, Leu; 13B-3, Met; 19-3, Ser; Val-4, Val.

Example 3

Screening of an ordered cosmid *H. Pylori* genomic library

Materials

The solutions shown in Table 2 below were used during screening of the *H. pylori* genomic library.

TABLE 2

Screening Solutions

| Solution | Composition |
|---|---|
| Solution I | 50 mM Tris-Cl, pH 8.0/50 mM EDTA, pH 8.0/ 25% sucrose/1.5 mg/ml lysozyme |
| Solution II | 0.5 N NaOH/0.2% Triton X-100 |
| Solution III | 0.5 N NaOH |
| Solution IV | 1 M Tris-Cl, pH 7.5 |
| Solution V | 0.15 M NaCl/0.1 M Tris-Cl, pH 7.5 |

Library Screening

The cloned PCR fragments of *H. pylori* aaRS genes were used as the probes to screen an ordered cosmid genomic library of *H. pylori* (strain NCTC 11638) (Bukanov, N. O. and D. E. Berg, "Ordered cosmid library and high-resolution physical-genetic map of Helicobacter pylori strain NCTC11638", *Mol. Microbiol.* 11(3): 509–523 (1994)). The library was provided by Douglas Berg in Washington University at St. Louis. It is composed of 68 independent clones and covers 95% of the genomic sequence.

One microliter of bacterial culture of each of the 68 library clones was spotted directly onto a piece of Gene-Screen hybridization nylon membrane (Dupont/NEN), which was placed on top of a LB-agar plate containing 50 µg/ml of kanamycin. The plate was then incubated at 37° C. for 16 hours to allow the bacterial cells to grow. The GeneScreen membrane with the bacterial cells was chilled at 4° C. for 1 hour. To lyse the cells and denature the DNA in situ, the prechilled nylon membrane was treated with the solutions listed in Table 2 as follows. First, the membrane was placed right-side-up on a piece of 3MM paper (Whatman), which was saturated with solution I and incubated for 1 minute at room temperature. The membrane was then transferred to a piece of fresh, dry 3MM paper and allowed to stand for 1 minute. These steps were repeated a total of four times for solution I. The same procedure was used to treat the membrane with each of solutions II through V in turn. After treatment with solution V, the membrane was air dried for 30 minutes, baked in a vacuum oven at 80° C. for 2 hours, and washed three times in 300 ml prewashing buffer (3X SSC /0.1% SDS). The first two washes were for 2 hours at 65° C. and the last one was overnight at 65° C. The prewashed filter was then incubated in 10 ml of Southern prehybridization solution (6X SSC / 0.5% SDS / 5X Denhardt's solution / 100 μg/ml sheared and denatured calf thymus DNA) at 65° C. for at least 2 hours before being probed with the partial DNA fragments of the *H. pylori* aaRS genes generated by PCR.

The polymerase chain reaction was used to generate probes for hybridization with the *H. pylori* genomic library. The templates for the PCR reactions were the pT7Blue (R) T-vector clones designated 2B-3, 9B-5, 10B-2, 13B-3, 19-3, Val-4. A typical reaction was carried out in 50 μl containing 10 mM Tris HCl (pH 8.3 at room temperature), 50 mM KCl, 2.5 mM $MgCl_2$, 20 pmole each of T7 and U19 primers, ~10 ng template, 200 μM each of dATP, dGTP, dTTP, 3 μM dCTP, 50 μCi [$\alpha$-$^{32}$P] dCTP (3000 Ci/mmole, Dupont/NEN), and 2.5 units of AmpliTaq DNA polymerase (Perkin Elmer). For the Ile probe, 100 μM of cold dCTP was used. For the Lys and Leu probes, 35 μCi of [$\alpha$-$^{32}$P]dCTP was used. The reactions were first incubated at 95° C. for 2 minutes followed by 30 cycles of 95° C. (30 seconds), 55° C. (30 seconds), 72° C. (2 minutes), and extended for an additional 8 minutes at 72° C. after the thermocycles. Under these conditions, probes with a specific activity calculated to be about $1 \times 10^9$ cpm/μg DNA were obtained.

The $^{32}$P-labelled probes were then purified by Sephadex G50 spin columns (Boehringer Mannheim), denatured by boiling for 5 minutes, and added to the hybridization nylon membranes in 10 ml of hybridization solution (6X SSC / 10 mM EDTA / 0.5% SDS / 5X Denhardt's solution / 100 μg/ml sheared and denatured calf thymus DNA). The hybridizations were at 65° C. for 16–24 hours. The membranes were then typically washed three times: the first two washes were with 500 ml of 2X SSC, 0.5% SDS solution at room temperature for 15 minutes, and the third wash was with 500 ml of 0.2X SSC / 0.5% SDS at 65° C. for one hour. Hybridizations were then analyzed by autoradiography.

The PCR fragment amplified from Clone 2B-3, which contains a 1.5 kb fragment of IleRS gene, hybridized to the cosmid library clone 51. (Cosmid library clone numbers (51, 67, 54, 55, 29–31, 48, 49, and 40–42) correspond to the clones of the same number in FIG. 2 of Bukanov, N. O. and D. E. Berg, *Mol. Microbiol.* 11(3): 509–523 (1994).) The PCR fragment amplified from Clone 9B-5, which contains a 250 bp fragment of LysRS gene, hybridized to the cosmid library clone 67. The PCR fragment amplified from Clone 10B-2, which contains a 300 bp fragment of LeuRS gene, hybridized to cosmid library clones 54 and 55. The PCR fragment amplified from Clone 13B-3, which contains a 550 bp fragment of MetRS gene, hybridized to cosmid library clones 29, 30, 31. The PCR fragment amplified from Clone 19-3, which contains a 500 bp fragment of SerRS gene, hybridized to the cosmid library clones 48 and 49. The PCR fragment amplified from Clone Val-4, which contains a 1.2 kb fragment of ValRS gene, hybridized to the cosmid library clones 40, 41, and 42.

Example 4
Sequencing of *H. pylori* aaRS genes

The partial sequences of the PCR fragments were used to design the initial internal sequencing primers. Promega fmol DNA Sequencing System was used to sequence the *H. pylori* aaRS genes, using the cosmid DNAs of the positive clones as the templates. The thermal cycle sequencing were carried out according to the Technical Manual of the fmol DNA Sequencing System (Promega) with 5'-$^{33}$P labelled primers. The cosmid clones chosen for sequencing were: Ile, clone 51; Lys, clone 67; Leu, clone 55; Met, clone 30; Ser, clone 49; Val, clone 41.

The DNA sequence generated with each primer was processed with the DNASTAR program (DNASTAR, Inc.), and its homology to the existing aaRS genes in the database was traced using the BLAST program (Basic Local Alignment Search Tool; Gish et al., *Nature Genetics* 3:266–272 (1993); Altschul et al., *J. Mol. Biol.* 215:403–410 (1990)). The individual sequences were assembled using the DNA Sequence Management Program with the DNASTAR package to generate full-length genes. The initiation codon of each gene was identified by comparison with known corresponding aaRS sequences in the data bank using the Multiple Sequence Alignment program from the DNASTAR package, by the existence of a putative ribosomal binding site upstream of the initiation codon, and in most cases, by the fact that they are the first methionine codons in the corresponding open reading frames.

The nucleotide sequence determined for the *H. pylori* isoleucyl-tRNA synthetase gene is shown in SEQ ID NO:1. The open reading frame (ORF) is 2760 base pairs and encodes a polypeptide of 920 amino acids (SEQ ID NO:2), with translation starting at the GTG at position 149 in SEQ ID NO:1. GTG initiation codons (GUG in the mRNA) have been observed in *H. pylori* (see Labigne et al., *J. Bacteriol.*, 173: 1920–1931 (1991), describing the UreD gene), as well as in other organisms. Where a codon other than AUG has been observed, invariably, the amino acid used for initiation has been determined to be methionine (Varshney, U. and U. L. RajBhandary, *Proc. Natl. Acad. Sci. USA*, 87:1586–1590 (1990)). Accordingly, SEQ ID NO:1 shows a methionine at the N-terminus of the encoded protein. The deduced amino acid sequence of IleRS contains a $^{65}$HLGH$^{68}$ motif, which resembles the HIGH sequence, and a $^{610}$KMSKS$^{614}$ motif. These two sequence motifs are characteristic of all class I aaRSs. The *H. pylori* IleRS amino acid sequence was compared with the IleRS sequences available in the data bank by using the Multiple Sequence Alignment program from the DNASTAR package. Percent similarity and percent divergence among these sequences were determined using the Clustal method with PAM250 residue weight table. The percent similarity between the predicted 920-amino acid sequence of *H. pylori* IleRS and proteins identified as IleRSs from *C. jejuni* and *Staphylococcus aureus* was found to be 65.5% and 54.0%, respectively. Other sequences were even less related.

The nucleotide sequence determined for the *H. pylori* methionyl-tRNA synthetase gene is shown in SEQ ID NO:3. The ORF is 1944 base pairs, encoding a polypeptide of 648 amino acids (SEQ ID NO:4), with translation starting from the ATG at position 102 in SEQ ID NO:3. The deduced MetRS sequence contains class-defining motifs at position 18 ($^{18}$HIGH$^{21}$) and at position 301 ($^{301}$KMSKS$^{305}$) SEQ ID NO:3. The *H. pylori* MetRS sequence was compared with the MetRS sequences available in the data bank by using the Multiple Sequence Alignment program from the DNASTAR package. Percent similarity and percent divergence among these sequences were determined using the Clustal method with PAM250 residue weight table. The percent similarity between the predicted 648-amino acid sequence of *H. pylori* MetRS and proteins identified as MetRSs from *B. stearothermophilus* and *T. thermophilus* was found to be 36.2% and 34.6%, respectively. Other sequences were even less related.

The nucleotide sequence determined for the *H. pylori* leucyl-tRNA synthetase gene is shown in SEQ ID NO:5. The ORF is 2418 base pairs, encoding a polypeptide of 806 amino acids (SEQ ID NO:6) with translation starting from the ATG at position 153 in SEQ ID NO:5. The putative leucyl-tRNA synthetase also contains class I motifs ($^{45}$HMGH$^{48}$ and $^{572}$KMSKS$^{576}$, SEQ ID NO:5. The *H. pylori* LeuRS sequence was compared with the LeuRS sequences available in the data bank by using the Multiple Sequence Alignment program from the DNASTAR package. Percent similarity and percent divergence among these sequences were determined using the Clustal method with PAM250 residue weight table. The percent similarity between the predicted 806-amino acid sequence of *H. pylori* LeuRS and proteins identified as LeuRSs from *E. coli* and *Bacillus subtilis* was found to be 39.3% and 34.2%, respectively. Other sequences were even less related.

The nucleotide sequence determined for the *H. pylori* valyl-tRNA synthetase gene is shown in SEQ ID NO:7. The ORF is 2616 base pairs, encoding a polypeptide of 872 amino acids (SEQ ID NO:8), with translation starting from the ATG at position 219 in SEQ ID NO:7. In the deduced protein sequence, the class-defining HIGH and KMSKS motifs are located between positions 56–59 and 531–535, respectively SEQ ID NO:8. The *H. pylori* ValRS sequence was compared with the ValRS sequences available in the data bank by using the multiple sequence alignment program from the DNASTAR package. Percent similarity and percent divergence among these sequences were determined using the Clustal method with PAM250 residue weight table. The percent similarity between the predicted 872-amino acid sequence of *H. pylori* ValRS and proteins identified as ValRSs from *B. stearothermophilus* and *E. coli* was found to be 36.3% and 33.4%, respectively. Other sequences were even less related.

The nucleotide sequence determined for the *H. pylori* lysyl-tRNA synthetase gene is shown in SEQ ID NO:9. The ORF is 1503 base pairs, encoding a polypeptide of 501 amino acids (SEQ ID NO:10), with translation starting from the ATG at position 121 in SEQ ID NO:9. The three class-defining sequence motifs, which are highly conserved among the class II aminoacyl-tRNA synthetases, are located between positions 191–200, 251–268, and 460–473, respectively in the deduced amino acid sequence of *H. pylori* LysRS. The *H. pylori* LysRS sequence was compared with the LysRS sequences available in the data bank by using the multiple sequence alignment program from the DNASTAR package. Percent similarity and percent divergence among these sequences were determined using the Clustal method with PAM250 residue weight table. The percent similarity between the predicted 501-amino acid sequence of *H. pylori* LysRS and proteins identified as *C. jejuni* LysRS, the *E. coli* lysS gene product, and the *E. coli* lysU gene product was found to be 57.3%, 47.6%, and 46.4% respectively. Other sequences were even less related.

The nucleotide sequence determined for the *H. pylori* seryl-tRNA synthetase gene is shown in SEQ ID NO:11. The ORF is 1245 base pairs, encoding a polypeptide of 415 amino acids (SEQ ID NO:12), with translation starting from the ATG at position 80 in SEQ ID NO:11. As in the *H. pylori* LysRS, three class II aaRS sequence motifs can also be identified in the deduced amino acid sequence of *H. pylori* SerRS. They are located between positions 190–199, 261–285, and 382–394, respectively . The *H. pylori* SerRS sequence was compared with the SerRS sequences available in the data bank by using the Multiple Sequence Alignment program from the DNASTAR package. Percent similarity and percent divergence among these sequences were determined using the Clustal method with PAM250 residue weight table. The percent similarity between the predicted 415-amino acid sequence of *H. pylori* SerRS and proteins identified as SerRSs from *E. coli* and *Coxiella burnetii* was found to be 44.5% and 42.1%, respectively. Other sequences were even less related.

Example 5

Expression of GST-*H. pylori* Ile and Met tRNA synthetase fusion proteins

The DNA fragments comprising the ORFs of Ile and Met tRNA synthetases were recovered by PCR amplification using the following PCR primers:

| | |
|---|---|
| Ile 5' primer (SEQ ID NO: 42): | 5'-CGTGGATCCGTGAAAGAATACAAAGACAC-3' |
| Ile 3' primer (SEQ ID NO: 43): | 5'-CCCAGTCGACTTATCATCGCTCTTTTAAAACC-3' |
| Met 5' primer (SEQ ID NO: 44): | 5'-CGTGGATCCATGCAAAAATCACTGATCAC-3' |
| Met 3' primer (SEQ ID NO: 45): | 5'-CCCAGTCGACTTAGCTGATCAAACTTCCTGC-3' |

PCR reactions were carried out in 50 µl with 10 mM Tris HCl (pH 8.3 at room temperature), 50 mM KCl, 1 µl of of cosmid DNA (clone 51 for IleRS and clone 30 for MetRS), 20 pmole each of the 5' and 3' primers, 0.2 mM each of dNTPs, 1.5 mM MgCl$_2$, and 5 units of AmpliTaq DNA polymerase (Perkin-Elmer). The reactions were first denatured for 2 minutes at 95° C., followed by 30 cycles of 95° C. (30 seconds), 55° C. (30 seconds), and 72° C. (2 minutes). The thermal cycles were extended at 72° C. for 8 minutes.

The amplified DNA fragments were purified by using Gene Clean method (Bio 101), and then digested with BamHI/SalI restriction endonucleases (New England Biolabs, Inc.) followed by gel purification. The purified DNA fragments were then cloned into the BamHI/SalI sites of pGEX-4T-2 *E. coli* expression vector (Pharmacia), yielding the plasmids pGEXHPIRS-1 (for GST-IleRS fusion) and pGEXHPMRS-1 (for GST-MetRS fusion), respectively.

The *H. pylori* IleRS and MetRS expression constructs were used to transform *E. coli* DH5α cells. To test the expression of the recombinant GST (glutathione-S-transferase) fusion proteins, the transformed cells were grown 5 hours at 37° C. in 3 ml of LB broth with 50 µg/ml of ampicillin until the A600 of the bacterial cultures reached 0.6 to 1. Protein expression was induced by the addition of IPTG to 1 mM. After 2.5 hours induction of protein expression at 37° C., the bacterial cells were recovered by centrifugation, and lysed in 1X phosphate-buffer-saline (1X PBS: 140 mM NaCl, 2.7 mM KCl, 10 mM Na$_2$HPO$_4$, 1.8 mM KH$_2$PO$_4$, pH7.3) by sonication. The soluble proteins of the crude cell extracts were obtained by centrifugation of the cell lysates and fractionation by electrophoresis on a 10% SDS-polyacrylamide gel. Protein was visualized by staining with Coomassie Blue.

In the case of IleRS, a protein with apparent molecular weight of about 130 kDa was expressed without induction, and a higher level of expression was achieved upon the IPTG induction. For MetRS, a protein of about 97 kDa was expressed to detectable levels upon induction with IPTG. The MetRS protein was not visible in the absence of IPTG induction. Both of the recombinant proteins can be purified using glutathione-agarose affinity chromatography as described below.

Example 6
Purification and Aminoacylation Activities of the H. pylori GST-Ile and GST-Met tRNA Synthetases 20 ml overnight LB cultures (with 50 µg/ml of ampicilline) of E. coli harboring the pGEXHPIRS-1 or pGEXHPMRS-1 plasmid were used to inoculate fresh 2 liter cultures of LB (containing 50 µg/ml of ampicillin). The cells were grown at 37° C. for 3.5 hours to reach OD600 to 0.9–1.0 before IPTG was added to final concentration of 1 mM to induce the expression of recombinant proteins. After 3 hours of IPTG induction of expression, the bacterial cells were pelleted by centrifugation in Beckman JA10 rotor for 20 minutes at 6000 rpm and stored at −80° C. until protein purification.

To purify the proteins, the cells were resuspended in 30 ml of 1X PBS with 5 mM DTT and 2 mg/ml lysozyme. Non-ionic detergent NP-40 was added to the cell suspension to final concentration of 0.1% prior to the cell lysis by French Press. The cell lysates were centrifuged at 12,000 g for 10 min at 4° C. and the supernatants were recovered and loaded onto 15 ml Glutathione-agarose (SIGMA Chemical Co., St. Louis, Mo.) affinity columns equilibrated with 1X PBS/ 5 mM DTT at 4° C.

After the samples were loaded, each column was washed with 150 ml of 1X PBS with 5 mM DTT at 4° C. The GST-aaRS fusion protein bound specifically to the glutathione on the column was eluted with 30 ml of 10 mM glutathione, 50 mM Tris-HCl (pH7.9) solution, at 25° C. The eluted fusion protein was concentrated by using Centricon (Amicon) to final volume of 2 ml. The purified proteins were analyzed on a 10% SDS-polyacrylamide gel. The proteins were stored at −80° C. with 50% glycerol and 5 mM DTT.

The purified GST fusions of H. pylori isoleucyl- and methionyl-tRNA synthetase were tested for their corresponding charging activities. Charging (aminoacylation) assays were based on the procedure of Shepard et al. (Proc. Natl. Acad. Sci. USA, 89: 9964–68 (1992)). Aminoacylation reactions with IleRS were carried out in 50 mM HEPES, pH7.5, 10 mM 2-mercaptoethanol, 4 mM ATP, 10 mM $MgCl_2$, 20 µM [$^3H$]-isoleucine (80 µCi/ml), 180 µM crude E. coli total tRNA (SIGMA), and 1 µl of the purified GST-H. pylori IleRS protein. Aminoacylation reactions with MetRS were carried out in 20 mM HEPES, pH 7.5, 0.1 mM EDTA, 150 mM $NH_4Cl$, 100 µg/ml BSA, 2 mM ATP, 4 µM tRNA$^{Met}$ (Boehringer-Mannheim), 4 mM $MgCl_2$, and 20 µM [$^{35}S$]-methionine (40 uCi/ml) and 1 µl of the purified GST-H. pylori MetRS protein.

Reactions were incubated at 25° C. For each time point, an aliquot of the reaction mixture was removed and spotted onto Whatman 3MM paper filter disks. The filter disks were immediately placed in cold 5% trichloroacetic acid (TCA). After 3 washes in 5% TCA (20 minutes each), the filter disks were washed once with 95% ethanol for 5 minutes, briefly washed once with ether, dried under a heat lamp, and subjected to scintillation counting.

Figure 2:
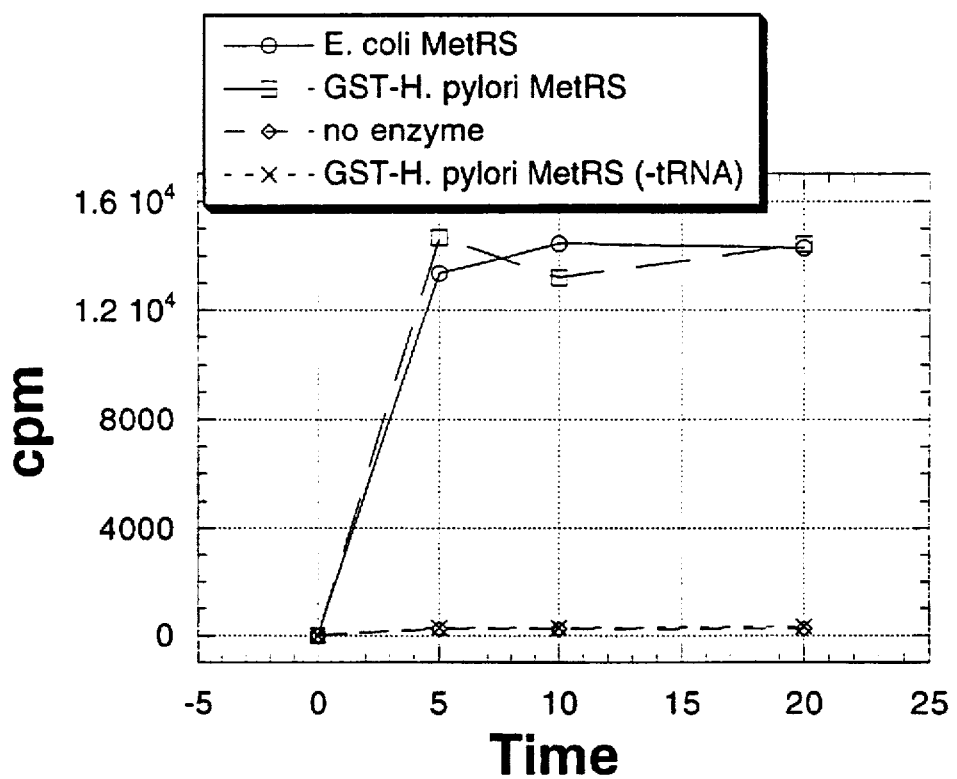
FIG. 2 is a graph illustrating the aminoacylation activity (cpm, counts per minute of [³H]methionyl-tRNA) over time (minutes) of the GST-*H. pylori* Met tRNA synthetase as compared with that of purified *E. coli* Met tRNA synthetase, using *E. coli* tRNA$^{Met}$ as a substrate (Example 6). O, *E. coli* MetRS; □, GST-*H. pylori* Met tRNA synthetase; ◊, no enzyme; X, GST-*H. pylori*-Ile tRNA synthetase minus tRNA.

As positive controls, purified E. coli IleRS and MetRS were assayed in the same way as the purified recombinant proteins. E. coli IleRS was purified as previously described (Shepard et al., Proc. Natl. Acad. Sci. USA, 89:9964–68 (1992)). About 10 ng of the purified enzyme was used in the assay. E. coli MetRS was also purified using a published protocol (Burbaum, J. J. and P. Schimmel, Biochemistry, 30: 319–324 (1991)). About 2 µg of the purified MetRS was used in the assay. Reactions without aaRS or without tRNAs were carried out under the same conditions, as negative controls. The results are depicted in FIGS. 1 and 2.

Example 7
Expression of H. pylori leucyl-, valyl-, seryl-, and lysyl-tRNA synthetases H. pylori leucyl-, valyl-, seryl-, and lysyl-tRNA synthetases were also expressed as GST (glutathione-S-transferase) fusion proteins. For each synthetase, a DNA fragment comprising the open reading frame was recovered by PCR amplification using the following pairs of PCR primers for each synthetase:

| | |
|---|---|
| Leu 5' primer (SEQ ID NO:46): | 5'-GCGCGGATCCATGGATTTTATCAATATAGAAA-3' |
| Leu 3' primer (SEQ ID NO:47): | 5'-ACGCGTCGACTTATGCGATAACAAAATTAACG-3' |
| Val 5' primer (SEQ ID NO:48): | 5'-GCGCGGATCCATGAAACAAGAACCCACCACCT-3' |
| Val 3' primer (SEQ ID NO:49): | 5'-ACGCGTCGACTTATGGTTGTTTTAACAAATC-3' |
| Ser 5' primer (SEQ ID NO:50): | 5'-GCGCGGATCCATGATTGATAGAAAACTTTTAT-3' |
| Ser 3' primer (SEQ ID NO:51): | 5'-ACGCGTCGACTTAAAGGTATTTTTCTAACGC-3' |
| Lys 5' primer (SEQ ID NO:52): | 5'-GCGCGGATCCATGTTTTCTAACCAATACATC-3' |
| Lys 3' primer (SEQ ID NO:53): | 5'-ACGCGTCGACTTATTCTCCACTCTCTCCACA-3' |

For the Ser primers, the reaction was performed essentially as described above for the Ile and Met GST-fusion proteins (see Example 5) using cosmid DNA clone 49 as template.

For Lys, Leu and Val primers, individual reactions were carried out in a 50 µl volume with 1X Vent DNA polymerase buffer (New England Biolabs), 20 pmole of each of the 5' and 3' primers, 0.1 mM each of dNTPs, and 2 units of Vent DNA polymerase (New England Biolabs). One µl (~5–20 ng) of cosmid DNA was used as template in each reaction (templates: Lys, clone 67; Leu, clone 55; Val, clone 41). The reactions were first denatured for 2 minutes at 95° C., followed by 30 cycles of 95° C. (30 seconds), 55° C. (30 seconds), and 72° C. (2 minutes). The thermal cycles were extended at 72° C. for 8 minutes.

The amplified DNA fragments were purified by using Gene Clean (Bio 101), and then digested with BamHI and SalI restriction endonucleases (New England Biolabs, Inc.) followed by gel purification. The purified DNA fragments were then cloned into expression vector pGEX-4T-2 (Pharmacia) which had been linearized with BamHI and SalI.

The resulting GST fusion expression constructs for leucyl-, valyl-, seryl-, and lysyl-tRNA synthetases were designated pGEXHPLEU-3, pGEXHPVAL-1, pGEXHPSER-2, and pGEXHPLYS-1, respectively. Transformants of E. coli DH5-α and E. coli JM109 were obtained for each construct.

The Lys 3' primer (SEQ ID NO:53) used for amplification of the H. pylori LysRS gene contained a 2 nucleotide insertion (CT, indicated in bold above). As a result of this insertion, the GST-LysRS fusion protein encoded by pGEXHPLYS-1 consists of an N-terminal GST portion fused to amino acids 1-498 of LysRS, and an extra C-terminal 12 amino acids fused to Glu$^{498}$ (i.e., -Arg-Val-Glu-Asn-Lys-Ser-Thr-Arg-Ala-Ala-Ala-Ser) (SEQ ID NO:67), which were introduced by frameshift and readthrough into the vector (pGEX-4T-2; amino acids in bold are encoded by the vector).

GST-SerRS and GST-LysRS fusion proteins were expressed in JM109 cells and purified essentially as described for the GST-IleRS and GST-MetRS fusion proteins (see Example 6). GST-LeuRS and GST-ValRS fusion proteins were also expressed to a high level upon IPTG induction.

Example 8
Aminoacylation Activities of the *H. pylori* GST-Ser and GST-Lys tRNA Synthetases Aminoacylation reactions with SerRS or LysRS were carried out in 50 mM HEPES, pH 7.5, 8 mM KF, 16 mM 2-mercaptoethanol, 4.4 mM ATP, 10 mM MgCl$_2$, 18 µM Ser (39 µCi [$^3$H]-serine/ml) or 20 µM Lys (220 µCi [$^3$H]-lysine/ml), and 90 µM *E. coli* total tRNA (Boehringer-Mannheim). About 0.3 µg of purified GST-SerRS or 0.3 µg of purified GST-LysRS was added to the corresponding charging reaction.

Figure 3:
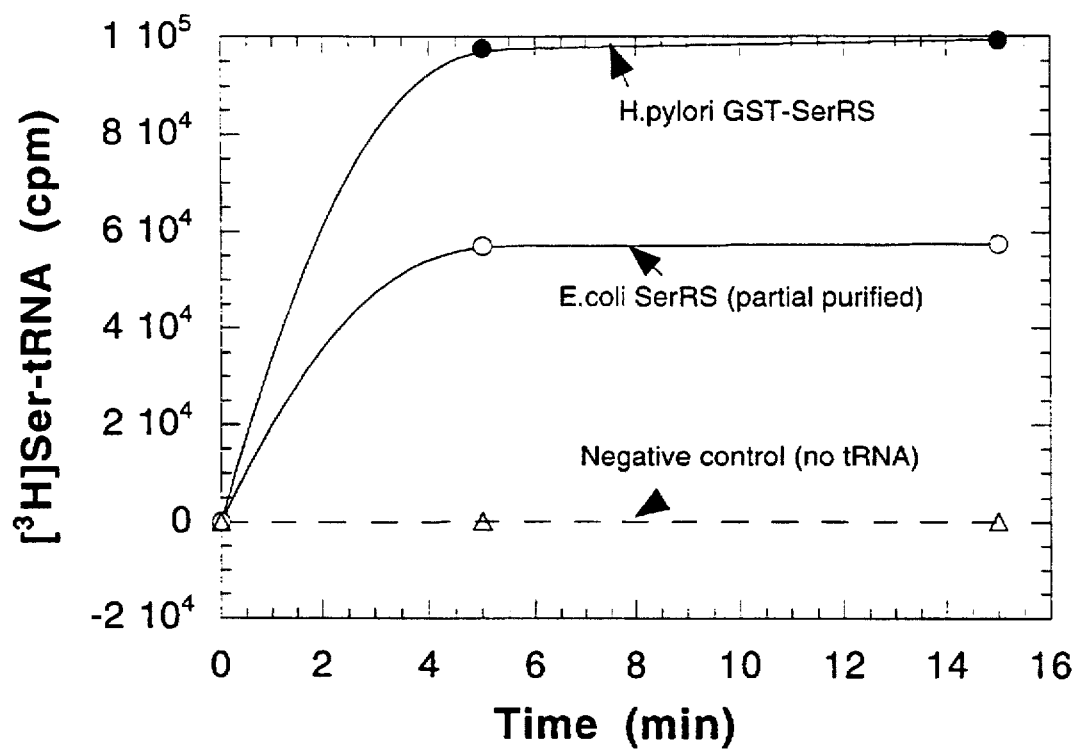
FIG. 3 is a graph illustrating the aminoacylation activity (cpm, counts per minute of [³H]seryl-tRNA) over time of the GST-*H. pylori* Ser tRNA synthetase as compared with that of partially purified *E. coli* Ser tRNA synthetase, using 90 µM *E. coli* total tRNA (Boehringer-Mannheim) as a substrate (Example 8). O, *E. coli* SerRS; ●, GST-*H. pylori* Ser tRNA synthetase; ▲, GST-*H. pylori*-Ser tRNA synthetase minus tRNA.
Figure 4:
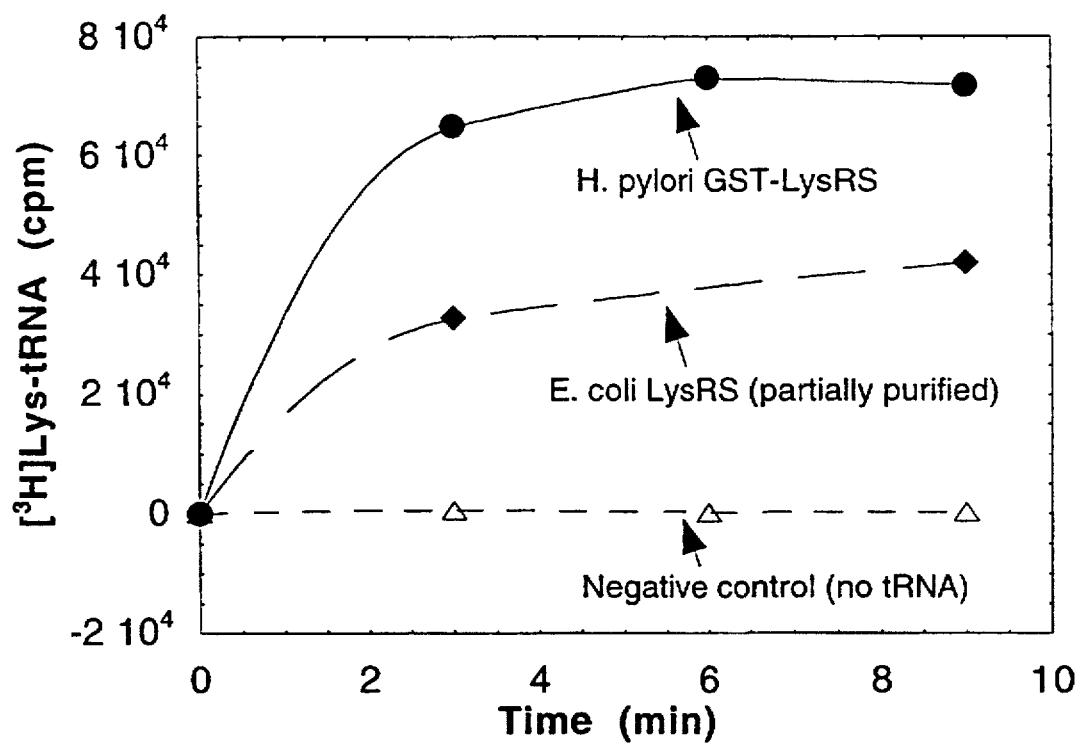
FIG. 4 is a graph illustrating the aminoacylation activity (cpm, counts per minute of [³H]lysyl-tRNA) over time of the GST-*H. pylori* Lys tRNA synthetase as compared with that of partially purified *E. coli* Lys tRNA synthetase, using 90 µM *E. coli* total tRNA (Boehringer-Mannheim) as a substrate (Example 8). ♦, *E. coli* LysRS; ●, GST-*H. pylori* Lys tRNA synthetase; ▲, GST-*H. pylori*-Lys tRNA synthetase minus tRNA.
Figure 5:
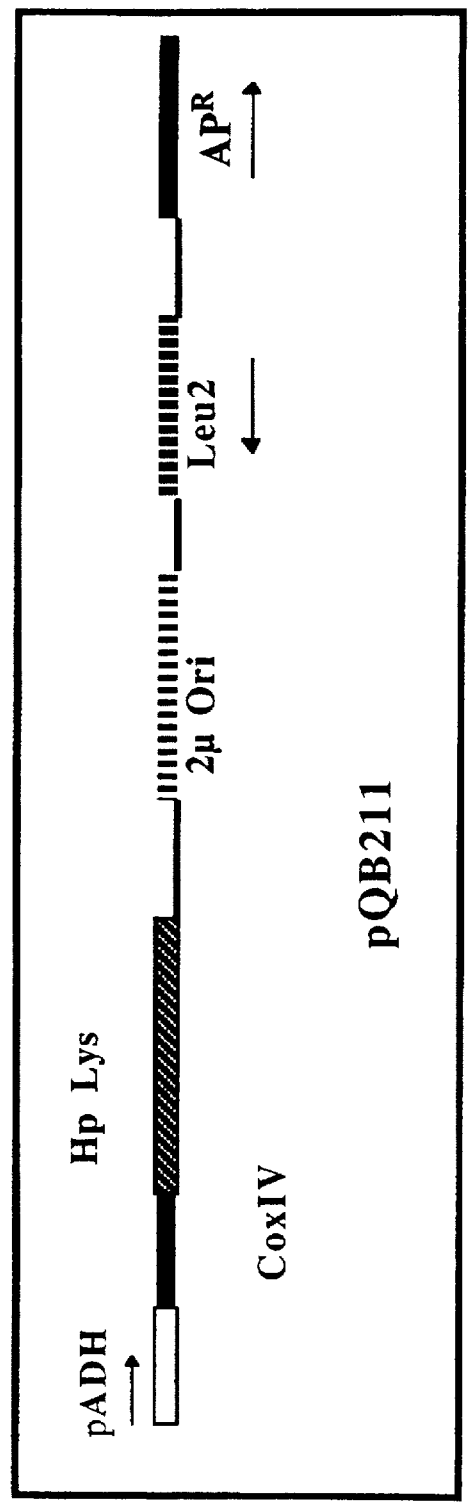
FIG. 5 is a schematic diagram of the structure of vector pQB211, a construct which directs the expression of an *H. pylori* lysyl-tRNA synthetase in *S. cerevisiae*, and includes a presequence for targeting the protein encoded by the inserted gene to mitochondria. (The circular plasmid is presented in linear form; PADH, alcohol dehydrogenase (ADH1) gene promoter; CoxIV, sequence encoding the first 22 amino acids of the cytochrome oxidase IV presequence; Hp Lys, *H. pylori* lysyl-tRNA synthetase; 2μ Ori, 2 micron origin of replication; Leu2, LEU2 selectable marker; AP$^R$, ampicillin resistance).

Purified *E. coli* SerRS and LysRS were assayed under the same conditions as the corresponding recombinant GST-fusion protein. *E. coli* SerRS and LysRS were partially purified on a DEAE column, and 10 µl of the partially pure preparation was used in an aminoacylation reaction. As negative controls, reactions without tRNA were carried out under the same conditions. The results are depicted in FIGS. 3 and 4.

Example 9
Functional Complementation of a Mitochondrial Lysyl-tRNA Synthetase Null Strain by *H. pylori* and Human Lysyl-tRNA Synthetase Genes in *Saccharomyces cerevisiae* Construction of Expression Vectors for Mitochondrial Targeting pQB111 and pQB136

The presequence from the cytochrome oxidase IV was used in the mitochondrial import vectors pQB111 and pQB136. This sequence has been used to allow import of several heterologous proteins in the mitochondria (Hurt, E. C., et al., *EMBO J.* 3:3149–3156 (1984); Pinkham, J., et al., *Mol. and Cell. Biol.* 14:4643–4652, (1994)).

In order to construct pQB111, an SphI-XbaI fragment bearing the ADH1 promoter and 22 of the 25 amino acids of COXIV (cytochrome oxidase IV) presequence were excised from plasmid pMC4 (obtained from J. Pinkham, University of Massachusetts, Amherst) (Bibus, C. R., et al., *J. Biol. Chem.* 263:13097–13102 (1988); Hurt, E. C., et al., *J. Biol. Chem.* 262:1420–1424 (1987)) and cloned into the SphI and XbaI sites of YEplac195 (also referred to as pQB42) (Sugino, A., and Gietz, R. D. Gene 74:527–534 (1988)) to form pQB111.

Plasmid pQB136 is a derivative of pQB111 which allows construction of GST (glutathione-S-transferase) fusion proteins targeted to mitochondria. PCR was used to amplify the GST gene from pGEX-4T-2 (Pharmacia) using the following primers:

5'-GCGCTCTAGATATCTGCTTATGTC-CCCTATACTAGGTTATTGG-3' (SEQ ID NO:54), and

5'-GGGGTACCTCACGATGCGGCCGCTCGAG-3' (SEQ ID NO:55).

(The ATG underlined in the 5'-primer is the start site of GST; the bases in boldface specify amino acids 22–25 of the COXIV presequence.) The 5' primer introduced an XbaI site (underlined), which when fused to the XbaI site in plasmid pQB111, restores the entire (25 amino acid residue) presequence of COXIV. The 3' primer introduced a KpnI site (underlined) downstream of the GST stop codon. The PCR product was cleaved with XbaI and KpnI and inserted into the XbaI and KpnI sites of pQB111 to yield pQB136.

pQB161

Plasmid pQB152, which encodes a GST-MSM1 protein fusion, was constructed by PCR amplification of the wild type MSM1 gene (mitochondrial methionyl-tRNA synthetase) from plasmid pQB104 (pG72/T1) (Tzagoloff, A., et al., *Eur. J. Biochem.* 179:365–371 (1989)), using the following primers:

5'-CCGCTCGAGCGATGCAATGTCGATCAATTGTGC-3' (SEQ ID NO:56)

and

5'-GGGGTACCCCTTTTTCATGACCTCATATTCG-3' (SEQ ID NO:57).

The PCR product was cleaved with XhoI and KpnI and cloned into the XhoI and KpnI sites of pQB136 to yield pQB152. In subsequent studies pQB152, encoding a GST-MSM1 fusion, was observed to complement msm1-1 and msm1::HIS3 strains on YEPG medium.

To construct pQB161, a KpnI-HindIII fragment containing the GST-MSM1 fusion gene of pQB152 was excised and cloned into the KpnI and HindIII sites of pQB41 (also referred to as YEplac181; Gietz and Sugino, *Gene*, 74: 527–534 (1988)), yielding pQB161. The backbone of pQB161 is similar to pQB111 in that it contains an ADH promoter and encodes the first 22 amino acids of COXIV; however, the plasmid bears a LEU2 selectable marker in lieu of the URA3 marker.

pQB218 (MSK1, URA3)

Plasmid pQB106 (also referred to as pG11/T6), which carries the yeast MSK1 gene (GenBank Accession No. X57360), has already been described (Gatti, D.L. and A. Tzagoloff, *J. Mol. Biol.*, 218: 557–568 (1991)). Genomic clone pG11/T6 (ATCC® No. 77080) is available from the American Type Culture Collection, 12301 Parklawn Drive, Rockville, Md. 20852-1776. A 3 kb XbaI fragment comprising the MSK1 gene was excised from pQB106, and inserted into the 2 µ URA3 vector YEplac195 (also referred to as pQB42) (Sugino, A., and Gietz, R. D. *Gene* 74:527–534 (1988)) to yield plasmid pQB218 (pC$^3$ 473). pQB218, which encodes the yeast MSK1 gene, and carries the URA3 selectable marker, can be used as a maintenance plasmid.

pQB211 (*H. pylori* LysRS gene, LEU2)

In order to clone the lysyl-tRNA synthetase gene from *H. pylori* into a mitochondrial targeting vector, the gene was first amplified using the following primers:

5'hplys (SEQ ID NO:58):
5'-CAGACGTCTAGATATCTGCTTATGTTTTCTAACCAATAC-3'

-continued

3'hplys (SEQ ID NO:59):
5'-ACCGCTCGAGCGGTTATTCTCCACTCTCCACATT-3'

PCR conditions were as follows: 94°, 1'; 60°, 1'; 72°, 2' for 35 cycles. Reactions contained 50 μl 1X Taq polymerase buffer, 0.2 mM of each dNTP, 2 μM of each primer, and 0.5 μl of Taq polymerase (2.5 units of AmpliTaq polymerase (Perkin-Elmer)). The template used for PCR amplification was cosmid clone #67 (see above). The 1.5 kb PCR product amplified with 5'hplys and 3'hplys primers was excised from 1% agarose gel, purified using a Gene CleanII Kit (Bio 101), and ligated to pT7Blue(R) vector (T-vector; Novagen) to generate plasmid pQB209 (pC$^3$ 464). The insert of pQB209 as excised with XbaI and KpnI and cloned into the corresponding sites of the vector backbone of plasmid pQB161 (which had been cleaved with XbaI and KpnI to release the GST-MSM1 fusion sequences) to generate plasmid pQB211 (pC$^3$ 466).

pQB210 (Human LysRS gene, LEU2)

The procedure for constructing a vector for expression and mitochondrial targeting of the human lysyl-tRNA synthetase gene was identical to that described above for *H. pylori* LysRS with the following differences. In order to clone the human lysyl-tRNA synthetase gene into the mitochondrial targeting vector, the gene was first amplified using the following primers:

5'hulys (SEQ ID NO:60):

5'-CAGACGTCTAGATATCTGCTTATGGCGGCCGGTGCAGGCG-3'

3'hulys (SEQ ID NO:61):

5'-TCTAGCTCGAGCTACACAGAAGTGCCAACTGTT-3'

(Primer 3'hulys introduces a silent mutation in the codon just before the stop codon (bold); the primer was designed to inactivate an XbaI site at this location). The template for amplification using the 5'hulys and 3'hulys primers was plasmid pM115 which contains a cDNA encoding human LysRS (K. Shiba; see also GenBank, National Center for Biotechnology Information (NCBI Seq ID: 505107), Accession No. D31890). A 1.8 kb PCR product was amplified, isolated as described above, and ligated to pT7Blue(R) vector (T-vector; Novagen) to generate plasmid pQB208 (pC$^3$ 463). The insert of pQB208 was excised with XbaI and KpnI and cloned into the corresponding sites of the vector backbone of plasmid pQB161 (which had been cleaved with XbaI and KpnI) to generate plasmid pQB210 (pC$^3$ 465).

Strains

Standard methods for yeast propagation and transformation were used (Ausubel, F. M., et al., *Current Protocols in Molecular Biology*, Greene Publishing Associates and John Wiley & Sons, Inc., (1993); Rose et al., 1990, *Methods in Yeast Genetics*, (Cold Spring Harbor Laboratory Press: Cold Spring Harbor, N.Y.).

QBY4

Strain QBY4, also referred to as EY722, has the following genotype: MATα ade2-1 his3-11,15 leu2-3,112 ura3-1 trp1-1 can1-100 Gal+)

QBY274

Strain QBY274, a karlΔ15 derivative of QBY4, was made by integrative transformation of W303 strain QBY4 with pMR1593. pMR1593 is a derivative of YIp5, which contains the karlΔ15 allele, and the URA3 and β-lactamase genes as selectable markers (Mark Rose, Princeton University, N.J.; *J. Cell. Biol.*, 117:1277–1287 (1992); see GenBank Accession No. M15683 (YSCKAR1) for KAR1 sequence). To direct integration into the KAR1 locus by integrative transformation, ten μg of pMR1593 were linearized with BglII and used to transform QBY4. Ura+ tranformants were selected, and passaged twice on synthetic complete medium containing 5-fluoroorotic acid (1 g/liter of 5-FOA) to select for the replacement of the chromosomal copy of KAR1 by the karlΔ15 allele and loss of the YIp5-derived vector. Chromosomal DNA was prepared from 10 independent isolates of the resulting strain. The chromosomal DNA was digested with NsiI and subjected to Southern analysis using a 600 bp fragment from plasmid pMR1593 as a probe. The results of the Southern analysis confirmed the presence of a deletion at the KAR1 locus. Strains containing the karlΔ15 allele were also tested for their deficiency in karyogamy by mating assay.

QBY47

The mitochondrial lysyl-tRNA synthetase deficient strain used was the disruption strain QBY47 (W303∇MSK1) (MATa ade2-1 his3-11,15 leu2-3,112 ura3-1 trp1-1 msk1::HIS3) (Gatti, D. L. and A. Tzagoloff, *J. Mol. Biol.*, 218: 557–568 (1991)).

QBY47 (pQB218)

Strain QBY47 (pQB218) was made by transforming QBY47 with pQB218. For complementation studies, a rho$^+$ derivative was constructed by cytoduction. In particular, 5×10$^6$ cells from logarithmic phase cultures of each of QBY47(pQB218) and QBY274 were mixed and spread onto a nitrocellulose filter laid on top of a YPD agar plate. The plate was incubated at 30° C. for 5 hours. Cytoductants were micromanipulated on YPD agar and allowed to form colonies; the colonies were later purified on SC-glycerol media lacking histidine and uracil to select for rho+ derivatives of QBY47(pQB218). Selection on 5-FOA plates following transformation was used to replace pQB218 (MSK+ URA3+) with the test plasmids, which were based on a LEU2-marked 2μ vector.

QBY171

Strain QBY171 has the following genotype: MATα mal rho+ and is available from the American Type Culture Collection (Accession No. ATCC 24658; Genetics, 49: 39 (1964)). The strain serves as a wildtype control.

Complementation of a Yeast Mitochondrial Gene Defect

Strains of *S. cerevisiae* having mutations (e.g., point mutations) in nuclear PET genes (petite or pet mutants), whose expression is required for the morphogenesis of respiratory-competent mitochondria, cannot grow on non-fermentable carbon sources such as glycerol media. However, because *S. cerevisiae* is a facultative anaerobe, such strains are capable of growing on fermentable carbon sources such as glucose, in the absence of mitochondrial function. On rich media such as glucose, these "petite" strains exhibit the small colony phenotype for which they are named. The majority of mitochondrial proteins, including the mitochondrial aminoacyl-tRNA synthetases, are nuclear encoded, synthesized in the cytoplasm and imported into mitochondria. Petite mutants of *S. cerevisiae* having defects in genes encoding a mitochondrial aminoacyl-tRNA synthetases have been identified (see e.g., Tzagoloff, A. and A. M. Myers, *Ann. Rev. Biochem.* 55:249–285 (1986); Tzagoloff, A. and C. L. Diekmann, *Microbiol. Rev.* 54(9):211–225 (1990); Myers, A. M., et al., *EMBO J.* 4(8):2087–2092 (1985)).

Although pet strains having mutations in nuclear genes encoding components of the mitochondrial translational apparatus, such as mitochondrial aminoacyl-tRNA synthetase genes, can grow on glucose, these strains tend to lose their mitochondrial DNA at high frequency, converting to rho– or rho° strains, with large deletions in their mitochondrial DNA (rho–) or no mitochondrial DNA (rho°) (Tzagoloff, A. and A. M. Myers, Ann. Rev. Biochem., 55:249–285 (1986); Myers, A. M., et al., EMBO J., 4(8):2087–2092 (1985)).

For complementation studies, functional mitochondria were introduced into strain QBY47, a strain having a mutation in the nuclear gene encoding mitochondrial lysyl-tRNA synthetase. Initial attempts to introduce functional mitochondria by mating strain QBY47 with the wild type strain QBY4 were unsuccessful. Although His+ rho+ diploids were isolated, when sporulated, these strains gave rise to inviable spores. Accordingly, functional mitochondria were introduced by cytoduction. First, a set of kar1Δ15 strains was constructed in the W303 background, including strain QBY274 used in this study. Strain QBY47 (pQB218) rho–, which carries the disruption allele (msk1::HIS3) and maintenance plasmid pQB218, was mated with QBY274 (QBY4 kar1Δ15) to introduce mitochondria by cytoduction as described above.

Complementation

Strain QBY47 (pQB218) rho+ was transformed with plasmid pQB211. Leu+ transformants were selected on Sc-Leu plates (synthetic complete medium, minus leucine). Selection on 5-FOA plates (synthetic complete medium containing 1 g/liter 5-fluoroorotic acid) was used to induce loss of the maintenance plasmid pQB218 (which carries the MSK1 and URA3 genes). 5-FOA resistant colonies were grown on a variety of plates to confirm their phenotype (Ura-Leu+His+), including YPD, SD, SC, (SC minus adenine), (SC minus leucine), (SC minus tryptophan), (SC minus uracil), (SC minus histidine), 5-FOA plates, and mating type lawns. 5-FOA resistant single colonies carrying plasmid pQB211 were then tested for complementation as indicated by growth on glycerol media (YEPG). The growth on YEPG plates (rich medium, supplemented with glycerol) of five of the 5-FOA resistant colonies was examined. Growth was weak compared to strain QBY47 (pQB218) rho+ or the general wild type strain QBY171. Growth on glycerol was shown to be plasmid-dependent, since cured Leu– strains (5 colonies tested) were no longer able to grow on YEPG plates. These results indicate that the H. pylori aaRS can substitute for the function of the host cell aminoacyl-tRNA synthetase. The transformants are examples of tester strains containing an H. pylori LysRS gene.

In the case of human LysRS complementation, plasmid pQB210 was isolated from complementing strains and its identity was verified by restriction digestion with EcoRI or EcoRV, using the original plamsid and pQB183 as controls. Attempts to recover pQB211 plasmid (hp lysRS) from complementing strains failed to yield E. coli transformants; detection of pQB211 by more sensitive methods such as PCR will further confirm these results.

The color of Ade– strains on YPD medium is often a good reflection of how well a certain plasmid can complement a mitochondrial tRNA synthetase defect. In the case of complementation by the H. pylori LysRS gene carried by pQB211, and the human LysRS gene carried by pQB210, the strains had a white appearance, suggesting weak complementation.

Example 10

Complementation Studies with H. pylori Isoleucyl- and Methionyl-tRNA Synthetase Genes in E. coli and Saccharomyces cervisiae E. coli Strains E. coli strain MI1 carries a chromosomal point mutation in the ileS gene, conferring an isoleucine auxotrophy (Iaccarino, M. and Berg, P., J. Bacteriol. 105:527–537 (1971); Treiber, G. and Iaccarino, M., J. Bacteriol. 107:828–832 (1971); and Schmidt, E. S. and P. Schimmel, Science, 264: 265–268 (1994)).

E. coli strain IQ844/pRMS711 is a derivative of IQ843/pRMS711 (Shiba, K. and P. Schimmel, Proc. Natl. Acad. Sci. USA, 89:1880–1884 (1992); Shiba, K. and P. Schimmel, Proc. Natl. Acad. Sci. USA, 89:9964–9968 (1992); Shiba, K. and P. Schimmel, J. Biol. Chem., 267:22703–22706 (1992)). The IQ843/pRMS711 and IQ844/pRMS711 strains each contain a chromosomal deletion of the ileS gene (ΔileS203::kan), and are propagated by expression of wild type IleRS at 30° C. from a temperature-sensitive maintenance plasmid designated pRMS711, which encodes the wild type ileS gene and a gene which confers chloramphenicol resistance. pRMS711 cannot replicate at 42° C.; thus, at the non-permissive temperature, the maintenance plasmid is lost. Following the introduction of a test construct into these strains, the growth of chloramphenicol sensitive colonies at 42° C. is indicative of complementation of the chromosomal ileS deletion by the introduced construct.

E. coli strain MN9261/pRMS615 (Kim, S., et al., Proc. Natl. Acad. Sci. USA 90:10046–10050 (1993)) carries a chromosomal null allele of metG. Strain MN9261/pRMS615 also contains a temperature sensitive maintenance plasmid (pRMS615) which carries a wild type metG allele (encoding E. coli MetRS), and has a temperature sensitive replicon which causes loss of the maintenance plasmid at the non-permissive temperature (e.g., 42° C.).

GST-H. pylori IleRS fusion gene complements the ileS defect in E. coli Strain MI1

E. coli strain MI1, which carries a chromosomal point mutation in the ileS gene (conferring an isoleucine auxotrophy), was used in complementation tests. MI1 cells were transformed with pGEXHPIRS-1 and were tested for viability on M9 medium (Maniatis et al., Molecular Cloning: A Laboratory Manual, (Cold Spring Harbor Laboratory Press: Cold Spring Harbor, N.Y.), containing 0.008% arginine and tryptophan, 100 µg/ml ampicillin, and 50 µg/ml IPTG at 37° C. for two days. MI1 cells transformed with the expression vector pGEX4T-2 (Pharmacia) served as a negative control, and MI1 cells transformed with a plasmid containing E. coli IleRS gene served as a positive control. Under the conditions set forth above, complementation of the ileS mutation of E. coli MI1 by the H. pylori IleRS fusion gene carried on pGEXHPIRS-1 was clearly observed.

The fusion constructs, which direct the expression of (a) a GST-IleRS fusion protein (pGEXHPIRS-1) or (b) a GST-MetRS fusion protein (pGEXHPMRS-1) were also introduced into E. coli strains having a null mutation in the corresponding E. coli host aaRS gene. In particular, E. coli strain IQ844/pRMS711 was transformed with pGEXHPIRS-1, and E. coli strain MN9261/pRMS615 was transformed with pGEXHPMRS-1. Transformants were tested at 42° C. to induce loss of the respective maintenance plasmids. Under the conditions of the assay, complementation was not observed. In contrast, E. coli strain IQ844/pRMS711 transformed with pKS21 (a control containing the E. coli ileS gene, encoding IleRS; Shiba, K. and P. Schimmel, Proc. Natl. Acad. Sci. USA, 89:1880–1884 (1992)) and E. coli strain MN9261/pRMS615 transformed with pJB104 (a control containing the E. coli MetG gene, encoding MetRS; Kim, S. and P. Schimmel, J. Biol. Chem., 267: 15563–67 (1992)) were able to grow at the non-permissive temperature (42°). Loss of the maintenance plasmid was verified by assessing antibiotic resistance. The nucleotide sequences of the IleRS and MetRS portions of the fusion constructs were confirmed by DNA sequencing. Adjustment of growth conditions may permit complementation.

S. cerevisiae cytoplasmic IleRS

A construct designed to express an H. pylori IleRS having the amino acid sequence shown in SEQ ID NO:2 was tested for complementation of a null allele of the S. cerevisiae cytoplasmic IleRS gene (ILS1) in strain QBY187. Strain QBY187 was constructed by transformation of a diploid (QBY182) (ILS1/ils1Δ::TRP1) with an ILS1 maintenance plasmid (pQB89; see Example 11) and Ura+transformants were selected. The transformant was sporulated, tetrads were dissected, a haploid Trp+Ura+spore was identified, and was designated QBY187 (MATα leu2Δ1 lys2–128δ ura3–52 trp1Δ63 ils1Δ::TRP1/pQB89). QBY187 was transformed with pQBHPIRS, which contains the H. pylori IleRS gene between the PstI/SalI sites of E. coli/S. cerevisiae shuttle vector pQB169 (see Example 11, below). To provide positive and negative controls, QBY187 cells were transformed with either plasmid pQB197 (which contains the wild type yeast ILS1 gene and a LEU2 selectable marker) or with vector pQB169, respectively. Leu+transformants of QBY187 containing pQBHPIRS, pQB197 or pQB169 were selected, and tested for viability at 30° C. on plates containing synthetic complete (SC) medium and 5-FOA. 5-FOA leads to loss of the maintenance plasmid pQB89, which carries a URA3 gene. Under the conditions used, complementation of the ils1Δ::TRP1 defect of strain QBY187 by pQBHPIRS was not observed. Similarly, no complementation was observed in the vector control. In contrast, QBY187 cells harboring pQB197, which carries the wild type yeast ILS1 gene, were able to grow under these conditions.

S. cerevisiae mitochondrial IleRS

A haploid yeast strain having a disruption (a HIS3 insertion) in the gene encoding the mitochondrial isoleucyl-tRNA synthetase (msi1::HIS3) was constructed. This strain was transformed with pQB240, a URA3 maintenance (CEN) plasmid in which the MSI1 gene is expressed from its natural promoter. A rho+ derivative carrying the maintenance plasmid was derived by cytoduction [strain QBY343 (W303 msi1::HIS3 (pQB240) rho+)]. The resulting strain was used to test two different constructs.

One construct (pQB242) was designed to express an H. pylori IleRS having the COXIV presequence fused to SEQ ID NO:2 ("native") (using an ATG initiation codon in place of the GTG initiation codon for expression). A second construct (pQB249) was designed to express a GST-H. pylori IleRS fusion protein, again using the COXIV presequence for mitochondrial targeting. pQB249 was constructed by excising the BamHI-SalI fragment containing a GST-H. pylori IleRS fusion protein from pGEXHPIRS-1 (see above), and ligating the fragment to the BamHI-SalI backbone of pQB153-GST (also referred to as pQB248)(see below).

Strain QBY343 was transformed with pQB242, pQB249, or a positive control construct. Leu+ transformants were isolated, and purified on 5-FOA plates to select for loss of the maintenance plasmid pQB240. Complementation of the petite phenotype was assessed on YEPG plates (2 days, 30° C.). Neither pQB242 nor pQB249 was observed to complement the msi1::HIS3 defect under conditions where control constructs (e.g., the yeast MSI1 gene) showed complementation. Expression of heterologous protein in yeast was confirmed in the case of the GST-fusion by visualization of the expressed fusion protein using anti-GST antibodies on a Western blot.

An H. pylori MetRS gene complements an msm1::HIS3 defect in S. cerevisiae

Construction of pQB153

Plasmid pQB150 is a derivative of pQB111 (Example 9), which contains a 1.7 kb BamHI fragment encoding the methionyl-tRNA synthetase gene from M. tuberculosis in the BamHI site of pQB111. pQB150 was digested with HindIII and KpnI, and the HindIII-KpnI fragment containing the methionyl-tRNA synthetase gene was inserted into the HindIII and KpnI sites of YEplac181 (also referred to as pQB41) (Sugino, A. and Gietz, R. D., Gene, 74: 527–534 (1988)) to form pQB154. pQB154 was digested with BamHI, releasing the methionyl-tRNA synthetase gene fragment. The vector portion was purified and religated to yield pQB153. pQB153 encodes the first 22 amino acids of COXIV under the control of an ADH promoter and bears a LEU2 selectable marker.

Construction of pQB153-GST (also referred to as pQB248)

Plasmid pQB153 was digested with XbaI and KpnI and the vector backbone was isolated. The GST coding region from plasmid pQB136 (see Example 9) was released by digestion with XbaI and KpnI, and the fragment was ligated to the XbaI-KpnI backbone of plasmid pQB153. The resulting construct is designated pQB153-GST or pQB248.

pQB153-GST is suitable for expressing GST-aaRS fusion proteins and mitochondrial targeting of the encoded fusion protein. The construct carries LEU2 as a selectable marker.

Construction of test plasmid pQB224 (pC$^3$479)

The H. pylori MetRS gene was cloned into the mitochondrial vector pQB153 (2μ, LEU2, ADH-COXIV) using XbaI and SalI sites (underlined in the primer sequences shown below) introduced during PCR amplification. The following primers were used:

5'-HP Met (SEQ ID NO:66):
5'-CAGACGTCTAGATATCTGCTTATGCAAAAATCACTGATCA-3'
Met 3' primer (SEQ ID NO:45):
5'-CCCAGTCGACTTAGCTGATCAAACTTCCTGC-3'

PCR conditions were as follows: 94° C., 60"; 55° C., 60"; 72° C., 120", for 35 cycles. Reactions contained 50 μl 1X Taq polymerase buffer, 0.2 mM of each dNTP, 2 μM of each primer, and 0.5 μl of Taq polymerase (2.5 units of AmpliTaq polymerase (Perkin-Elmer)). Approximately 20 ng of cosmid clone #30 (see Examples 3 and 4) was used as the template for amplification. The PCR product was cleaved with XbaI and SalI, and the fragment containing the amplified gene was isolated and inserted into pQB153 which had been cleaved with XbaI and SalI. The resulting plasmid, maintained in E. coli DH5α, is designated pQB224 or pC$^3$479.

Construction of maintenance plasmid pQB141

Plasmid pQB104 (pQB104 is referred to as pG72/T1 in Tzagoloff, A., et al., Eur. J. Biochem. 179:365–371 (1989); American Type Culture Collection, Rockville, Md., ATCC® Accession Nos. 37663, 66319) was digested with KpnI and PstI to obtain a 2.5 kb KpnI-PstI fragment containing the MSM1 gene promoter and entire MSM1 coding region. The 2.5 kb fragment was cloned into the KpnI and PstI sites of plasmid YCplac33 (Sugino, A., and Gietz, R. D., Gene 74:527–534 (1988)), which carries a URA3 selectable marker, to yield pQB141.

Strain QBY43:

Strain QBY43 (aW303ΔMSM1) has the following genotype: MATa ade2-1 his3–11, 15 leu2–3,112 ura3–1 trp1-1 msm1::HIS3 (Tzagoloff, A., et al., *Eur. J. Biochem.* 179:365–371 (1989)).

Strain QBY43 (pQB141):

Strain QBY43 (pQB141) was made by transformation of QBY43 with plasmid pQB141.

Strain QBY281:

Strain QBY281 (QBY43 (pQB141) rho+) was made by cytoduction from QBY43 (pQB141). 5×10$^6$ cells from logarithmic phase cultures of each of QBY43(pQB141) and QBY274 (see Example 9) were mixed and spread onto a nitrocellulose filter laid on top of a YPD agar plate. The plate was incubated at 30° C. for 5 hours. Cytoductants were micromanipulated on YPD agar and allowed to form colonies; the colonies were later purified on SC-glycerol media lacking histidine and uracil to select for rho+ derivatives of QBY43 (pQB141).

Strain QBY51 and QBY52:

The rho° strains QBY51 and QBY52 were obtained by growing QBY19 (MATa ade6 lys1) and QBY20 (MATα ade6 lys1) in YEPD (yeast extract, peptone, dextrose medium) containing 10 μg/ml of ethidium bromide (Sigma) to induce loss of mitochondrial DNA.

Complementation

Strain QBY281 was used as a recipient for transformation of plasmid pQB224. This strain was also transformed with individual positive control constructs containing (a) the wild type mitochondrial gene MSM1, (b) the *E. coli* metG gene, or (c) an *M. tuberculosis* MetRS gene, or with a negative control construct (vector pQB153-GST). The test plasmid and each of the control constructs contains a LEU2 selectable marker.

Leu+transformants containing the test plasmid and each of the control plasmids were selected on synthetic complete medium lacking leucine (SC - Leu). Leu+transformants were purified on plates containing 5-FOA, to select for loss of the maintenance plasmid pQB141, which carries the URA3 selectable marker. Single colonies selected on 5-FOA plates were resuspended in water in 32-well plates, and cells were transferred to a series of plates for analysis using an inoculating manifold (by "frogging"). In particular, transformants were transferred to the following types of plates to verify auxotrophies and to assess complementation (by growth on glycerol medium (YEPG)): YEPD; YEPG; SC; SD;. SC minus adenine; SC minus histidine; SC minus leucine; SC minus tryptophan; SC minus uracil, and 5-FOA plates. Subsequently, the 5-FOA plates were replica-plated to YEPG, and to mating lawns of rho° tester strains QBY51 and QBY52, which were then replica plated onto YEPG and SD. Growth on these plates verified mating type and the rho state of the transformants. Strains which form a diploid (as indicated by growth on SD medium) when crossed to QBY52 are MATa. Growth of a diploid on YEPG indicates that the transformant crossed to the rho° tester is rho+.

Four Leu+ colonies of QBY281 transformed with pQB224 and selected on 5-FOA plates were tested for their ability to complement on YEPG plates. After 2 days at 30° C. complementation was observed for all four colonies. All four Pet+ transformants were Ura-His+Leu+, confirming loss of the maintenance plasmid (which carries URA3), the presence of the disruption allele (msm1::HIS3), and the presence of the test plasmid, pQB224. Thus, these transformants are examples of tester strains containing an *H. pylori* MetRS gene. Growth of the four colonies was indistinguishable from that of Ura-His+Leu+ positive control strains (harboring the wild type mitochondrial gene MSM1, the *E. coli* metG gene, or an *M. tuberculosis* MetRS gene on a plasmid). In contrast, a strain transformed with the vector alone (pQB153-GST) was unable to grow on glycerol. These results indicate that an *H. pylori* MetRS gene can complement the defect in the yeast mitochondrial MSM1 gene of strain QBY281.

EXAMPLE 11

Construction of pQB169 and pQB172

Plasmid pMC4 carries the ADH promoter of *S. cerevisiae*, and downstream of the promoter, the coding sequence for the cytochrome oxidase IV mitochondrial targeting peptide (Pinkham, J. et al., *Mol. Cell. Biol.*, 14:4643–4652, (1994); Hurt, E. C. et al., *J. Biol. Chem.*, 262:1420–1424 (1987); Hurt, E. C., et al., *EMBO J.*, 3:3149–3156 (1984)). Derivatives of plasmid pMC4 can be constructed which lack or interrupt the sequence encoding the mitochondrial targeting sequence (e.g., by insertion of a gene between the promoter and targeting sequence), permitting cytoplasmic expression. Alternatively, the ADH promoter of pMC4 can be excised and inserted into another suitable vector. pQB169 and pQB172, which were constructed for the expression of heterologous genes in yeast cytoplasm, are examples of vectors constructed in this manner.

pQB169 contains the constitutive ADH promoter, a polylinker and the ILS1 transcriptional terminator. A 450 bp fragment containing the constitutive ADH promoter (PADH) with its transcriptional start sites (but not a translational start site (i.e., ATG)) was amplified by PCR using plasmid pMC4 as template. Primers were designed to incorporate a HindIII site at the 5' end (primer JK-1, SEQ ID NO:62) of the fragment and a PstI site at the 3' end (primer JK-2, SEQ ID NO:63):

```
          HindIII
JK-1: 5'-CCA AGA AGC TTG AAG TAA TAA TAG GCG CAT GC-3'      (SEQ ID NO:62)
           PstI
JK-2: 5'-CGT ACT GCA GGA TTG TAT GCT TGG TAT AGC-3'         (SEQ ID NO:63)
```

The resulting PCR product was cleaved with HindIII and PstI, and the HindIII-PstI fragment containing PADH was subcloned into the HindIII and PstI sites of vector YEplac181 (Gietz and Sugino, *Gene*, 74: 527–534 (1988)), a 2μ LEU2 yeast shuttle vector, to yield intermediate plasmid pQB147.

For efficient transcription termination, a 270 bp terminator fragment (tILS1), containing conserved transcription termination signals (Zaret and Sherman, *Cell*, 28: 563–573 (1982)) was generated by PCR, using plasmid pQB89 as template. pQB89 is a derivative of YCplac33 (a URA3, CEN4 plasmid; Geitz and Sugino, Gene, 74:527–534 (1988))). pQB89 was constructed by subcloning a 5.2 kb BamHI fragment obtained from a λ clone PM4967 (ATCC Accession No. 70323) containing a yeast genomic fragment which includes the ILS1 gene (yeast cytoplasmic isoleucyl-tRNA synthetase gene; Englisch et al., *Biol. Chem.* Hoppe-Seyler, 368: 971–979 (1987)) into YCplac33.

The 270 bp tILS1 PCR fragment was engineered to have an EcoRI site at the 5' end (JK-5, SEQ ID NO:64), and a NarI site at the 3' end (JK-6, SEQ ID NO:65), and contains the 3' untranslated region of ILS1, including bases 3519–3846 of the ILS1 gene. The primers used to prepare this fragment were:

```
        EcoRI
JK-5: 5'-GGA ATT CTG AAA ACA ACT CAT ATA AAT ACG-3'         (SEQ ID NO:64)
             NarI
JK-6: 5'-GAG GCG CCC TCT TAT CAA TCC CCT CCT CAA CC-3'      (SEQ ID NO:65)
```

The resulting PCR product was cleaved with EcoRI and NarI. pQB147 was cleaved with EcoRI and NarI, and the EcoRI-NarI tILS1 fragment was subcloned into the EcoRI and NarI sites of the vector to yield expression vector pQB169. Transformants of *E. coli* DH5α containing pQB169 were obtained. Transcription of a gene inserted into this vector can be initiated from pADH, and translation can be initiated at the first ATG of the insert.

To make a single-copy (CEN) version of this vector, the expression cassette (pADH-polylinker-tILS1) of pQB169 was excised with HindIII and NarI, and was subcloned into the HindIII and NarI sites of HindIII-NarI cut YCplac111 (Gietz and Sugino, Gene, 74:527–534 (1988)) to yield pQB172. Transformants of *E. coli* DH5α containing pQB172 were obtained.

Equivalents

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. An isolated nucleic acid which encodes at least a portion of a Helicobacter aminoacyl-tRNA synthetase selected from the group consisting of: isoleucyl-tRNA synthetase methionyl-tRNA synthetase, leucyl-tRNA synthetase, valyl-tRNA synthetase, lysyl-tRNA synthetase, and seryl-tRNA synthetase, said portion having catalytic activity or binding function.

2. The isolated nucleic acid of claim 1 which encodes an aminoacyl-tRNA synthetase.

3. The isolated nucleic acid of claim 1 which encodes an aminoacyl-tRNA synthetase of *Helicobacter pylori*.

4. The isolated nucleic acid of claim 1 which encodes at least a portion of an aminoacyl-tRNA synthetase of *Helicobacter pylori*.

5. An essentially pure nucleic acid which encodes a Helicobacter aminoacyl-tRNA synthetase selected from the group consisting of: isoleucyl-tRNA synthetase, methionyl-tRNA synthetase, leucyl-tRNA synthetase, valyl-tRNA synthetase, lysyl-tRNA synthetase, and seryl-tRNA synthetase, and which hybridizes under conditions of hybridization at 65° C. for 16–24 hours in 6X SSC / 10 mM EDTA / 0.5% SDS / 5X Denhardt's solution / 100 µg/ml sheared, denatured calf thymus DNA, washing twice with 2X SSC, 0.5% SDS solution at room temperature for 15 minutes, and once with 0.2X SSC / 0.5% SDS at 65° C. for one hour, to DNA having a sequence selected from the group consisting of the sequences shown in SEQ ID NO:1, SEQ ID NO:3, SEQ ID NO:5, SEQ ID NO:7, SEQ ID NO:9, SEQ ID NO:11 and the complementary strand of any one of the foregoing.

6. An essentially pure nucleic acid which encodes the amino acid sequence shown in SEQ ID NO:2.

7. An essentially pure nucleic acid which encodes the amino acid sequence shown in SEQ ID NO:4.

8. An essentially pure nucleic acid which encodes the amino acid sequence shown in SEQ ID NO:6.

9. An essentially pure nucleic acid which encodes the amino acid sequence shown in SEQ ID NO:8.

10. An essentially pure nucleic acid which encodes the amino acid sequence shown in SEQ ID NO:10.

11. An essentially pure nucleic acid which encodes the amino acid sequence shown in SEQ ID NO:12.

12. An isolated nucleic acid which encodes a protein comprising a helicobacter aminoacyl-tRNA synthetase or portion thereof having catalytic activity or binding function, wherein the aminoacyl-tRNA synthetase is selected from the group consisting of: isoleucyl-tRNA synthetase, methionyl-tRNA synthetase, leucyl-tRNA synthetase, valyl-tRNA synthetase, lysyl-tRNA synthetase, and seryl-tRNA synthetase.

13. The isolated nucleic acid of claim 12 which encodes a protein comprising a *Helicobacter pylori* aminoacyl-tRNA synthetase.

14. The isolated nucleic acid of claim 12 wherein the catalytic activity is aminoacylation activity.

15. The isolated nucleic acid of claim 12 wherein the catalytic activity is aminoacyl-adenylate formation.

16. An essentially pure nucleic acid which encodes a protein comprising a helicobacter isoleucyl-tRNA synthetase or portion thereof having catalytic activity or binding function and which hybridizes under conditions of hybridization at 65° C. for 16–24 hours in 6X SSC / 10 mM EDTA / 0.5 SDS / 5X Denhardt's solution / 100 µg/ml sheared, denatured calf thymus DNA, washing twice with 2X SSC, 0.5% SDS solution at room temperature for 15 minutes, and once with 0.2X SSC / 0.5% SDS at 65° C. for one hour, to DNA having sequence SEQ ID NO:1 or to the complement thereof.

17. An essentially pure nucleic acid which encodes a protein comprising a helicobacter methionyl-tRNA synthetase or portion thereof having catalytic activity or binding function and which hybridizes under conditions of hybridization at 65° C. for 16–24 hours in 6X SSC / 10 mM EDTA / 0.5% SDS / 5X Denhardt's solution / 100 µg/ml sheared, denatured calf thymus DNA, washing twice with 2X SSC, 0.5% SDS solution at room temperature for 15 minutes, and once with 0.2X SSC / 0.5% SDS at 65° C. for one hour, to DNA having sequence SEQ ID NO:3 or to the complement thereof.

18. An essentially pure nucleic acid which encodes a protein comprising a helicobacter leucyl-tRNA synthetase or portion thereof having catalytic activity or binding function and which hybridizes under conditions of hybridization at 65° C. for 16–24 hours in 6X SSC / 10 mM EDTA / 0.5% SDS / 5X Denhardt's solution / 100 µg/ml sheared, denatured calf thymus DNA, washing twice with 2X SSC, 0.5% SDS solution at room temperature for 15 minutes, and once with 0.2X SSC / 0.5% SDS at 65° C. for one hour, to DNA having sequence SEQ ID NO:5 or to the complement thereof.

19. An essentially pure nucleic acid which encodes a protein comprising a helicobacter valyl-tRNA synthetase or portion thereof having catalytic activity or binding function which hybridizes under conditions of hybridization at 65° C. for 16–24 hours in 6X SSC / 10 mM EDTA / 0.5% SDS / 5X Denhardt's solution / 100 µg/ml sheared, denatured calf thymus DNA, washing twice with 2X SSC, 0.5% SDS solution at room temperature for 15 minutes, and once with 0.2X SSC / 0.5% SDS at 65° C. for one hour, to DNA having sequence SEQ ID NO:7 or to the complement thereof.

20. An essentially pure nucleic acid which encodes a protein comprising a helicobacter lysyl-tRNA synthetase or portion thereof having catalytic activity or binding function and which hybridizes under conditions of hybridization at 65° C. for 16–24 hours in 6X SSC / 10 mM EDTA / 0.5% SDS / 5X Denhardt's solution / 100 µg/ml sheared, denatured calf thymus DNA, washing twice with 2X SSC, 0.5% SDS solution at room temperature for 15 minutes, and once with 0.2X SSC / 0.5% SDS at 65° C. for one hour, to DNA having sequence SEQ ID NO:9 or to the complement thereof.

21. An essentially pure nucleic acid which encodes a protein comprising a helicobacter seryl-tRNA synthetase or portion thereof having catalytic activity or binding function and which hybridizes under conditions of hybridization at 65° C. for 16–24 hours in 6X SSC / 10 mM EDTA / 0.5% SDS / 5X Denhardt's solution / 100 µg/ml sheared, denatured calf thymus DNA, washing twice with 2X SSC. 0.5% SDS solution at room temperature for 15 minutes, and once with 0.2X SSC / 0.5% SDS at 65° C. for one hour, to DNA having sequence SEQ ID NO:11 or to the complement thereof.

22. An isolated nucleic acid comprising a nucleic acid that hybridizes under conditions of hybridization at 65° C. for 16–24 hours in 6X SSC / 10 mM EDTA / 0.5% SDS / 5X Denhardt's solution / 100 µg/ml sheared, denatured calf thymus DNA, washing twice with 2X SSC, 0.5% SDS solution at room temperature for 15 minutes, and once with 0.2X SSC / 0.5% SDS at 65° C. for one hour, to a DNA molecule having a sequence selected from the group consisting of:

(a) the top strand shown in SEQ ID NO:1;
(b) the top strand shown in SEQ ID NO:3;
(c) the top strand shown in SEQ ID NO:5;
(d) the top strand shown in SEQ ID NO:7;
(e) the top strand shown in SEQ ID NO:9; and
(f) the top strand shown in SEQ ID NO:11.

23. A recombinant vector comprising nucleic acid which encodes a protein comprising at least a portion of a helicobacter aminoacyl-tRNA synthetase selected from the group consisting of: isoleucyl-tRNA synthetase, methionyl-tRNA synthetase, leucyl-tRNA synthetase, valyl-tRNA synthetase, lysyl-tRNA synthetase, and seryl-tRNA synthetase, said portion having catalytic activity or binding function.

24. The recombinant vector of claim 23 comprising nucleic acid which encodes a helicobacter aminoacyl-tRNA synthetase.

25. The recombinant vector of claim 23 wherein the helicobacter aminoacyl-tRNA synthetase is a *Helicobacter pylori* aminoacyl-tRNA synthetase.

26. A recombinant vector comprising nucleic acid which encodes a protein comprising at least a portion of a helicobacter aminoacyl-tRNA synthetase selected from the group consisting of: isoleucyl-tRNA synthetase, methionyl-tRNA synthetase, leucyl-tRNA synthetase, valyl-tRNA synthetase, lysyl-tRNA synthetase, and seryl-tRNA synthetase, said portion having catalytic activity or binding function, wherein the nucleic acid hybridizes under conditions of hybridization at 65° C. for 16–24 hours in 6X SSC / 10 mM EDTA / 0.5% SDS / 5X Denhardt's solution / 100 µg/ml sheared, denatured calf thymus DNA, washing twice with 2X SSC, 0.5% SDS solution at room temperature for 15 minutes, and once with 0.2X SSC / 0.5% SDS at 65° C. for one hour, to DNA having a sequence selected from the group consisting of the sequences shown in SEQ ID NO:1, SEQ ID NO:3, SEQ ID NO:5, SEQ ID NO:7, SEQ ID NO:9 SEQ ID NO:11 and the complementary strand of any one of the foregoing.

27. A host cell comprising a recombinant gene which can express a protein comprising a helicobacter aminoacyl-tRNA synthetase or a portion thereof having catalytic activity or binding function, wherein the helicobacter aminoacyl-tRNA synthetase is selected from the group consisting of: isoleucyl-tRNA synthetase, methionyl-tRNA synthetase, leucyl-tRNA synthetase, valyl-tRNA synthetase, lysyl-tRNA synthetase, and seryl-tRNA synthetase.

28. The host cell of claim 27, wherein the helicobacter aminoacyl-tRNA synthetase is a *Helicobacter pylori* aminoacyl-tRNA synthetase.

29. A method for producing a protein comprising a helicobacter aminoacyl-tRNA synthetase or a portion thereof having catalytic activity or binding function, comprising maintaining a host cell of claim 27 under conditions suitable for expression of said protein, whereby said protein is produced.

30. The method of claim 29, further comprising isolating said protein.

31. A host cell comprising a recombinant nucleic acid encoding a fusion protein comprising a helicobacter aminoacyl-tRNA synthetase or portion thereof having catalytic activity or binding function, wherein the aminoacyl-tRNA synthetase is selected from the group consisting of: isoleucyl-tRNA synthetase, methionyl-tRNA synthetase, leucyl-tRNA synthetase, valyl-tRNA synthetase, lysyl-tRNA synthetase and seryl-tRNA synthetase.

32. A method for producing a fusion protein comprising a helicobacter aminoacyl-tRNA synthetase, comprising maintaining a host cell of claim 31, under conditions suitable for expression of said fusion protein, whereby said fusion protein is produced.

33. The method of claim 32, further comprising isolating the fusion protein.

34. The host cell of claim 31 wherein the aminoacyl-tRNA synthetase is a *Helicobacter pylori* aminoacyl-tRNA synthetase.

35. A host cell comprising a recombinant nucleic acid encoding a protein comprising a helicobacter isoleucyl-tRNA synthetase or portion thereof having catalytic activity or binding function.

36. A method for producing a protein comprising a helicobacter isoleucyl-tRNA synthetase or a portion thereof having catalytic activity or binding function, comprising maintaining the host cell of claim 35 under conditions suitable for expression of said protein, whereby said protein is produced.

37. The method of claim 36, further comprising isolating said protein.

38. A host cell comprising a recombinant nucleic acid encoding a protein comprising a helicobacter methionyl-tRNA synthetase or portion thereof having catalytic activity or binding function.

39. A method for producing a protein comprising a helicobacter methionyl-tRNA synthetase or a portion thereof having catalytic activity or binding function, comprising maintaining the host cell of claim 38 under conditions suitable for expression of said protein, whereby said protein is produced.

40. The method of claim 39, further comprising isolating said protein.

41. A host cell comprising a recombinant nucleic acid encoding a protein comprising a helicobacter leucyl-tRNA synthetase or portion thereof having catalytic activity or binding function.

42. A method for producing a protein comprising a helicobacter leucyl-tRNA synthetase or a portion thereof having catalytic activity or binding function, comprising maintaining the host cell of claim 41 under conditions suitable for expression of said protein, whereby said protein is produced.

43. The method of claim 42, further comprising isolating said protein.

44. A host cell comprising a recombinant nucleic acid encoding a protein comprising a helicobacter valyl-tRNA synthetase or portion thereof having catalytic activity or binding function.

45. A method for producing a protein comprising a helicobacter valyl-tRNA synthetase or a portion thereof having catalytic activity or binding function, comprising maintaining the host cell of claim 44 under conditions suitable for expression of said protein, whereby said protein is produced.

46. The method of claim 45, further comprising isolating said protein.

47. A host cell comprising a recombinant nucleic acid encoding a protein comprising a helicobacter lysyl-tRNA synthetase or portion thereof having catalytic activity or binding function.

48. A method for producing a protein comprising a helicobacter lysyl-tRNA synthetase or a portion thereof having catalytic activity or binding function, comprising maintaining the host cell of claim 47 under conditions suitable for expression of said protein, whereby said protein is produced.

49. The method of claim 48, further comprising isolating said protein.

50. A host cell comprising a recombinant nucleic acid encoding a protein comprising a helicobacter seryl-tRNA synthetase or portion thereof having catalytic activity or binding function.

51. A method for producing a protein comprising a helicobacter seryl-tRNA synthetase or a portion thereof having catalytic activity or binding function, comprising maintaining the host cell of claim 50 under conditions suitable for expression of said protein, whereby said protein is produced.

52. The method of claim 51, further comprising isolating said protein.

53. A method for producing isolated, recombinant helicobacter aminoacyl-tRNA synthetase, wherein the helicobacter aminoacyl-tRNA synthetase is selected from the group consisting of: isoleucyl-tRNA synthetase, methionyl-tRNA synthetase, leucyl-tRNA synthetase, valyl-tRNA synthetase, lysyl-tRNA synthetase, and seryl-tRNA synthetase, comprising the following steps:
   a) constructing a recombinant nucleic acid vector comprising a coding sequence for a helicobacter aminoacyl-tRNA synthetase wherein the coding sequence is under control of transcription signals and is linked to appropriate translation signals;
   b) introducing the vector into suitable host cells which support replication of the vector;
   c) maintaining the host cells under conditions in which the coding sequence for the helicobacter aminoacyl-tRNA synthetase is expressed; and
   d) isolating helicobacter aminoacyl-tRNA synthetase from the host cells.

54. A method for producing isolated, recombinant helicobacter aminoacyl-tRNA synthetase, wherein the helicobacter aminoacyl-tRNA synthetase is selected from the group consisting of: isoleucyl-tRNA synthetase, methionyl-tRNA synthetase, leucyl-tRNA synthetase, valyl-tRNA synthetase, lysyl-tRNA synthetase, and seryl-tRNA synthetase, comprising the following steps:
   a) providing host cells containing a recombinant gene encoding helicobacter aminoacyl-tRNA synthetase;
   b) maintaining the host cells under conditions in which the gene is expressed; and
   c) isolating helicobacter aminoacyl-tRNA synthetase from the host cells.

55. The method of claim 54 wherein the helicobacter aminoacyl-tRNA synthetase is a *Helicobacter pylori* aminoacyl-tRNA synthetase.

56. A method for producing isolated, recombinant polypeptide comprising a helicobacter aminoacyl-tRNA synthetase, comprising maintaining a host cell comprising a recombinant nucleic acid encoding said polypeptide under conditions suitable for expression of the nucleic acid and production of said polypeptide, and isolating said polypeptide, wherein said polypeptide is selected from the group consisting of: GST-isoleucyl-tRNA synthetase, GST-methionyl-tRNA synthetase, GST-leucyl-tRNA synthetase, GST-valyl-tRNA synthetase, GST-lysyl-tRNA synthetase, and GST-seryl-tRNA synthetase.

57. The method of claim 56 wherein said aminoacyl-tRNA synthetase is a *Helicobacter pylori* aminoacyl-tRNA synthetase.

58. A method for producing a fusion protein comprising a helicobacter aminoacyl-tRNA synthetase selected from the group consisting of isoleucyl-tRNA synthetase, methionyl-tRNA synthetase, leucyl-tRNA synthetase, valyl-tRNA synthetase, lysyl-tRNA synthetase and seryl-tRNA synthetase, comprising maintaining a host cell of claim 34 under conditions suitable for expression of said fusion protein, whereby said fusion protein is produced.

59. The method of claim 58, further comprising isolating the fusion protein.

60. A tester strain comprising host cells comprising a gene encoding a protein comprising a helicobacter aminoacyl-tRNA synthetase or a portion thereof having catalytic activity or binding function, wherein the gene complements or substitutes in function for a host cell aminoacyl-tRNA synthetase gene, and wherein the helicobacter aminoacyl-tRNA synthetase is selected from the group consisting of: isoleucyl-tRNA synthetase, methionyl-tRNA synthetase, leucyl-tRNA synthetase, valyl-tRNA synthetase, lysyl-tRNA synthetase, and seryl-tRNA synthetase.

61. The tester strain of claim 60 in which a host gene encoding an aminoacyl-tRNA synthetase has been lost or has been altered relative to wild type so as to make no gene product, a gene product which is inactive, or a gene product which can be conditionally made inactive.

62. The tester strain of claim 60 wherein the protein comprising a helicobacter aminoacyl-tRNA synthetase or a portion thereof having catalytic activity or binding function comprises a *Helicobacter pylori* aminoacyl-tRNA synthetase.

63. The tester strain of claim 60, wherein the host cells are *S. cerevisiae*, and the gene encoding a protein comprising a helicobacter aminoacyl-tRNA synthetase or a portion thereof having catalytic activity or binding function complements or substitutes in function for a defect in a host mitochondrial aminoacyl-tRNA synthetase gene.

* * * * *